US012788085B2

(12) United States Patent
Eschen et al.

(10) Patent No.: US 12,788,085 B2
(45) Date of Patent: Nov. 10, 2026

(54) SURGICAL GARMENT AND METHODS OF DONNING THE SAME

(71) Applicant: Stryker Corporation, Kalamazoo, MI (US)

(72) Inventors: Kevin Paul Eschen, Portage, MI (US); Owen Blough, Vicksburg, MI (US); Matthew Van Nortwick, Ann Arbor, MI (US)

(73) Assignee: Stryker Corporation, Portage, MI (US)

( * ) Notice: Subject to any disclaimer, the term of this patent is extended or adjusted under 35 U.S.C. 154(b) by 402 days.

(21) Appl. No.: 18/145,345

(22) Filed: Dec. 22, 2022

(65) Prior Publication Data

US 2023/0276874 A1 Sep. 7, 2023

Related U.S. Application Data

(60) Provisional application No. 63/294,574, filed on Dec. 29, 2021.

(51) Int. Cl.
*A41D 13/12* (2006.01)
*A41D 13/00* (2006.01)
(Continued)

(52) U.S. Cl.
CPC ....... *A41D 13/1209* (2013.01); *A41D 13/129* (2013.01); *A41D 13/0005* (2013.01);
(Continued)

(58) Field of Classification Search
CPC .............. A41D 13/1209; A41D 13/129; A41D 13/1227; A41D 13/0005; A41D 19/0089;
(Continued)

(56) References Cited

U.S. PATENT DOCUMENTS 2,226,066 A * 12/1940 Moe ....................... A41D 27/10
2/270
3,657,741 A 4/1972 Blanco
(Continued)

FOREIGN PATENT DOCUMENTS

CN 213606965 U * 7/2021
CN 218338527 U * 1/2023
(Continued)

OTHER PUBLICATIONS

CN-218338527-U English Translation (Year: 2022).*
CN-213606965-U English Translation (Year: 2020).*

*Primary Examiner* — Khaled Annis
*Assistant Examiner* — Dakota Marin
(74) *Attorney, Agent, or Firm* — Howard & Howard Attorneys PLLC

(57) ABSTRACT

A surgical garment worn by an individual. The surgical garment includes a sleeve having a distal end defining a lumen for receiving a hand and/or arm of the individual and a cuff portion disposed at the distal end of the sleeve. The cuff portion extends the lumen defined by the sleeve and further defines an opening. In addition, a barrier member is provided. The barrier member is disposed within the lumen proximal to the opening and configured to selectively prevent the hand of the individual from extending through the opening defined by the cuff portion.

17 Claims, 25 Drawing Sheets

(51) Int. Cl.

| | |
|---|---|
| *A41D 19/00* | (2006.01) |
| *A41D 19/015* | (2006.01) |
| *A41D 27/10* | (2006.01) |
| *A61B 46/00* | (2016.01) |
| *A61B 46/20* | (2016.01) |
| *A61B 46/27* | (2016.01) |
| *A62B 17/00* | (2006.01) |

(52) U.S. Cl.

CPC ...... *A41D 13/1227* (2013.01); *A41D 19/0034* (2013.01); *A41D 19/0037* (2013.01); *A41D 19/0041* (2013.01); *A41D 19/0044* (2013.01); *A41D 19/0048* (2013.01); *A41D 19/0089* (2013.01); *A41D 19/01594* (2013.01); *A41D 27/10* (2013.01); *A61B 46/00* (2016.02); *A61B 46/20* (2016.02); *A61B 2046/201* (2016.02); *A61B 46/27* (2016.02); *A62B 17/001* (2013.01)

(58) Field of Classification Search

CPC .......... A41D 19/01594; A41D 19/0034; A41D 19/0037; A41D 19/0041; A41D 19/0044; A41D 19/0048; A41D 27/10; A62B 17/001; A61B 46/00; A61B 46/20; A61B 46/27; A61B 2046/201

USPC ................................ 2/60; 128/849, 856, 878

See application file for complete search history.

(56) References Cited

U.S. PATENT DOCUMENTS

| | | | | | |
|---|---|---|---|---|---|
| 4,114,200 | A * | 9/1978 | Smith | A41D 13/1227 | 2/51 |
| 4,389,734 | A * | 6/1983 | Franz | A41D 13/1227 | 2/60 |
| 4,543,670 | A * | 10/1985 | Ehring | A41D 27/10 | 2/124 |
| 4,752,972 | A * | 6/1988 | Neckerman | A41D 13/1209 | 66/172 E |
| 4,860,386 | A | 8/1989 | Martin | | |
| 4,982,448 | A | 1/1991 | Kogut | | |
| 5,073,988 | A * | 12/1991 | Lewis, Jr. | A41D 19/0041 | 2/270 |
| 5,097,534 | A | 3/1992 | Viemeister et al. | | |
| 5,555,561 | A * | 9/1996 | Plachta | A41D 13/0005 | 2/457 |
| 5,628,067 | A | 5/1997 | Meyer et al. | | |
| 5,724,674 | A | 3/1998 | Covington et al. | | |
| 5,749,098 | A * | 5/1998 | Evans | A41D 19/0041 | 2/124 |
| 6,126,621 | A * | 10/2000 | Aceves | A61F 13/041 | 128/878 |
| 6,523,181 | B2 * | 2/2003 | Medves | A41D 19/0089 | 2/160 |
| 6,665,880 | B2 * | 12/2003 | Poppe | A41D 27/10 | 2/114 |
| 6,715,159 | B2 * | 4/2004 | Cormier | A41D 13/0005 | 2/457 |
| 6,996,847 | B2 * | 2/2006 | Anderson | A41D 19/0013 | 2/16 |
| 7,302,711 | B1 * | 12/2007 | Tanenbaum | A41D 19/0089 | 2/161.7 |
| 7,370,369 | B2 * | 5/2008 | Cheung | A41D 13/1209 | 2/114 |
| 7,685,649 | B2 * | 3/2010 | Jordan | A41D 13/1209 | 2/457 |
| 7,841,020 | B2 | 11/2010 | Mayfield et al. | | |
| 8,112,820 | B2 * | 2/2012 | Johnson | A41D 13/0005 | 2/160 |
| 8,904,564 | B2 * | 12/2014 | Laycock | A41D 19/0041 | 2/93 |
| 9,687,032 | B2 | 6/2017 | McBride et al. | | |
| 10,111,474 | B2 | 10/2018 | Keathley | | |
| 10,165,814 | B2 * | 1/2019 | Thompson | A41F 1/002 | |
| 10,188,476 | B1 | 1/2019 | Jain et al. | | |
| 10,391,740 | B2 | 8/2019 | Bailey et al. | | |
| 10,531,697 | B2 * | 1/2020 | Hussey | A41D 27/245 | |
| 10,750,800 | B2 | 8/2020 | Jefferis et al. | | |
| 11,382,365 | B2 * | 7/2022 | Musgrove | A41D 19/0089 | |
| 11,589,626 | B2 * | 2/2023 | Carter | A41D 27/10 | |
| 12,070,089 | B2 * | 8/2024 | Howell | A41D 13/0005 | |
| 2005/0223471 | A1 * | 10/2005 | Griesbach, III | A41D 19/0089 | 2/160 |
| 2005/0241046 | A1 * | 11/2005 | Griesbach, III | A41D 19/0041 | 2/160 |
| 2008/0256677 | A1 * | 10/2008 | Loos | A43B 23/06 | 2/200.2 |
| 2011/0024485 | A1 | 2/2011 | Porowski | | |
| 2011/0239349 | A1 * | 10/2011 | Thompson | A41D 13/1209 | 2/48 |
| 2013/0318693 | A1 | 12/2013 | McBride et al. | | |
| 2014/0157475 | A1 * | 6/2014 | Smith | A41D 19/0044 | 2/16 |
| 2015/0197324 | A1 * | 7/2015 | Marlin | B63C 11/04 | 2/2.15 |
| 2016/0120241 | A1 | 5/2016 | Rose | | |
| 2018/0020751 | A1 * | 1/2018 | Lewis | A41D 19/0013 | 2/69 |
| 2018/0071173 | A1 * | 3/2018 | Hunter | A41D 19/01 | |
| 2018/0304106 | A1 * | 10/2018 | O'Leary | A62B 17/001 | |
| 2018/0352878 | A1 * | 12/2018 | Smith | A41D 13/0005 | |
| 2019/0059472 | A1 | 2/2019 | Hopkins | | |
| 2020/0060375 | A1 | 2/2020 | Jascomb et al. | | |
| 2020/0121006 | A1 | 4/2020 | Randall et al. | | |
| 2020/0375272 | A1 | 12/2020 | Ulmer et al. | | |
| 2021/0106084 | A1 | 4/2021 | Markoglou et al. | | |
| 2021/0177076 | A1 * | 6/2021 | Clark | A47G 25/90 | |
| 2021/0204621 | A1 | 7/2021 | Jefferis | | |
| 2021/0213323 | A1 | 7/2021 | Trebino | | |

FOREIGN PATENT DOCUMENTS

| | | | |
|---|---|---|---|
| EP | 2234676 | B1 | 7/2012 |
| WO | 2019147923 | A1 | 8/2019 |
| WO | 2019226810 | A1 | 11/2019 |

* cited by examiner

FIG. 1
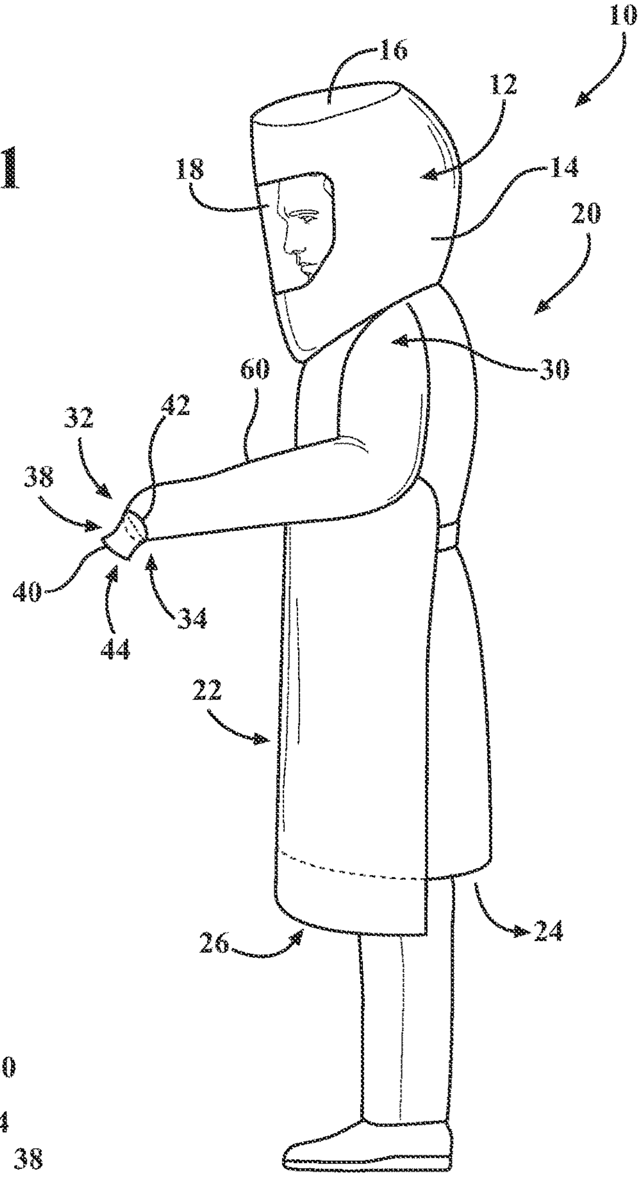
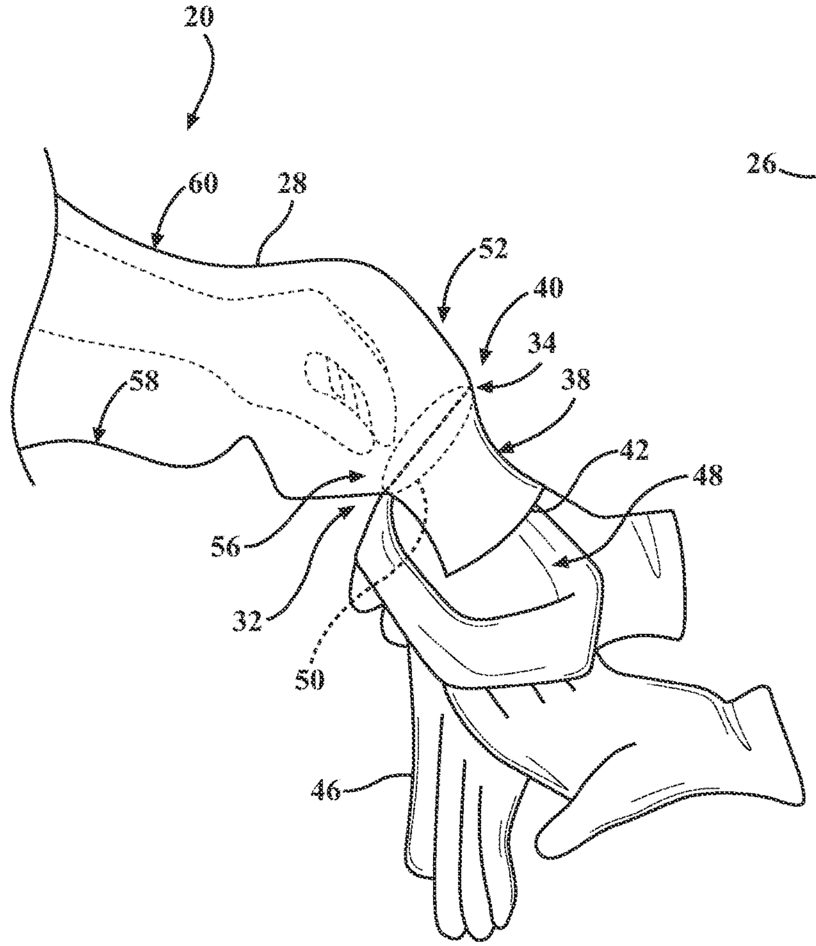
FIG. 2

SURGICAL GARMENT AND METHODS OF DONNING THE SAME

CROSS-REFERENCE TO RELATED APPLICATIONS

The present application claims the priority to and all the benefits U.S. Provisional Patent Application No. 63/294,574, filed on Dec. 29, 2021, which is hereby expressly incorporated herein by reference in its entirety.

FIELD OF THE INVENTION

The subject disclosure relates, generally, to wearable surgical garments, and more specifically, to a surgical garment and methods of donning the same.

BACKGROUND

During medical or surgical procedures or while in an operating room, it is common practice for every person in the operating room to wear a surgical garment and gloves for sterility purposes. Such garments include overhead gowns, tie-close gowns, zippered gowns, and the like. Surgical garments and gloves can be used to effectively seal off the wearers from a non-sterile environment or protect themselves from exposure to fluids and micro-organisms before and during a medical or surgical procedure. It is important for surgical garments to be put on easily (donning) and removed (doffing) while ensuring compliance with sterility guidelines and limiting cross contamination by the wearer.

Donning the surgical garment and gloves in a manner that maintains sterility is critical. As such, the general practice is for the wearer to keep their hands and arms on one side of the sterile barrier created by the surgical garment, gloves and related personal protection equipment defining the sterile barrier between the wearer and the sterile environment, such as the operating room or surgical site on the patient. Various techniques have been used to avoid contaminating or compromising the sterility of the surgical garment on the sterile environment side of the sterile barrier and the wearer such as the use of an assistant. Typically, the assistant is needed to secure a garment around a wearer and gloves over the wearer's hands. One way of accomplishing this is for the wearer to avoid extending their hands and/or arm through the opening at the end of the sleeve until the gloves are secured over the opening in order to keep the wearer's hands and arm from crossing the sterile barrier defined by the garment and potentially contaminated the sterile environment on the opposing side of the sterile barrier. Presently, the wearer must be aware of and manually stop their hand/arm from exiting the sleeve and crossing the sterile barrier provided by the garment prior to the assistant placing the glove over the opening in the sleeve of the garment.

To reduce the need for an assistant in donning a surgical garment, gloves, and/or related personal protection equipment, and to prevent accidental exposures between the sterile and non-sterile environments defined by the sterile barrier, the present disclosure provides surgical garments and methods to allow self-donning while maintaining the sterile barrier between the wearer and the sterile environment.

SUMMARY

This Summary introduces a selection of concepts in a simplified form that are further described below in the Detailed Description below. This Summary is not intended to limit the scope of the claimed subject matter nor identify key features or essential features of the claimed subject matter.

In one aspect, a surgical garment worn by an individual. The surgical garment also includes a sleeve having a distal end defining a lumen for receiving a hand and/or arm of the individual. The garment also includes a cuff portion disposed at the distal end of the sleeve, the cuff portion extending the lumen defined by the sleeve and further defining an opening. The garment also includes a barrier member disposed within the lumen proximal to the opening and configured to selectively prevent the hand of the individual from extending through the opening defined by the cuff portion.

Implementations may include one or more of the following features. The surgical garment where the barrier member is positioned within the lumen at an intersection of the distal end of the sleeve and a proximal end of the cuff portion. The barrier member is configured to transition from a closed configuration to an open configuration. When the barrier member is in the closed configuration, the barrier member defines a barrier between the lumen defined by the sleeve and the external environment through the opening defined by the cuff portion. The barrier member is coupled to the distal end of the sleeve covering an opening defined at the distal end of the sleeve. The surgical garment of any of the preceding claims, may include: a body portion, the sleeve extending from the body portion; a hood coupled to the body portion, the hood defining an opening configured to be in front of the individual's face when disposed over individual and/or a surgical helmet; a transparent face shield disposed over the opening defined in the hood; and at least one attachment element disposed on the hood and/or transparent face shield, the attachment element for removably coupling the surgical garment to the surgical helmet. The transparent face shield is formed of a flexible and transparent material and including a top portion, a bottom portion, and a sealing perimeter, the transparent face shield may include: a pair of lower attachment elements disposed on the bottom portion of the face shield; and an upper attachment element disposed on the top portion of the face shield, the upper and lower attachment elements defining three mounting locations at which the face shield is removably mounted to the surgical helmet; where the face shield defines a bounded cut, the bounded cut being disposed between the sealing perimeter and an outer edge of the face shield; and where the bounded cut being at least partially disposed between the upper attachment element and at least one of the pair of lower attachment elements.

In a second aspect, a personal protection system to be worn by an individual. The personal protection system also includes a surgical garment. The system also includes a garment body including a material configured to provide a sterile barrier between the individual and an external environment. The system also includes a sleeve extending from the garment body and defining a lumen for receiving a hand and/or arm of the individual, the sleeve defining an opening at a distal end of the sleeve. The system also includes the sleeve is transitionable between a closed configuration and an open configuration, when in the closed configuration, the sleeve includes a barrier member to define a barrier preventing the hand of the individual from extending through the opening.

In a third aspect, a protective garment worn by an individual. The protective garment also includes a garment body including a material configured to provide a sterile barrier between the individual and an external environment. The garment also includes a sleeve extending from the garment body, the sleeve having a distal end and a proximal end and defining a lumen for receiving a hand and/or arm of the individual. The garment also includes a cuff portion disposed at the distal end of the sleeve, the cuff portion extending the lumen defined by the sleeve and further defining an opening. The garment also includes a barrier member disposed within the lumen defined by the sleeve and configured to selectively prevent the hand of the individual from extending through the opening defined by the cuff portion.

In a fourth aspect, a method of donning a personal protection system. The method also includes providing a protective garment including a sleeve defining a lumen and an opening at a distal end of the sleeve, the lumen configured to receive a hand and/or arm of an individual wearing the protective garment, and a barrier member disposed within the lumen and configured to define a barrier preventing access to the lumen from an external environment via the opening. The method also includes inserting the hand and/or arm of the individual into the lumen through a proximal opening of the sleeve. The method also includes contacting the barrier member with the hand of the individual, the barrier member preventing the hand from exiting the sleeve through the opening before a glove is placed over the opening. The method also includes extending the hand and/or arm through the opening at the distal end of the sleeve after the glove is placed over the opening.

In a fifth aspect, a method of donning a personal protection system. The method also includes providing a protective garment including a sleeve defining a lumen and an opening at a distal end of the sleeve, the lumen configured to receive a hand and/or arm of an individual wearing the protective garment, and a barrier member transitionable from a closed configuration to an open configuration. The method also includes inserting the individual's hand and/or arm into the lumen through a proximal opening of the sleeve while the barrier member is in the closed configuration before a glove is placed over the opening. The method also includes placing a glove over the opening. The method also includes transitioning the barrier member from the closed configuration to the open configuration. The method also includes extending the hand and/or arm through the opening at the distal end of the sleeve and into the glove while maintaining a sterile barrier between the individual and the external environment.

In a sixth aspect, a method of donning a personal protection system. The method also includes providing a protective garment including a sleeve defining a lumen and an opening at a distal end of the sleeve, the lumen configured to receive a hand and/or arm of an individual wearing the protective garment, and a barrier member disposed within the lumen and configured to define an impermeable barrier preventing access to the lumen from an external environment via the opening. The method also includes inserting the hand and/or arm of the individual into the lumen through a proximal opening of the sleeve. The method also includes contacting the barrier member with the hand of the individual, the barrier member preventing the hand from exiting the sleeve through the opening. The method also includes manipulating the barrier member to allow the hand and/or arm to bypass the barrier member. The method also includes extending the hand and/or arm through the opening at the distal end of the sleeve.

In a seventh aspect, a surgical garment for use with a surgical helmet including a ventilation assembly. The surgical garment also includes a front panel, a rear panel, and a hood formed from a surgical fabric. The garment also includes the rear panel including a first portion and a second portion, each of the first and second portions coupled to an opposing side of the front panel, and the first and second portions separable from one another to assist with donning of the surgical garment by a wearer. The garment also includes the hood may include: a front portion and a rear portion, the front portion coupled to the front panel; a first opening defined in the surgical fabric of the hood; a transparent face shield disposed over the first opening, the face shield positioned to be in front of the wearers face when the surgical garment is worn; and where the rear portion of the hood extends below a top edge of the rear panel such that a portion of the hood is disposed between the wearer and the rear panel.

In an eighth aspect, a surgical system also includes a surgical helmet configured to be worn on a wearer's head, the surgical helmet may include: a ventilation system to circulate air about the wearer, at least one coupling member. The system also includes a surgical garment configured to be at least partially disposed over the wearer and the surgical helmet, the surgical garment may include: a surgical fabric, the surgical fabric defining a hood and a body portion; the hood having a front portion and a rear portion, the front portion coupled to the body portion and defining an opening configured to be in front of the wearer's face when disposed over wearer and the surgical helmet, and the rear portion defining a flap detached from the body portion and configured to be at least partially disposed between the wearer and the body portion; a transparent face shield disposed over the opening defined in the hood; and at least one attachment element disposed on the hood and/or transparent face shield, the attachment element for removably coupling the hood to the surgical helmet.

In a ninth aspect, a method of donning a surgical garment over a surgical helmet including a ventilation assembly. The method also includes attaching a transparent face shield of a hood portion of the surgical garment to the surgical helmet by coupling an attachment element on the transparent face shield to a coupling member on the surgical helmet. The method also includes manipulating a surgical fabric of the hood portion of the surgical garment to be disposed over the surgical helmet and head of the wearer. The method also includes manipulating a body portion of the surgical garment to cover a body of the wearer. The method also includes tucking a lower flap that extends from a rear of the hood portion of the surgical garment into the body portion of the surgical garment. The method also includes closing the surgical garment by pulling opposed sides of a rear portion of the body portion of the surgical garment toward one another. The method also includes securing the surgical garment to the wearer by fastening the opposed sides of a rear portion of the body portion adjacent one another.

In a tenth aspect, a surgical garment for use with a surgical helmet including a plurality of coupling members. The surgical garment also includes a shell formed from a fabric. The garment also includes a face shield formed of a flexible and transparent material and including a top portion, a bottom portion, and a sealing perimeter, the shell sealed to the face shield along the sealing perimeter. The garment also includes a pair of lower attachment elements disposed on the bottom portion of the face shield. The garment also includes an upper attachment element disposed on the top portion of the face shield, the upper and lower attachment elements defining three mounting locations at which the face shield is removably mounted to the surgical helmet. The garment also includes where the face shield defines a bounded cut, the bounded cut being disposed between the sealing perimeter and an outer edge of the face shield. The garment also includes where the bounded cut being at least partially disposed between the upper attachment element and the pair of lower attachment elements.

In an eleventh aspect, a surgical garment for use with a surgical helmet including a plurality of coupling members. The surgical garment also includes face shield formed of a flexible and transparent material and including an upper portion and a lower portion. The garment also includes an upper attachment element disposed on the upper portion. The garment also includes a pair of lower attachment elements disposed on the lower portion. The garment also includes where each of the attachment elements are positioned to removably couple with one of the plurality of coupling members of the surgical helmet. The garment also includes a bounded cut defined in the face shield, the bounded cut being at least partially disposed between the upper attachment element and at least one of the pair of lower attachment elements. The garment also includes where the bounded cut being at least partially disposed between the upper attachment element and at least one of the pair of lower attachment elements to mitigate the stress on the face shield when in a flexed state created when each of the attachment element are coupled to one of the plurality of coupling member of the surgical helmet.

Any of the above aspects can be combined in full or in part. Any features of the above aspects can be combined in full or in part. Any of the above implementations for any aspect can be combined with any other aspect. Any of the above implementations can be combined with any other implementation whether for the same aspect or different aspect.

BRIEF DESCRIPTION OF THE DRAWINGS

Referring now to the drawings, exemplary illustrations are shown in detail. Although the drawings represent schematic configurations, the drawings are not necessarily to scale and certain features may be exaggerated to better illustrate and explain an innovative aspect of an illustrative configuration. Further, the exemplary illustrations described herein are not intended to be exhaustive or otherwise limiting or restricting to the precise form and configuration shown in the drawings and disclosed in the following detailed description. Advantages of the present invention will be readily appreciated as the same becomes better understood by reference to the following detailed description when considered in connection with the accompanying drawings.

FIG. 1 is side perspective view of a surgical garment, including a sleeve, donned by a wearer.

FIG. 2 is a partial perspective view of a glove being secured to the sleeve with the sleeve including a barrier member positioned within a lumen of the sleeve, according to one configuration.

DETAILED DESCRIPTION

Figure 3:
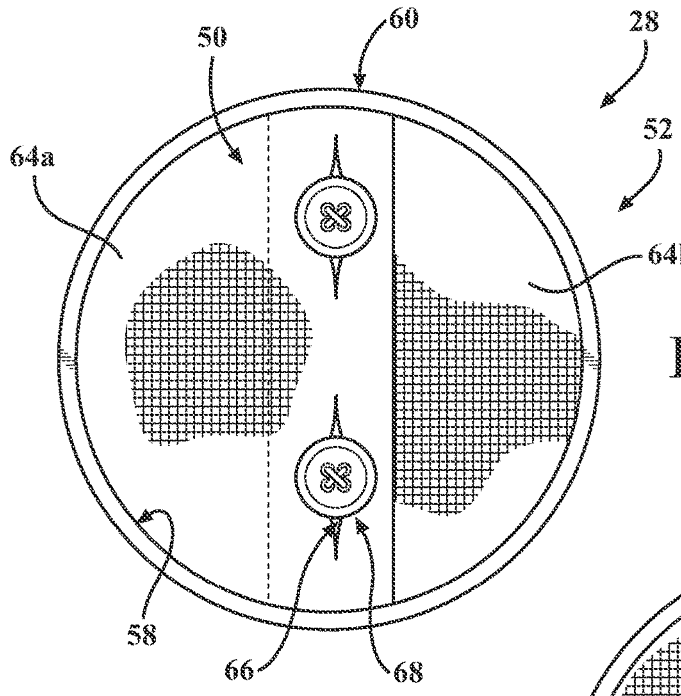
FIG. 3 is a front perspective view of the barrier member including openings and buttons, according to one configuration.

With reference to the drawings, where like numerals are used to designate like structure(s) throughout the several views, an example configuration surgical garment 20 is illustrated in FIGS. 1 and 2. Each configuration is provided by way of explanation of the invention, and not meant as a limitation of the invention. For example, features illustrated or described as part of one configuration may be used with another configuration to yield a related but alternative configuration. Other modifications and variations to the described configurations are also contemplated within the scope and spirit of the invention.

Although as referred herein as a surgical garment 20, the garment may be any type of medical and/or surgical clothing including, but not limited to, drapes, gowns, togas, hoods, coats, protective sleeve(s), and/or coveralls, that defines a sterile barrier between the wearer, typically anon-sterile environment, and the sterile environment, such as the operating room and/or surgical site on the patient. For example, as illustrated in FIG. 1, the surgical garment 20 may comprise a toga configured to cover from a wearer's shoulders down past the knees of the wearer. The surgical garment 20 may be an overhead toga such that the surgical garment 20 must be put over the wearer's head in order to don the surgical garment 20. Additionally, it is contemplated that the surgical garment 20 may not require an overhead donning such that the surgical garment 20 may include a fastener 31, such as a zipper, hook and loop, snaps, or a set of ties, in order to close the surgical garment 20 around the wearer. Moreover, the surgical garment 20 may also include a surgical hood 12 to provide coverage of the head and neck areas. The surgical garment 20 may be a separate hood 12 to be coupled to the toga. It is also contemplated that the surgical hood 12 may be integral with or otherwise attached to the toga, as is illustrated in the Figures. It is further contemplated that the surgical garment 20 may refer to a toga and/or hood used in combination with a surgical helmet 2. As such, the term surgical garment 20 may refer to the toga, hood 12, or similar garment that may also be utilized in combination with a surgical helmet 2 as part of a surgical apparel system 10 or personal protection system.

the surgical garment 20 may include a surgical fabric 14, which may also be referred to as a shell, configured to cover the surgical helmet, explained in more detail below, and at least a portion of the head of the wearer. The surgical garment 20 may be configured as a toga, as illustrated in FIG. 1, the toga including a hood portion 12. It will be understood that a hood 12 may also be used to refer to a surgical garment 120 that covers the head and likely only extends a short distance below the neck when worn by the wearer. However, it is further contemplated that the surgical garment 20 may be configured as a toga, a shirt, or a jacket. It will be understood that a toga 20 refers to a surgical garment 20 that covers the head in the same manner as a hood 12 and extends to at least the waist when worn by the wearer.

The surgical garment 20 may be manufactured from any suitable surgical fabric 14 or combinations of fabrics to help repel and/or absorb water, debris and other contaminants. The surgical fabric 14 may include multiple layers. One such layer may be a microporous film that allows gas to pass through the fabric while still maintaining the microbial barrier.

It is further contemplated that the surgical garment 20 may be constructed of multiple different fabrics coupled to one another to define the barrier. For example, the surgical garment 20 may be primarily constructed from a barrier surgical fabric 14 and a filter fabric 16. The filter fabric 16 may be more permeable, and hence more breathable, than the barrier surgical fabric 14 described above. The filter fabric 16 may be located in an area with a reduced risk of having a microbial particle cross the barrier, such as above the wearer's head or proximate to the crown of the wearer's head, and configured to aid in the circulation of air through the barrier. The barrier surgical fabric 14 may be attached to the filter fabric 16 using any suitable means, such as adhesive, sewing, welding, or a combination thereof.

As illustrated in FIG. 1, the surgical garment 20 may further comprise a face shield 18. The face shield 18 portion of the surgical garment 20 allows the wearer to see through the barrier provided by the surgical garment 20. The face shield 18 is generally a sheet-like structure and may have a thickness of approximately 1 mm or less. The face shield 18 may be mounted and/or attached to an opening or cut-out formed in the surgical fabric 14 of the surgical garment 20, such as in the hood 12. The surgical fabric 14 may be attached around the periphery or edge of the face shield 18 by sewing, snaps, hook and loop, adhesive, welding, or combinations thereof. The face shield 18 may be constructed from a transparent material, such as a polycarbonate. One such polycarbonate is sold under the trademark LEXAN™ by Sabic. The face shield 18 of the surgical garment 12 may also be tinted to protect the wearer's eyes from heightened exposure to bright lights. Furthermore, the face shield 18 may be flexible such that the face shield 18 may be curved to accommodate different head sizes as will be described below.

The surgical garment 20 may also include one or more attachment elements 30 positioned about the surgical garment 20. The attachment elements 30 may also be referred to as a garment fastener. The attachment elements 30, which will be described in greater detail below, are configured to releasably secure the surgical garment 20 to the surgical helmet 2. The attachment elements 30 may take any suitable form, and may comprise metal tacks, rivets, buttons, magnets, hook and loop, snaps, or similar types of fasteners, alone or in combination. The attachment elements 30 may be mounted to the face shield 18 of the surgical garment 20 so as to extend inwardly from the wearer side of the face shield 18. It is also contemplated that the attachment elements 30 may be positioned at any other position or location about the surgical garment 20, including being mounted to the barrier surgical fabric 14 and/or the filtration fabric 16 of the hood 12. The attachment elements 30 may be mounted to the face shield 18 and/or fabric(s) 14/16 via an adhesive, rivet, snap, similar mounting device, or combination thereof.

Referring still to FIGS. 1 and 2, the surgical garment 20 may comprise a garment body 22 including material configured to provide a sterile barrier between the wearer or individual and an external environment 24, such as the operating room or surgical site on the patient. The garment body 22 defines an internal environment 26 shaped to receive and/or at least partially surround the wearer. The garment body 22 is shaped to include features adapting the surgical garment 20 to be worn by a wearer while performing a medical or surgical procedure and/or while in an operating room. The features may include a torso covering section, a back covering section, and/or additional sections configured to cover a portion of the wearer to provide the sterile barrier between the internal environment 26 and the external environment 24.

According to one aspect, the surgical garment 20 and/or the garment body 22 may comprise any type of material. In one example, the material may be woven material. The woven material may be a polyester, cotton, or a polyester-cotton blend. Additionally, it is contemplated that the material may be non-woven material such as fibers or filaments of paper, cotton, polyester, and the like. Moreover, the surgical garment 20 may have a coating or other re-enforcement to provide an additional barrier and/or repel fluids. Typically, the surgical garment 20 is disposable such that the surgical garment 20 is discarded as waste after a single use. However, it is also contemplated that the surgical garment 20 could be a re-usable surgical garment 20 such that the garment is sterilized and re-used for multiple uses.

The surgical garment 20 comprises one or more sleeves 28 extending from the garment body 22. While only one sleeve is illustrated in the figures for the purpose of explanation, it is contemplated that the surgical garment 20 may comprise any number of sleeves 28. For instance, the surgical garment 20 may include a pair of sleeves 28, with each of the sleeves including any of features referred to herein and described in greater detail below. It is contemplated that the sleeve 28(*s*) comprise the same material as the material of the garment body 22.

The sleeve(s) 28 defines a lumen for receiving the hand and/or arm of the wearer, the sleeve including a proximal end 30 and a distal end 32 with the proximal end 30 being coupled to the garment body 22. The sleeve 28 extends distally from the garment body 22 terminating at the distal end 32 of the sleeve 28. Moreover, the sleeve 28 may define a proximal sleeve opening (not shown) at the proximal end 30 where the sleeve 28 couples to the garment body to allow a hand and/or arm of the individual to extend through the lumen defined by the sleeve 28 from the proximal end 30 towards the distal end 32 of the sleeve 28. The sleeve 28 may further define a distal sleeve opening 34 at the distal end 32 of the sleeve 28 to allow the hand of the individual to extend through the distal sleeve opening 34. It is understood that the term "distal" when referring to the sleeve 28 is used to denote features that are closer to the hands of a wearer or individual as differentiated from "proximal," which denote features that are closer to the central body of the individual.

In the exemplary configuration illustrated in FIGS. 1 and 2, the sleeve may further comprise a cuff portion 38. The cuff portion 38 may be disposed at the distal end 32 of the sleeve 28. The cuff portion 38 includes a proximal end 40 and a distal end 42. In the configuration illustrated in FIGS. 1 and 2, the proximal end 40 of the cuff portion 38 may be coupled and/or at least partially surround the distal sleeve opening 34. The cuff portion 38 may be configured to further extend the lumen 36 defined by the sleeve 28 and defines an opening or cuff opening 44 at the distal end 42 of the cuff portion 38. It is contemplated that the cuff portion 38 may define any number of openings. For example, the cuff portion 38 includes a proximal cuff opening and a distal cuff opening. In another example, the cuff opening 44 may include multiple and/or separate openings for the thumb and other fingers to be inserted through.

The cuff portion 38 may also function as an additional means to secure a glove 46 to the sleeve 28 and position the glove over the individual's hand and/or arm. The cuff portion 38 may be considered part of the sterile barrier defined by the garment 20 and/or sleeve 28. As part of donning the surgical garment 20, the cuff portion 38 may be covered with a glove 46 to prevent access from the external environment 24 to the internal environment 26 defined by the garment 20, including the lumen defined by the sleeve 28 and/or the cuff portion via the cuff opening and/or the distal sleeve opening. In such configurations, the glove 46 includes a glove opening 48 configured to overlap a portion of the sleeve 28 and/or cuff portion 38 to provide a continuous sterile barrier between the glove 46 and the sleeve 28.

Various techniques and/or procedures for maintaining a sterile field and/or zone are traditionally observed by medical professionals prior to performing a medical and/or surgical procedure. These procedures typically dictate the medical professionals' movements and/or actions from the time they enter the operating room until they complete the procedure and exit the operating room. These procedures include steps and/or processes for sterilization prior to and for donning the surgical garment 20. Establishing and maintaining the sterile field is important when performing surgical or other procedures to prevent microbial contamination, which can pose a risk of infection or worse for the patient. During the process of donning the surgical garment 20, sterility must be maintained. If the sterile field is compromised during the donning procedure, the whole donning procedure will likely need to be restarted.

As described above, the surgical garment 20 is configured to provide a sterile barrier between a wearer and the external environment 24. The term barrier can be used to refer to an object, device, or material, such as the surgical garment 20, that is us to separate two areas. In the present case, the surgical garment 20 may be placed on the medical professional to define a barrier that separates the medical professional's person from the surrounding environment, i.e. the surgical site and/or patient. The barrier may be used to refer to an impermeable barrier, where the barrier prevents is configured to prevent all reasonable particles and/or contaminates from passing through the barrier. Alternatively, barrier may also mean a semi-permeable barrier, where some elements and/or particles may be able to pass through the barrier, such as air. As such, sterile can be used to refer varying levels of sterilization and/or types of contamination. Sterile when used in combination with barrier may be used to refer to a semi-permeable barrier that prevents the transfer of physical particles, such as biological tissues, fluids, dirt, or the like from passing through the barrier. Alternatively, sterile may be used to define a more or less impermeable barrier, such as one that defines a hermetic type seal and/or barrier that prevents the transfer of smaller particles, such as air or other similar aerosol particles through the barrier.

Unfortunately, it can be challenging to maintain a sterile field or environment while donning one's own surgical garment 20. Therefore, assistance is typically needed to help the individual during the donning procedure. More specifically, an assistant may secure the surgical garment 20 on the individual. As part of the donning procedure, the assistant puts the glove(s) 46 over the distal sleeve opening 34 and/or the cuff opening 44 and onto the individual's hand(s). The individual must typically wait until the glove(s) 46 are placed over the distal sleeve opening 34 and/or the cuff opening 44 before extending their hand and/arm through the sleeve 28 and out of the distal sleeve opening 34 and/or the cuff opening 44 to ensure that the internal environment 26 of the surgical garment 20 is not exposed to the external environment 24, and vice versa. Said differently, to prevent air movement or contamination between the internal environment 26 of the surgical garment 20 and the external environment 24, it is preferrable that the individual's hand not breach the sterile barrier defined by the surgical garment 20 by extending their hand and/or arm through the distal sleeve opening 34 and/or the cuff opening 44 prior to the glove being applied over the opening 34, 44. Using current gowns, while the individual is waiting on the assistant to place the glove(s) 46 over the distal sleeve opening 34 and/or the cuff opening 44, the individual may accidentally slip and/or slide their hand through the distal sleeve opening 34 and/or the cuff opening 44, allowing their hand to break the sterile barrier. Advantageously, the features of the surgical garment 20 described herein allow the individual to don their own surgical garment 20 without contaminating the sterile environment. Additionally, the features of the surgical gown 20 are designed to assist in preventing any accidental exposure between the internal environment 26 on the wearers side of the surgical garment 20 and the external environment 24.

To this effect, as illustrated throughout FIGS. 2-9, exemplary versions of a barrier member 50 are illustrated. The barrier member 50 may be disposed within the lumen 36 defined by the sleeve 28 and be manipulatable between a closed configuration and an open configuration. The barrier member 50, similar to as described above may be used to refer to an impermeable barrier member, where the barrier member 50 may be configured to prevent all reasonable particles and/or contaminates from passing through the barrier when in the closed configuration. Alternatively, the barrier member 50 may also refer to a semi-permeable barrier, the barrier member 50 may be configured to allow elements and/or particles may be able to pass through the barrier, such as air, while still preventing other elements, like the individuals hand or dirt particles, from passing through the barrier member 50 when in the closed configuration. In one exemplary configuration of the barrier member 50, the barrier member 50 may be configured to define a hermetic seal that may prevent all contaminants, such as air, aerosols, the wearers hand, and/or physical particles, from passing through the barrier member 50 when in the closed configuration. For example, the barrier member 50 may be formed from a material that is impermeable to air, aerosols, and/or other infinitely small particles and is sealed by slider, or adhesive such that the barrier member 50 defines a hermetic seal that prevents infinitely small particles from entering or exiting the sleeve through the barrier member 50 when in the closed configuration. The seal may then be opened or broken at the appropriate time to allow wearer's hand to pass by/through the barrier member. Specific examples of such a barrier member 50 will be described in greater detail below.

Alternatively, it is also contemplated that in another configuration exemplary configuration of the barrier member 50, the barrier member 50 may be configured to define a semi-permeable that may prevent some particles, such as air or aerosols to pass through the barrier while preventing other elements such as the wearers hand, dirt, dust, liquid contaminants and/or other physical particles from passing through the barrier member 50 when in the closed configuration. For example, the barrier member 50 may be formed from a material that includes a perforation that can be bypassed by air or comprise a film that is similarly penetrable by air or other aerosols, but still being impermeable to dirt and/or the wearers hand when in the closed configuration.

The barrier member 50 may be disposed within the lumen 36 proximal to the cuff opening 44 defined by the cuff portion 38 and configured to prevent access to the lumen 36 defined by the sleeve 28 from the external environment 24 via the distal sleeve opening 34 when the barrier member 50 is arranged in the closed configuration 52.

In a configuration of the surgical garment that includes the cuff portion 38, the barrier member 50 may be positioned within the lumen 36 defined by the combination of the sleeve 28 and/or cuff portion 38 at an intersection 56 between the distal end 32 of the sleeve 28 and the proximal end 40 of the cuff portion 38. At the intersection 56, the distal sleeve opening 34 meets the proximal end 40 of the cuff portion 38 and opens towards the distal end 42 of the cuff portion 38 and the cuff opening 44. While the barrier member 50 is described as being positioned at an intersection 56 between the distal end 32 of the sleeve 28 and the proximal end 40 of the cuff portion 38, it is contemplated that the barrier member 50 may positioned at any point within the lumen defined by the sleeve 28 and/or cuff portion 38. For example, it is also contemplated that the barrier member 50 may be positioned within portion of the lumen that is defined by the cuff portion 38. For example, the barrier member 50 may be positioned within the lumen defined by the cuff portion 38 proximate the cuff opening 44 such that the barrier member 50, when in the close configuration, covers and/or encloses the cuff opening 44 to prevent access to the lumen 36 defined by the sleeve 28 and cuff portion from the external environment 24 via the cuff opening. In yet another configuration, the barrier member 50 may be positioned at an intermediate point within the lumen defined by the cuff portion 38, such that the barrier member is positioned within the cuff portion at a point between the proximal end 40 and the distal end 42 of the cuff portion 38.

The sleeve 28 defining the lumen includes an interior surface 58 and an exterior surface 60. As described above, the barrier member 50 may be disposed within the lumen defined by the sleeve 28 of the surgical garment 20. Therefore, in some configurations, the barrier member 50 is coupled to the interior surface 58 of the sleeve 28. As referred to herein, the terms "internal" and "interior" refer to the wearer or internal environment side of the surgical garment 20 and the terms "external" refer to the external environment side of the surgical garment 20.

The barrier member 50 is configured to selectively prevent the hand of the individual from extending through the opening. To accomplish this, as described above, the barrier member 50 may be configured to transition between a closed configuration 52 (for example, see FIGS. 3, 4A, 4B, 7A, 8, and 9) and an open configuration 54 (see FIGS. 5, 6, and 7B). In the closed configuration 52, the barrier member 50 defines a barrier between the lumen 36 defined by the sleeve 28 and the external environment 24 through the cuff opening 44 of the cuff portion 38 and/or the distal opening of the sleeve 28. Alternatively, In the open configuration 54, the barrier is broken and the internal environment 26 of the surgical garment 20 is exposed to the external environment via the cuff opening 44 of the cuff portion 38 and/or the distal opening of the sleeve 28. This will be discussed in greater detail below.

The barrier member 50 is configured to be manipulated by in the individual wearing the surgical garment to transition the barrier member 50 from the closed configuration 52 to the open configuration 54. As mentioned above, the barrier member 50 defines the barrier within the sleeve 28 and/or cuff portion 38 that selectively separates the internal environment 26 of the surgical garment 20 and the external environment 24. The barrier member 50 prevents air from exhausting from the internal environment out through the sleeve(s) 28 and into the external environment 24, or vice versa.

The barrier member 50 may comprise a film 62 disposed within the lumen defined by the sleeve 28 and/or cuff portion 38. The film 62 seals the lumen 36 of the sleeve 28 from the external environment 24 and is configured to be breachable by at least a portion of the hand of the individual. The film 62 may be removably coupled to the interior surface 58 of the sleeve 28 and/or the cuff portion 38. It is contemplated that the film 62 may be partially or entirely detachable or removable. Alternatively, the barrier member 50 may constructed from a material, such as the material the sleeve 28 or garment body 22 are constructed from. It is further contemplated that the barrier member may comprise a plurality of pieces of material. The pieces of material may be disposed within the lumen defined by the sleeve 28 and/or cuff portion 38 and removably coupled together by various types of fasteners to that are manipulatable by the individual wearing the surgical garment 20 to transition the barrier member 50 from the closed configuration 52 to the open configuration 54. Exemplary fasteners will be described in greater detail below. The barrier member 50 may include any number of portions 64 of material to form the barrier. For example, referring to FIGS. 3, 4A, and 5-9, the barrier member 50 may comprise a first portion **64*a* and a second portion 64*b*. The first portion 64*a* and the second portion 64*b* may be configured to be joined or coupled together when in the closed configuration 52 and at least partially separated when in the open configuration 54. Alternatively, as illustrated in FIG. 4B, it is contemplated that the barrier member may comprise a plurality of portions 64*a*, 64*b*, 64*c*, 64*d*. While not illustrated in the figures, it is also contemplated that the barrier member 50** may comprise only a single unitary member or piece of material.

Referring FIGS. 3-9, the barrier member 50 includes a manipulatable fastener 68 as a means to selectively transition the barrier member 50 from the closed configuration 52 to the open configuration 54. The manipulatable fastener 68 is configured to be manipulated by the individual to allow a portion of the hand and/or arm of the individual to extend through and/or past the barrier member 50 and out of the opening 34, 44 defined by the sleeve 28 and/or cuff portion 38.

Referring to FIG. 3, in one configuration, the barrier member 50 may comprise a first portion **64*a* and a second portion 64*b* of material that are coupled to opposing sides of the interior surface 58 of the sleeve 28 and/or cuff portion 38. The first portion 64*a* may include any number of barrier openings 66 and the second portion 64*b* may include a corresponding number of fasteners 68 configured to selectively couple with the opening 66 when the barrier is in the closed configuration. For example, as illustrated in FIG. 3, the barrier member 50 may include a first portion 64*a* having two openings 66 and the second portion 64*b* having two corresponding fasteners, such as two buttons 68. After donning of the glove 46 over the opening 34, 44 defined by the sleeve 28 and/or cuff portion 38, the individual may engage the buttons 68 of the barrier member 50 to separate the first potion 64*a* from the second portion 64*b* to transition the barrier member 50 from the closed configuration 52 to the open configuration 54, and allowing the individuals hand to extend past and/or through the barrier member 50. It is contemplated that the barrier openings 66 may be any type of opening varying in size, shape, and dimensions. It is further contemplated that the fasteners 68 may be any type of fastener 68 configured to be easily unfastened via the individual's hand and/or fingers. For example, example, the openings 66 and fasteners 68 may be replaced by snaps, hook and loop, or a similar means of selectively fastening the first and second portions 64***a*, 64*b* of the barrier member 50.

Figure 4A:
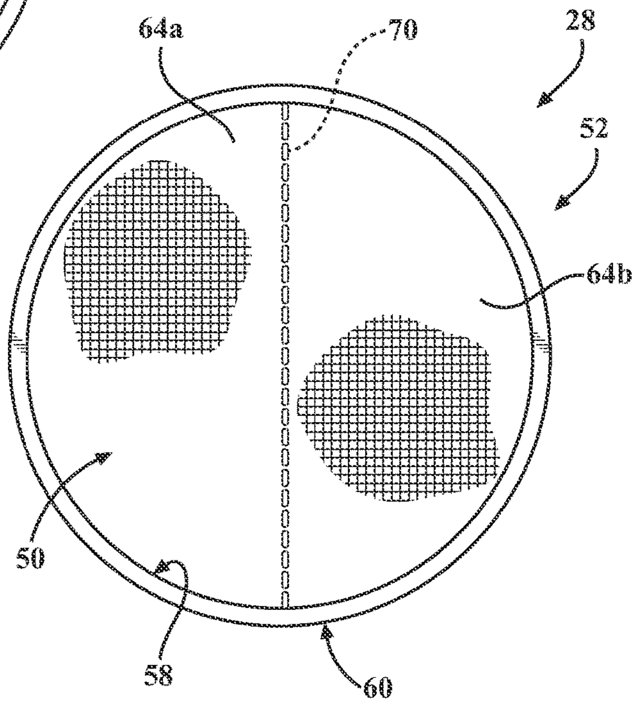
FIGS. 4A-4B are a front perspective view of the barrier member including perforations, according to another configuration.
Figure 4B:
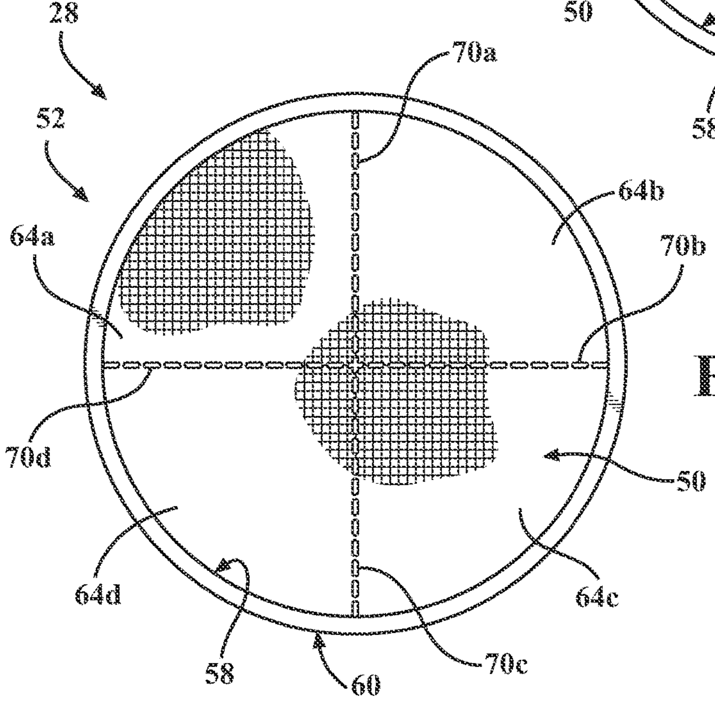

Referring to FIGS. 4A and 4B, in another configuration, the barrier member 50 may include one or more portions of material 64*a*, 64*b*, 64*c*, 64*d* including any number of perforations 70 or frangible connections that may be breakable by the wearer. As shown in FIG. 4A, in one example, the barrier member 50 includes one perforated line 70 extending across the barrier member 50 separating the barrier member into a first portion 64*a* and a second portion 64*b*. Here, the perforated line 70 extends the span of the opening defined either by the cuff portion 38 or the sleeve 28. In another example, as shown in FIG. 4B, the barrier member 50 includes four portions 64*a*, 64*b*, 64*c*, 64*d* delineated by the perforated lines 70*a*, 70*b*, 70*c*, 70*d*. It is contemplated that the perforated lines 70*a*, 70*b*, 70*c*, 70*d* may extend in any direction. It is contemplated that the barrier member may be configured with any number of portions and or perforated lines. After donning of the glove 46 over the opening 34, 44 defined by the sleeve 28 and/or cuff portion 38, the individual may tear or separate the barrier member 50 along the perforated line(s) 70 to transition the barrier member 50 from the closed configuration 52 to the open configuration 54, and allowing the individuals hand to extend past and/or through the barrier member 50. Any combination of tearing or separating of the portions 64*a*, 64*b*, 64*c*, 64*d* is contemplated. For example, the individual may only tear or separate select portions 64*a*, 64*b*, 64*c*, 64*d* of the barrier member 50 along any of the perforated lines 70*a*, 70*b*, 70*c*, 70*d* such that two portions are still joined on one side of the barrier member. It is contemplated that the perforations 70 may be in any shape, orientation and/or configuration. For instance, the perforations 70 may be in a zig-zag configuration or a curved configuration.

Figure 5:
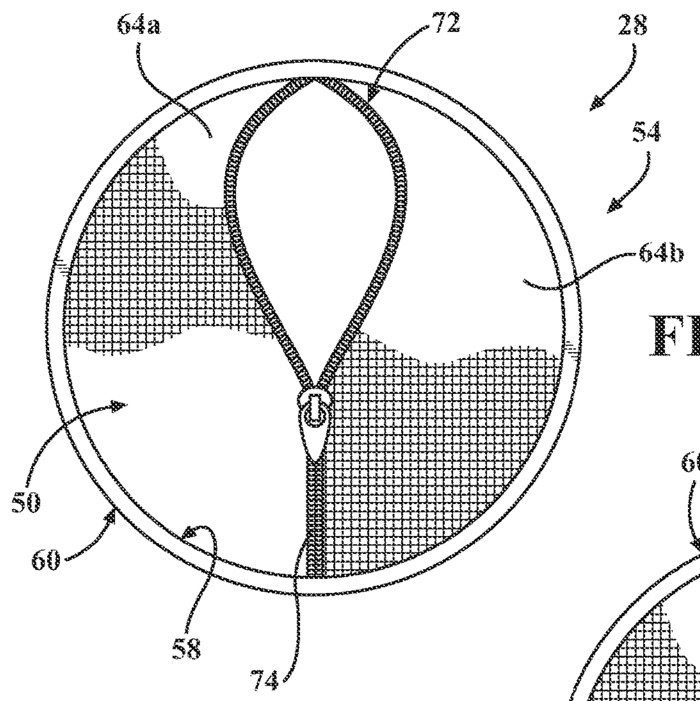
FIG. 5 is a front perspective view of the barrier member including a zipper, according to yet another configuration.

Referring now to FIG. 5, in yet another configuration, the barrier member 50 may comprise a first portion 64*a* and a second portion 64*b* of material coupled to one another by a zipper 72. For example, the barrier member 50 may include a zipper 72 for joining the first potion 64*a* and the second portion 64*b* along a seam 74. After donning of the glove 46 over the opening 34, 44 defined by the sleeve 28 and/or cuff portion 38, the individual may manipulate the zipper 72 to create an opening the first potion 64*a* and the second portion 64*b* along a seam 74 to transition the barrier member 50 from the closed configuration 52 to the open configuration 54, and allowing the individuals hand to extend past and/or through the barrier member 50. Said differently, the barrier member 50 may be unzipped to open the seam 74 and allow the hand and/or arm of the individual to bypass the barrier member 50. It is contemplated that the orientation and position of the zipper 72 may vary. For instance, instead of having the zipper 72 run down the center of the opening, the zipper 72 may run down more to the right side of the opening.

Figure 6:
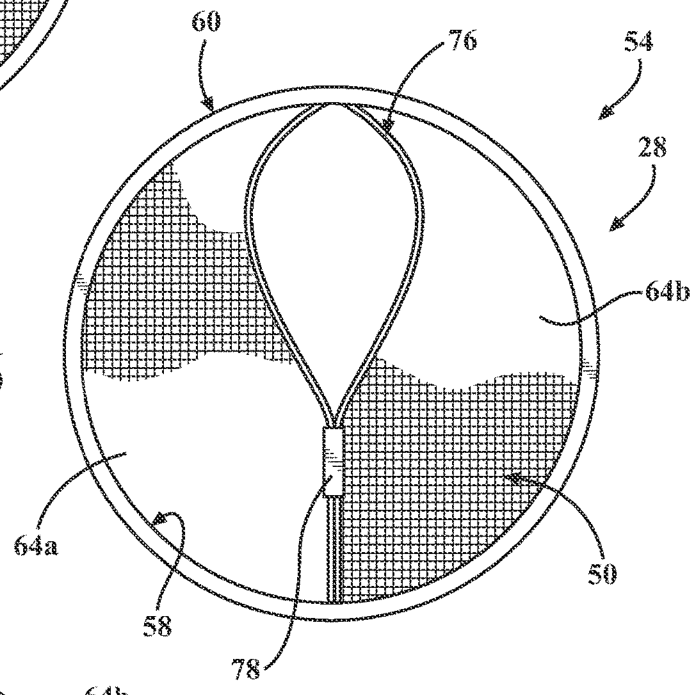
FIG. 6 is a front perspective view of the barrier member including a zip-lock mechanism, according to yet another configuration.

Referring to FIG. 6, in yet another configuration, the barrier member 50 may comprise a first portion 64*a* and a second portion 64*b* of material coupled together by a zip-lock mechanism 76 or a re-sealable mechanism 76. After donning of the glove 46 over the opening 34, 44 defined by the sleeve 28 and/or cuff portion 38, the individual may unseal the barrier member 50 by contacting a sealer 78 to transition the barrier member 50 from the closed configuration 52 to the open configuration 54, and allowing the individuals hand to extend past and/or through the barrier member 50. In a similar fashion as the zipper 72, the zip-lock mechanism 76 may be unsealed to the extent that it allows the individual's hand to extend through. While not shown in the figures, it is also contemplated that the first portion 64*a* and a second portion 64*b* of barrier member 50 may be removably coupled together by one of a magnetic or static electric seal or a spiral-twist seal.

For configurations wherein the surgical garment 20 is reusable, wherein the barrier member 50 comprises a first portion 64*a* and a second portion 64*b* coupled to one another by zipper 72, zip-lock 76, a magnetic or static electric seal, a spiral-twist seal, fasteners 66, 68 or similar re-sealable mechanism, the barrier member 50 may be transitioned from the open configuration 54 back to the closed configuration 52 to be worn again. This way, another individual or the same individual at another time may wear the same surgical garment 20 without concerns of a breached or broken barrier member 50.

Figure 7A:
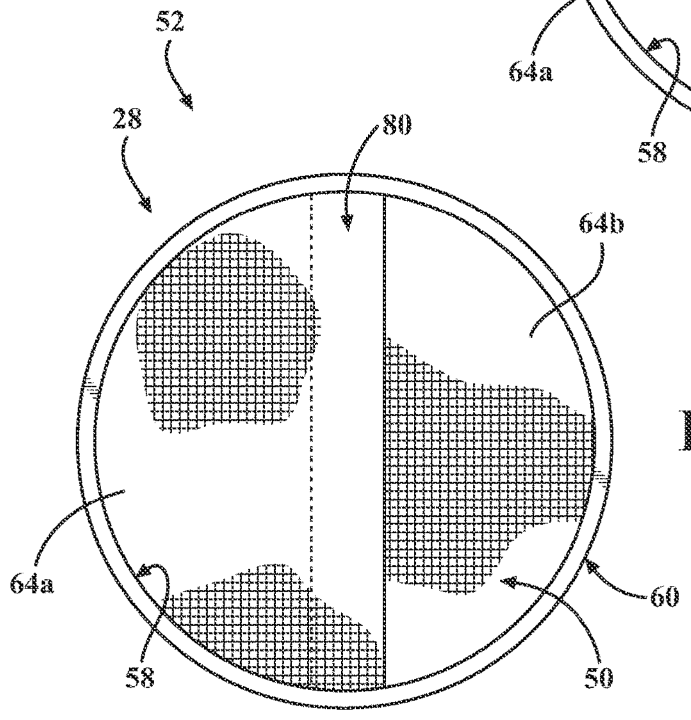
FIGS. 7A-7B are a front perspective view of the barrier member including folds, according to yet another configuration.
Figure 7B:
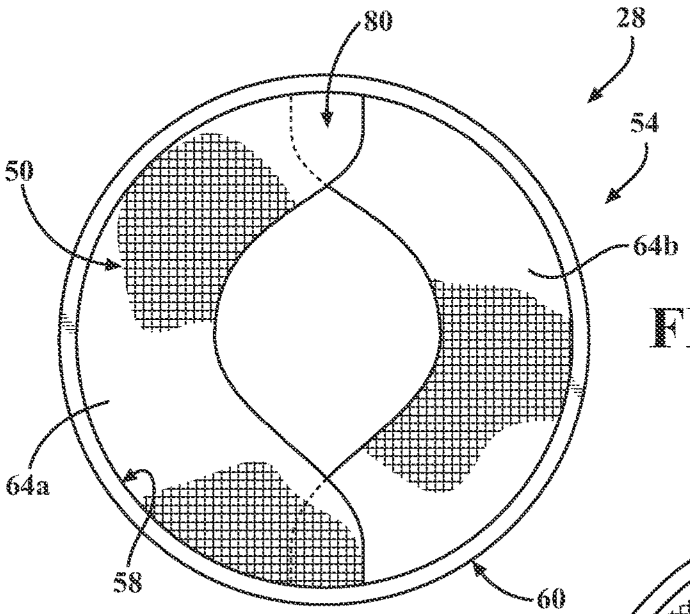

Referring to FIGS. 7A-7B, in yet another configuration, the barrier member 50 may comprise a first portion 64*a* and a second portion 64*b* of material coupled together by overlapping one another along seam 80. More specifically, the first portion 64*a* of the barrier member 50 may include sections or layers that overlap at least one section or layers of the second portion 64*b*. As shown in FIG. 7A, at least a section of the first portion 64*a* extends over a section of the second portion 64*b* defining the seam 80 between the first portion 64*a* and the second portion 64*b* in the closed configuration. In the open configuration, for example, the first and second portions 64*a*, 64*b* are unfolded and/or separated such that they no longer overlap at the seam 80 and instead define an opening. Other configurations are contemplated. For example, the first and second portions 64*a*, 64*b* may be folded such that the plurality of layers overlap, intertwine, and the like at the seam 80. It should be noted that any configuration described above are exemplary and provided for illustration of one hypothetical example, and should not be considered limiting on the scope of the claims.

The barrier member 50 is shown in the closed configuration 52 in FIG. 7A and in the open configuration 54 in FIG. 7B. To transform the barrier member 50 to the open configuration 54, the individual unfolds and separates the first and second portions 64*a*, 64*b* at the seam 80 such that the individuals hand may extend between the first and second portions 64*a*, 64*b* and past and/or through the barrier member 50. Alternatively, or additionally, the individual may maneuver the individual's hand between the plurality of layers folded together at the seam 80 so as to extend through the barrier member 50. It is contemplated that the plurality of layers may be folded in any folding order or dimension at the seam 80 and include any number of folds to contribute to different methods of folding the barrier member 50 of the present invention in its closed configuration 52.

Figure 8:
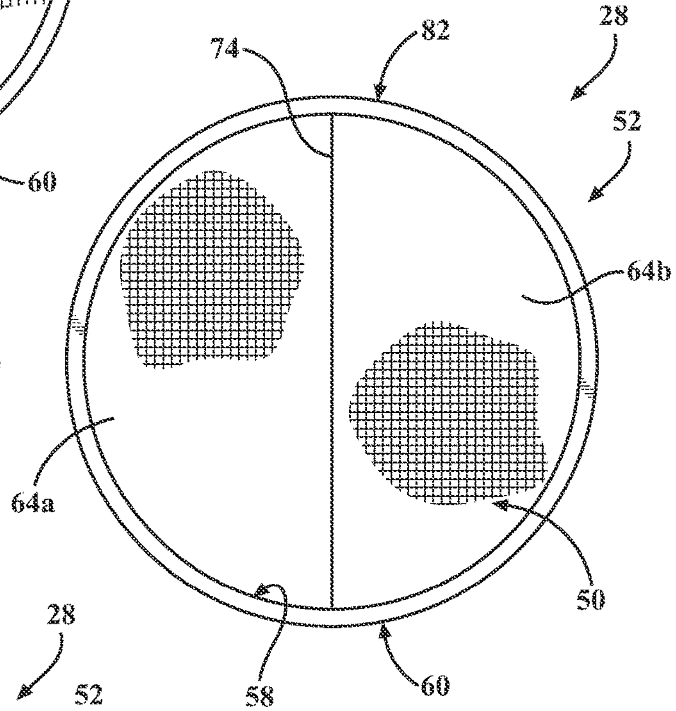
FIG. 8 is a front perspective view of the barrier member including a frangible connection, according to yet another configuration.

Referring to FIG. 8, the barrier member 50 may comprise a first portion 64*a* and a second portion 64*b* of material coupled together by any type of adhesive 82 or sealant to adhere the first portion 64*a* and the second portion 64*b* of the barrier member 50 together. It is contemplated that the adhesive 82 or sealant 82 may adhere to any number of portions. The adhesive 82 may be applied in any manner suitable to define a seal within the lumen of the sleeve 28 and/or cuff portion 38 between the internal environment 26 and the external environment 24. For instance, an adhesive coating or film may be applied along a section or layer of the first and/or second portions 64*a*, 64*b* of the barrier such that the first and second portions 64*a*, 64*b* stick to one another, sealing the lumen 36. After donning of the glove 46 over the opening 34, 44 defined by the sleeve 28 and/or cuff portion 38, the individual may break or unseal the barrier member 50 by separating portions of the barrier member 50 to transition the barrier member 50 from the closed configuration 52 to the open configuration 54, and allowing the individuals hand to extend past and/or through the barrier member 50. In such configurations, the individual may break or unseal the barrier member 50 by applying force. While not illustrated in the figures, it is also contemplated that an adhesive may be used to removably coupled opposing sides of the interior surface 58 of lumen defined by the sleeve 28 and/or cuff portion 38. For example, an adhesive may be applied to the interior surface 58 of the lumen defined by the sleeve 28, and the sleeve may then be pinched together to define a barrier within the lumen defined by the sleeve 28 that selectively prevents the individual wearing the surgical garment 20 from extending their hand through the opening 34, 44 defined by the sleeve 28 and/or cuff portion 38 prior to the glove 46 being placed over the opening 34, 44.

Figure 9:
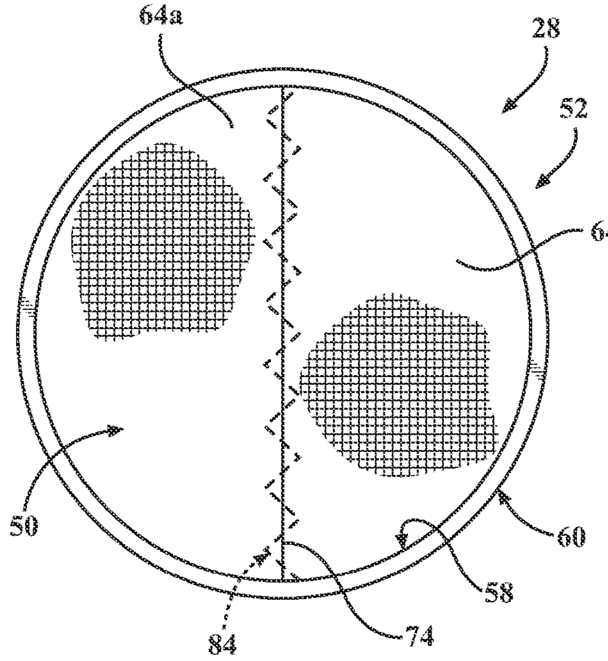
FIG. 9 is a front perspective view of the barrier member including stitching, according to yet another configuration.

Referring to FIG. 9, in yet another configuration, the barrier member 50 may comprise a first portion 64*a* and a second portion 64*b* of material coupled together by stitching 84. More specifically, the first portion 64*a* and the second portion 64*b* may be joined together by stitches or thread. The stitching or thread 84 should be arranged such that the individual wearing the surgical garment 20 is able to remove the stiches and/or break the thread when they are ready to extend past and/or through the barrier member 50. After donning of the glove 46 over the opening 34, 44 defined by the sleeve 28 and/or cuff portion 38, the individual may unstitch the barrier member 50 by separating portions of the barrier member 50 to transition the barrier member 50 from the closed configuration 52 to the open configuration 54, and allowing the individuals hand to extend past and/or through the barrier member 50. It is contemplated that any number of portions may be joined together via one or more operations including coiling, twisting, braiding, weaving, or knitting of material.

In addition to the above-mentioned configurations, it is contemplated that the barrier member 50 that includes the fastener 68 and/or sealing member may include at least one of a zipper, a snap, hook and loop, perforations, adhesives, stitching, and frangible connections. Other variations and/or combinations of the configurations described above are also contemplated. As described above, the fastener and/or sealing member may be arranged on the barrier member 50 in order to define an impermeable and/or a semi-impermeable barrier when in the closed configuration. The sealing member may define a seal between portions of the barrier member 50 such that sealing member is impermeable to infinitely small(er) particles forming a generally hermetic seal when in the closed configuration. Alternatively, the sealing member may be configured such that the seal formed between the portions of the barrier member 50 is semi-impermeable. For example, air may pass through the sealing member and/or barrier member 50, but the sealing member is still impermeable to larger elements and/or objects, such as the wearers hand when in the closed configuration. In either case, the sealing member may be manipulated by the wearer to move the sealing member from a closed or sealed configuration to an open configuration that allows the wearers hand to pass through the barrier member 50.

Further, in some configurations, the sleeve 28 may be transitionable. More specifically, the sleeve 28 may be transition able between the closed configuration 52 and the open configuration 54. The sleeve 28 may be considered as the barrier member 50. In such configurations, the sleeve 28 may include any type of fastener 68 and/or sealing member including features mentioned above. While in other configurations, the sleeve 28 is not considered as the barrier member 50. For example, the sleeve 28 may include a first portion and a second portion with the barrier member 50 configured to couple to the first and second portion to define the barrier.

Moreover, by using any of the aforementioned configurations of the surgical garment 20 along with the disclosed method of manipulating the barrier member 50, the individual can don the surgical gown 20 with limited or no help of an additional person and without the hands of the individual leaving internal environment 26 prior the glove 46 being placed over the opening 34, 44 defined by the sleeve 28 and/or cuff portion 38. Furthermore, depending on the configuration of the barrier member 50, the barrier member 50 may prevent cross contamination between the wearer side and the external environment when the barrier member 50 is in the closed configuration.

In operation, the surgical garment 20 begins in a sterile package. The assistant or wearer may then open the sterile package and don the surgical garment 20. The donning procedure has started. Once the surgical garment 20 has been donned by the wearer, the wear or individual inserts their hand and/or arm into the lumen 36 through the proximal sleeve opening of the sleeve 28 and extends their hand and/or arm through the lumen 36. However, before the individual extends their hand through the distal sleeve opening 34, the gloving procedure must be completed to prevent contamination between the internal environment 26 of the surgical garment 20 and the external environment 24. More specifically, fluids are prevented from being exchanged between the internal environment 26 of the surgical garment 20 and the external environment 24 through the sleeve 28.

To complete the gloving procedure, the glove opening 48 overlaps a portion of the sleeve 28 and/or cuff portion 38 to provide a continuous sterile barrier between the glove 46 and the sleeve 28. In some configurations, an exterior surface 60 of the glove 46 may be flush with the exterior surface 60 of the sleeve 28 to provide the continuous sterile barrier. On the other hand, the glove 46, more specifically, the glove opening 48, may be overlapping the exterior surface 60 of the sleeve 28 such that the exterior surface 60 of the glove 46 is not flush with the exterior surface 60 of the sleeve 28 but still provides the continuous sterile barrier. The glove 46 is configured to cover the opening at the distal end 32 of the sleeve 28 and be at least partially on the exterior surface 60 of the sleeve 28 to form the sterile barrier with the sleeve 28 between the lumen 36 and the external environment 24.

Once the gloving procedure is complete, the individual contacts the barrier member 50 with the hand of the individual and manipulates the barrier member 50 to allow the hand and/or arm to bypass the barrier member 50. Manipulation of the barrier member 50 includes, but is not limited to, separating, tearing, detaching or releasing at least a portion of the barrier member 50 from the interior surface 58 of the sleeve 28 within the lumen 36 to allow the hand and/or arm to bypass, extend through, and/or extend past the barrier member 50 and out of the opening defined by the cuff portion 38. Then, the individual may extend their hand and/or arm into the glove 46 while maintaining the sterile barrier. With this, the donning procedure may be complete with respect to the sleeve 28 and gloving procedure.

Figure 10:
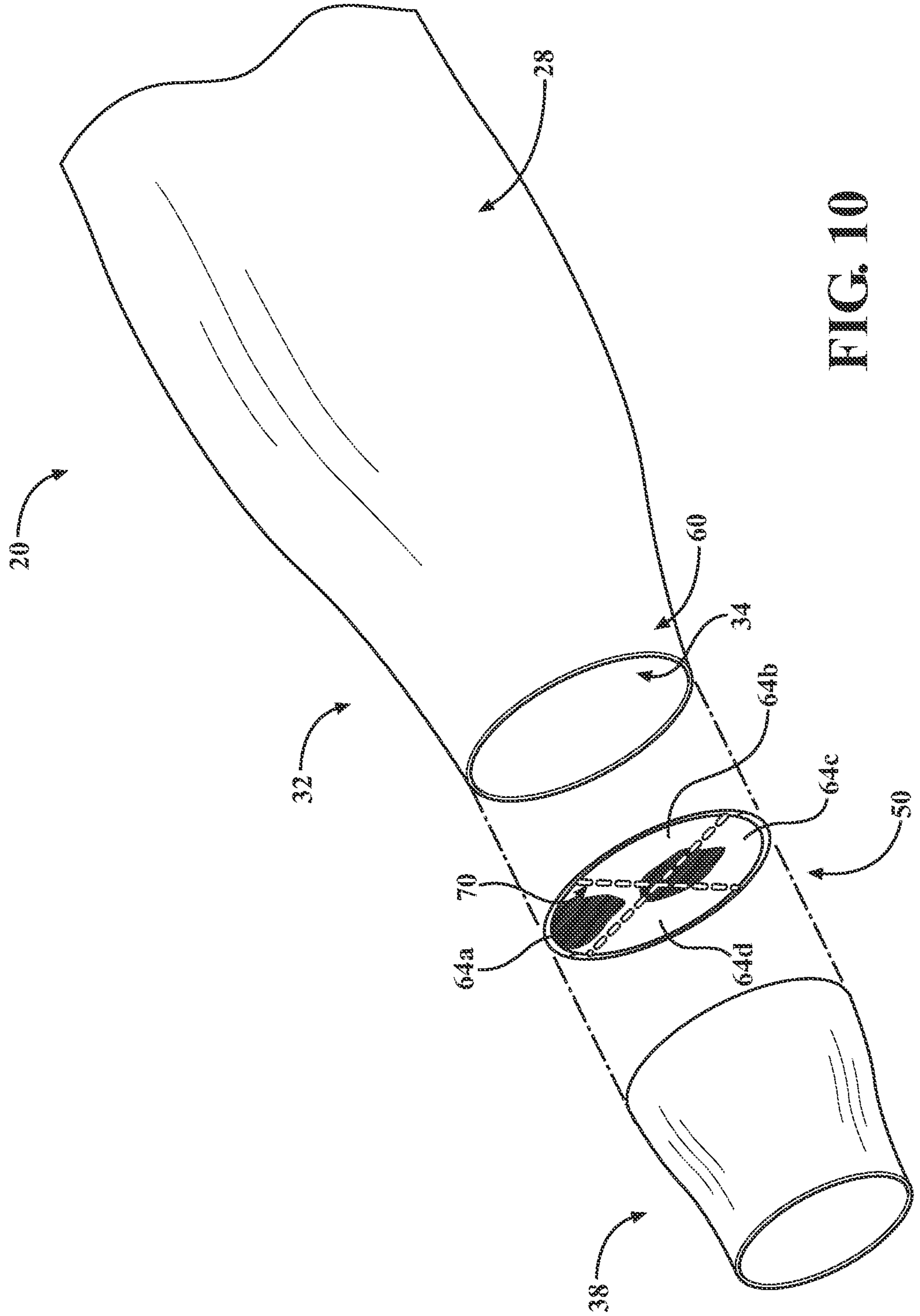
FIG. 10 is a partial exploded view of a sleeve of a surgical garment including a barrier member.

Referring to FIG. 10, a partial exploded view of an example configuration of a sleeve 28 of a surgical garment 20 is illustrated. Similar to the surgical garment 20 described above, the distal end 32 of the sleeve 28 defines an opening 34. A barrier member 50 may be disposed within the opening 34 for the purposed of preventing the wearer from inadvertently inserting their hand through the opening 34 prior to completing the proper steps for donning the surgical 20 while maintaining the proper level of sterility. The barrier member 50 may also be considered and/or defined as being disposed over the opening 34, about the opening 34, enclosing the opening, or the like. The barrier member 50 may be sewn, stitched, adhered to, welded to, or similarly fastened to the sleeve. For example, in the configuration of the surgical garment 20 illustrated in FIG. 10, a perimeter edge of the barrier member 50 may be sewn or stitched to the distal end 32 of the sleeve 28. To sew the barrier member 50 to the sleeve 28, the perimeter edge may be placed to abut an interior or exterior surface 60 of the sleeve proximate the distal end 32 and/or the opening 34, and the sleeve 28 and barrier member 50 may be sewn together.

As illustrated in FIG. 10, the barrier member 50 may include one or more portions of material 64*a*, 64*b*, 64*c*, 64*d* including any number of perforations 70 or frangible connections that may be breakable by the wearer. For example, the barrier member 50 may include one or more perforated lines 70 extending across the barrier member 50 separating the barrier member into a first portion 64*a*, a second portion 64*b*, a third portion 64*c*, and fourth portion 64*d*. The barrier member 50 may formed from a single piece of material, and the perforations may be added and/or cut into the barrier member 50 to allow the barrier member 50 to be broken by the wearer's hand when needed. The perforated line(s) 70 may be configured to extend across a portion of or to span the entire length of the opening 34 defined either by the cuff portion 38 or the sleeve 28. As illustrated in FIG. 10, the four portions 64*a*, 64*b*, 64*c*, 64*d* of the barrier member 50 delineated by the perforated lines 70. It is contemplated that the perforated lines 70 may extend in and/or be oriented in any direction. It is further contemplated that the barrier member 50 may be configured with any number of portions and or perforated lines.

As described above, and as is illustrated in FIG. 10, the surgical garment 20 may also comprises a cuff portion 38. The cuff portion 38 may be disposed at the distal end 32 of the sleeve 28. The cuff portion 38 may be coupled and/or at least partially surround the distal sleeve opening 34. The cuff portion 38 may be configured to be disposed about and/or over the barrier member 50 and/or sleeve opening 34. The cuff portion may be coupled to one of or both of the barrier member 50 and/or sleeve opening 34 via sewing, stitching, adhesive, or a similar fastener. For example, the cuff portion 38 may be positioned to abut the distal end 32 and/or the opening 34 of the sleeve 28 and be sewn to the sleeve 28 and/or barrier member 50.

Figure 11A:
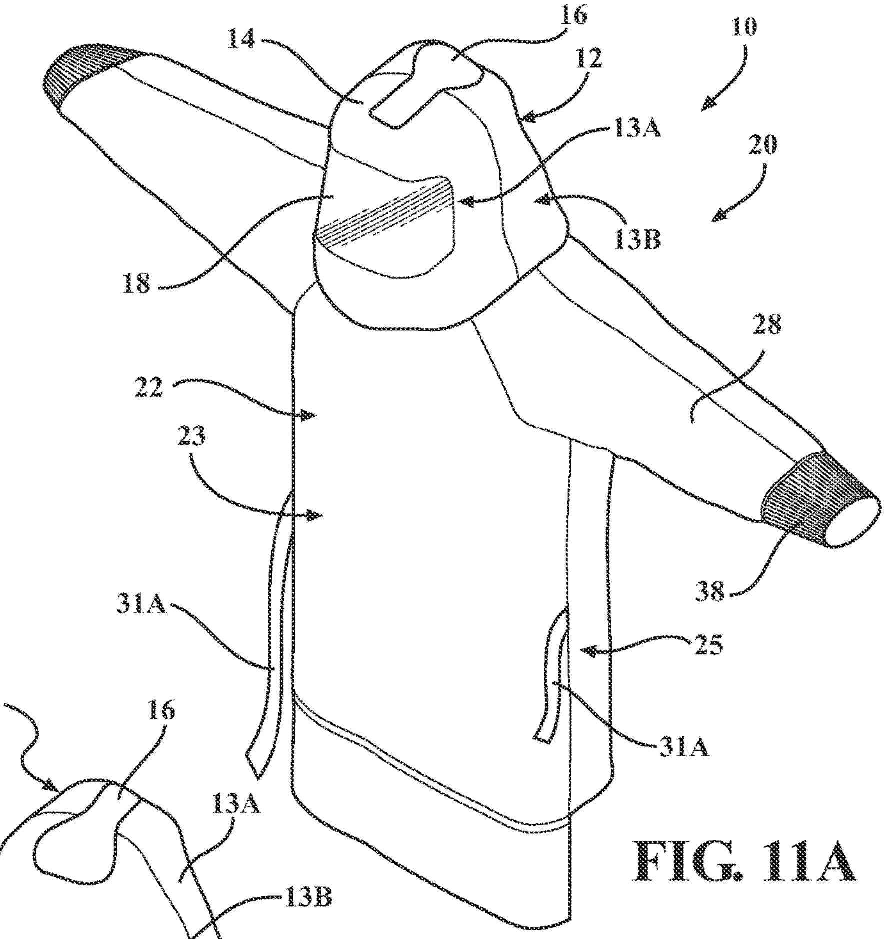
FIG. 11A is a front perspective view of a surgical garment for use with a surgical helmet, the surgical garment including a hood portion and a body portion, the body portion having an open back and the hood portion including a rear flap that is detached from the body portion.
Figure 11B:
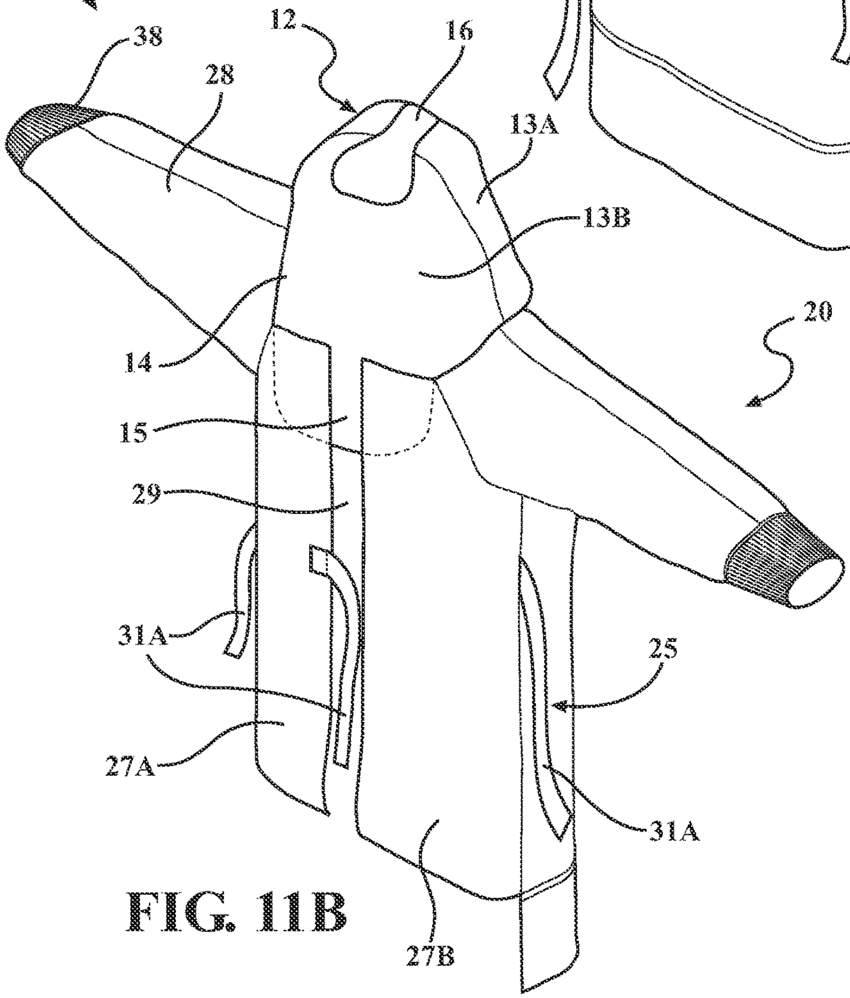
FIG. 11B is a rear perspective of the surgical garment of FIG. 11A.
Figure 11C:
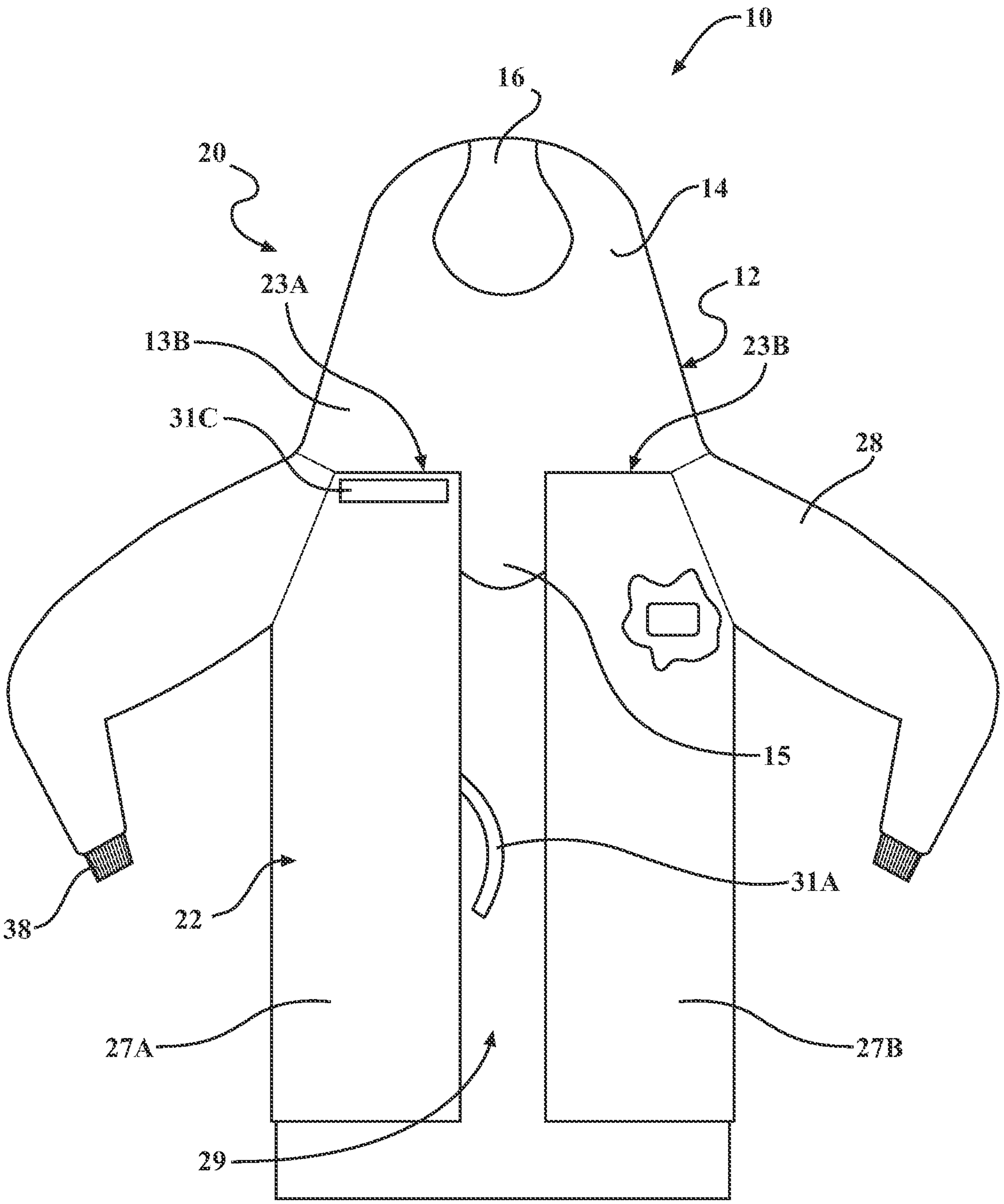
FIG. 11C is a rear view of the surgical garment of FIG. 11A.

Referring to FIGS. 11A-11C, additional views of an example configuration of the surgical garment 20 described above are illustrated highlighting some additional optional features of the surgical garment 20. As illustrated in FIGS. 11A-11C, the surgical garment 20 may be configured as a toga, the toga including a hood 12 and a garment body 22. The hood 12 may also be referred to as a hood portion 22 and the garment body 22 may be referred to as a body portion 22 of the surgical garment 20.

Both the hood 12 and garment body 22 may be formed from any suitable surgical fabric 14 or combinations of fabrics to help repel and/or absorb water, debris and other contaminants. The surgical fabric 14 may include multiple layers. One such layer may be a microporous film that allows gas to pass through the fabric while still maintaining the microbial barrier.

It is further contemplated that the surgical garment 20 may be constructed of multiple different fabrics coupled to one another to define the barrier. For example, the hood 12 may be constructed from a barrier surgical fabric 14 and a filter fabric 16. The filter fabric 16 may be more permeable, and hence more breathable, than the barrier surgical fabric 14 described above. The filter fabric 16 may be located in an area with a reduced risk of having a microbial particle cross the barrier, such as above the wearer's head or proximate to the crown of the wearer's head, and configured to aid in the circulation of air through the barrier. The barrier surgical fabric 14 may be attached to the filter fabric 16 using any suitable means, such as adhesive, sewing, welding, or a combination thereof.

The garment body 22 may comprise a front portion 23 (also referred to as a front panel), a pair of opposed side portions 25 (also referred to as a side panel), and a rear portion 27 (also referred to as a rear panel) coupled the front portion 23 by the opposed side portions 25. The rear portion 27 may be comprise opposed left and right portions 27A, 27B (also referred to as a rear flaps) formed by a slit 29, cut, slot, fissure, or similar opening defined in the rear portion 27 of the garment body 22 to separate the opposed left and right portions 27A, 27B. This slit 29 in the rear portion 27 may be configured to define an opening in the rear portion to allow for easy donning of the surgical garment 20, allowing the rear portion 27 of the garment body 22 to be opened via the slit to allow the user to position the garment body 22 about the wearer. It is further contemplated that the left and right portions 27A, 27B of the rear panel 27 may further comprise a top edge 23A, 23B. The top edge 23A, 23B may extend from sleeve 28 and/or the front portion 23, top edge 23A, 23B configured to be free and otherwise unattached from the garment body 22.

The hood 12 may include a front portion 13A and opposing rear portion 13B. The front portion may define an opening and a shield 18 disposed within the opening, such that the shield is disposed in front of the wearer's face when disposed over the wearer and/or coupled to the surgical helmet 2. When the surgical garment 20 is configured as a toga or surgical gown, as illustrated in FIGS. 11A-11C, the front portion 13A of the hood 12 may be coupled to the garment body 22, and more specifically, may be coupled to the front portion 23 of the garment body 22.

The rear portion 13B of the hood 12 may further comprise a flap 15 extending from the bottom of the hood 12. The flap 15 may detached and/or unattached from the garment body 22, more specifical detached from the rear portion(s) 27A, 27B of the garment body 22. The rear portion 13B and/or the flap 15 being generally detached from the rear portion(s) 27A, 27B of the garment body 22 may improve the donning procedure of the surgical garment 20. For example, as will be described in more detail below, when donning a surgical garment 20 including a hood 12 and garment body 22, the rear portion 13B and/or the flap 15 being detached from the garment body 22 can provide the advantage of making the hood 12 more manipulatable to position the hood 12, and by extension the surgical garment 20, over the wearers head and/or a surgical helmet 2. The flap 15 and rear portion(s) 27A, 27B may be configured such that the flap 15 may be tucked under the rear portion(s) 27A, 27B, and more generally under the garment body 22. This can result in at least a portion of the flap 15 overlapping with and/or being disposed between the garment body 22 (i.e. the rear portion (s) 27A, 27B) and the wearer. The overlap of the flap 15 and the garment body 22 (i.e. the rear portion(s) 27A, 27B) can assist in maintaining a sterile barrier between the wearer and the exterior/surgical environment.

The surgical garment 20 may further optionally include a fastener 31 for securing the surgical garment 20 to the wearer. The fastener 31A may comprise one or more ties coupled to the garment body 22 that are configured to be tied together and/or wrapped around the individual to secure the surgical garment to the wearer. Attentively, the fastener may also comprise a zipper 31B, hook and loop, snaps, buttons and apertures, or similar fastener for connecting the opposed left and right portions 27A, 27B to one another to close the slit 29 and secure the surgical garment to the wearer. It is further contemplated that wherein the flap 15 extending from the hood 12 and the opposed left and right portions 27A, 27B may further comprise fasteners 31C. For example, each of the opposed left and right portions 27A, 27B and the flap 15 of the hood 12 may comprise fasteners 31C arranged to removably couple the flap 15 of the hood 12 to each of the left and right portions 27A, 27B, respectively. The fastener (s) 31C may be is disposed on an outer surface of the flap 15 and on an inner surface of each of the left and right portions 27A, 27B. The fastener(s) 31C may comprise one of snaps, hook and loop, buttons and openings, magnets, or a similar fastening mechanism. Example fasteners and/or means of securing a surgical to a wearer are described in more detail in U.S. Patent Publ. No. 2021/0204621 and related International Patent Publication WO 2019/226810, both of which are incorporated herein by reference in their entirety.

Figure 12A:
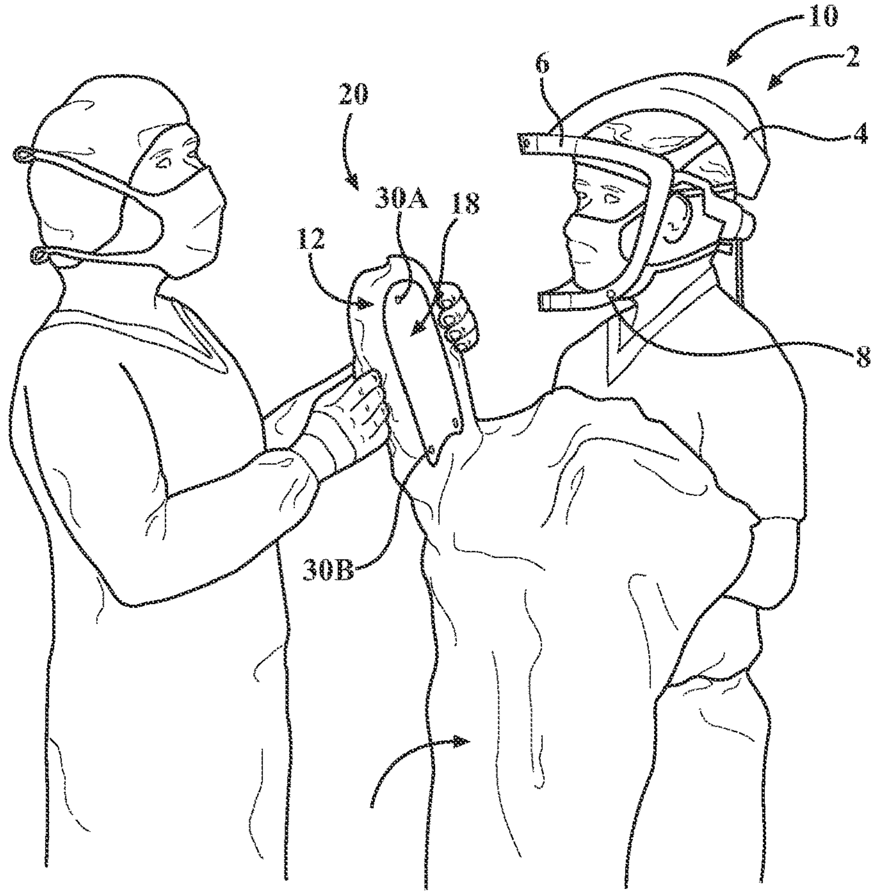
FIG. 12A is a perspective view of a step of donning a surgical garment, the step including preparing the garment to be disposed over a surgical helmet and a wearer.

Referring to FIGS. 12A to 12G, various steps of a method of donning a surgical garment 20 or a surgical apparel assembly 10 including a surgical helmet 2. The surgical garment 20 may include any combination of the features of the surgical garments 20 described above, is illustrated. Referring to FIG. 12A, after the surgical garment 20 has been removed from the packaging, the surgical garment 20 may be lifted to allow the surgical garment 20, and more specifically the garment body 22, to open and/or unfold such that the surgical garment 20 may be donned (i.e. place on) by the wearer.

Figure 12B:
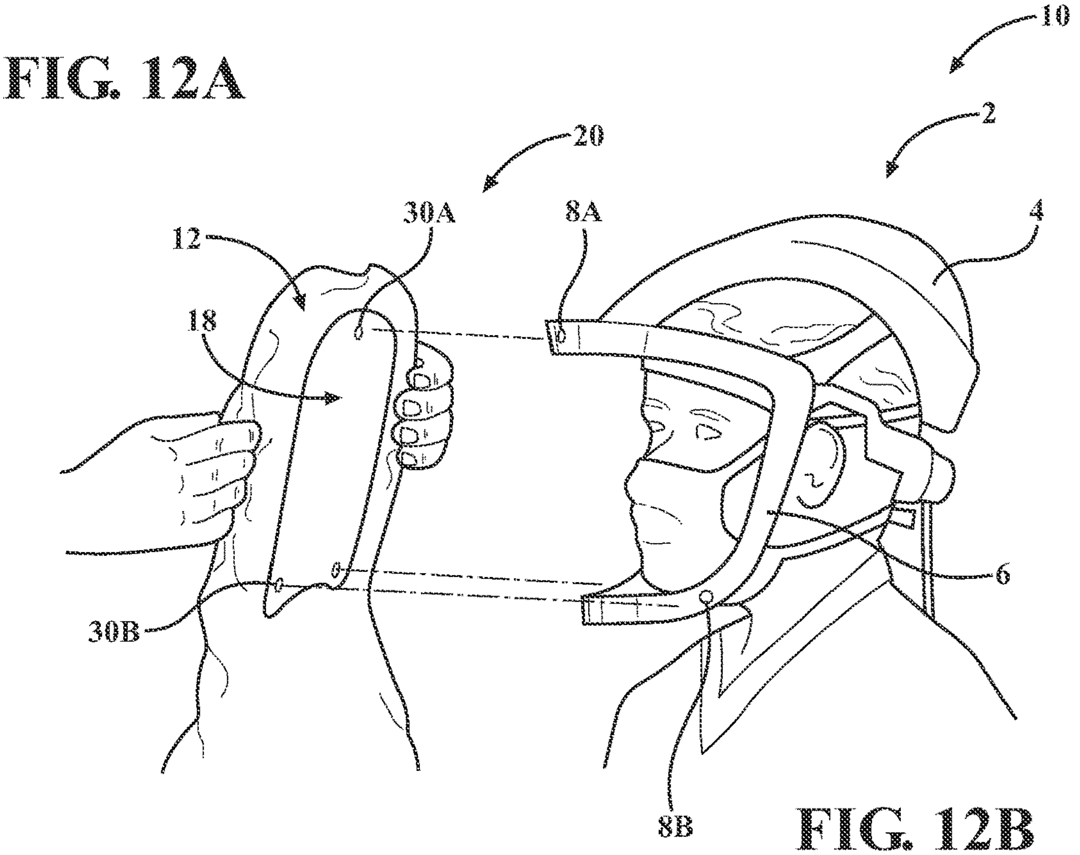
FIG. 12B is a perspective view of a step of donning a surgical garment, the step including coupling the surgical garment to a surgical helmet.

Referring to FIG. 12B, the method of donning a surgical garment 20 may further comprise a step of manipulating the surgical garment 20 and/or positioning the hood 12/transparent face shield 18 relative to the surgical helmet 2 such that the surgical garment 20 may be removably coupled to the surgical helmet 2 via the attachment elements 30 of the surgical garment 20 described above and coupling members 8 of the surgical helmet 2. For example, as illustrated in FIG. 12B, the transparent face shield 18 may comprises a plurality of attachment elements 30A, 30B, and the transparent face shield 18 may be positioned relative to the surgical helmet 2 to removably couple the plurality of attachment elements 30A, 30B to the corresponding coupling members 8A, 8B of the surgical helmet 2. The attachment element(s) 30 may be configured to be constructed of one of a ferromagnetic material or a magnetic material, with the coupling member(s) 8 constructed from the other of a magnetic material or ferromagnetic material such that the pair form a magnetic connection when disposed adjacent to one another, removably coupling the surgical helmet 2 to the surgical garment 20.

Figure 12C:
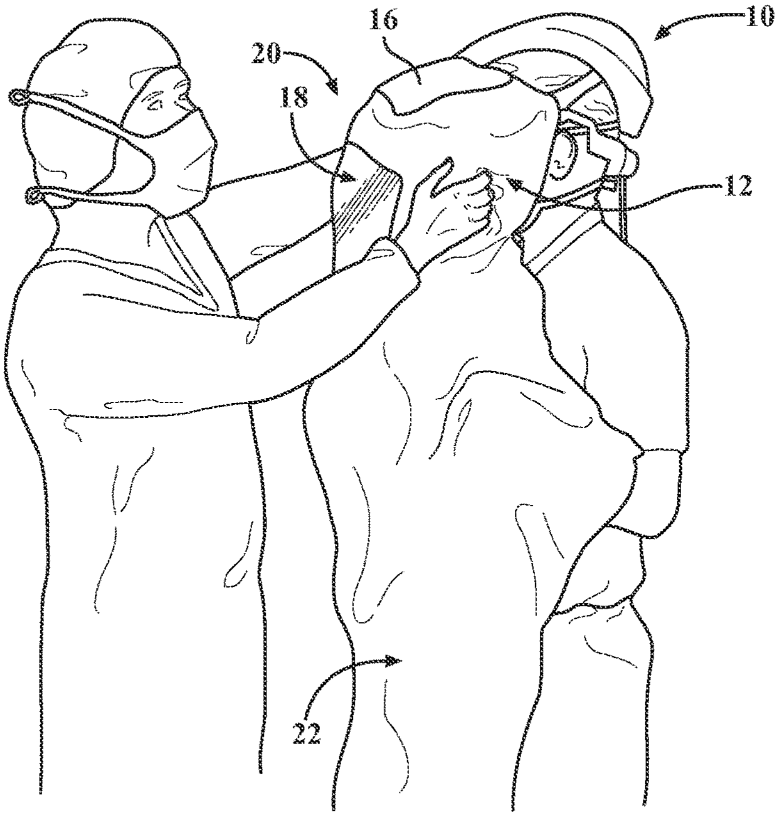
FIG. 12C is a perspective view of a step of donning a surgical garment, the step including manipulating the surgical garment to position a head portion about a surgical helmet and a head of the wearer.

Referring to FIG. 12C, the method of donning a surgical garment 20 may further comprise a step of manipulating the hood 12 of the surgical garment 20 to position the hood over the wearer's head and/or the surgical helmet 2. Using a surgical garment 20 wherein the rear portion 13B and/or the flap 15 of the hood 12 is detached from the garment body 22 may provide greater flexibility and/or rang of movement of the hood 12 in positioning over the wearer's head and/or the surgical helmet 2. This can be particularly true and/or advantageous if a portion of the surgical garment 20 has already been coupled to the surgical helmet 2. For example, wherein the transparent face shield 18 is coupled to the surgical helmet via the attachment elements 30 in the manner described above, the rear portion 13B and/or flap 15 being detached from the body portion 22 of the surgical garment allows for greater range of movement of the hood 12 to positioning it about the wearer's head and the surgical helmet 2.

Figure 12D:
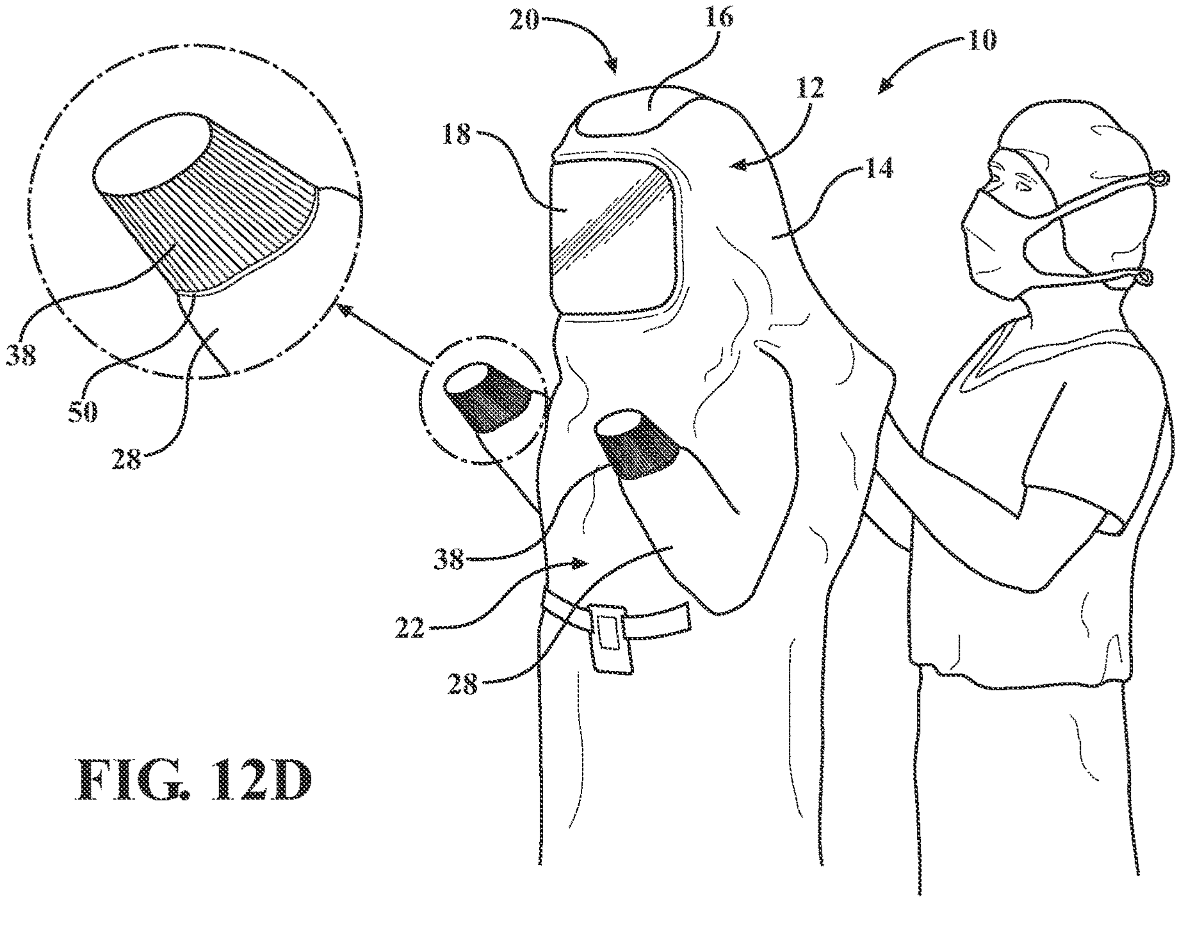
FIG. 12D is a of a perspective view of a step of donning a surgical garment, the step including manipulating a body portion of the surgical garment to be disposed over a body of the wearer.

Referring to FIG. 12D, the method of donning a surgical garment 20 may further comprise a step of manipulating the garment body 22 of the surgical garment to position the surgical garment 20 about the wearer's body. This may include inserting the wearer's hand's and/or arms into the sleeves 28 of the surgical garment 20. As the wearer's hands and/or arms are inserted into the sleeves 28, it is contemplated that the sleeves 28 may further comprise the barrier members 50 described above to contain the hands in the sleeve 28 until the appropriate time. In configurations of the surgical garment 20 including a barrier member 50 in the sleeve(s) 28, the step and method of breaking the barrier member 50 and/or donning the surgical garment may operate in the same fashion as described above.

Figure 12E:
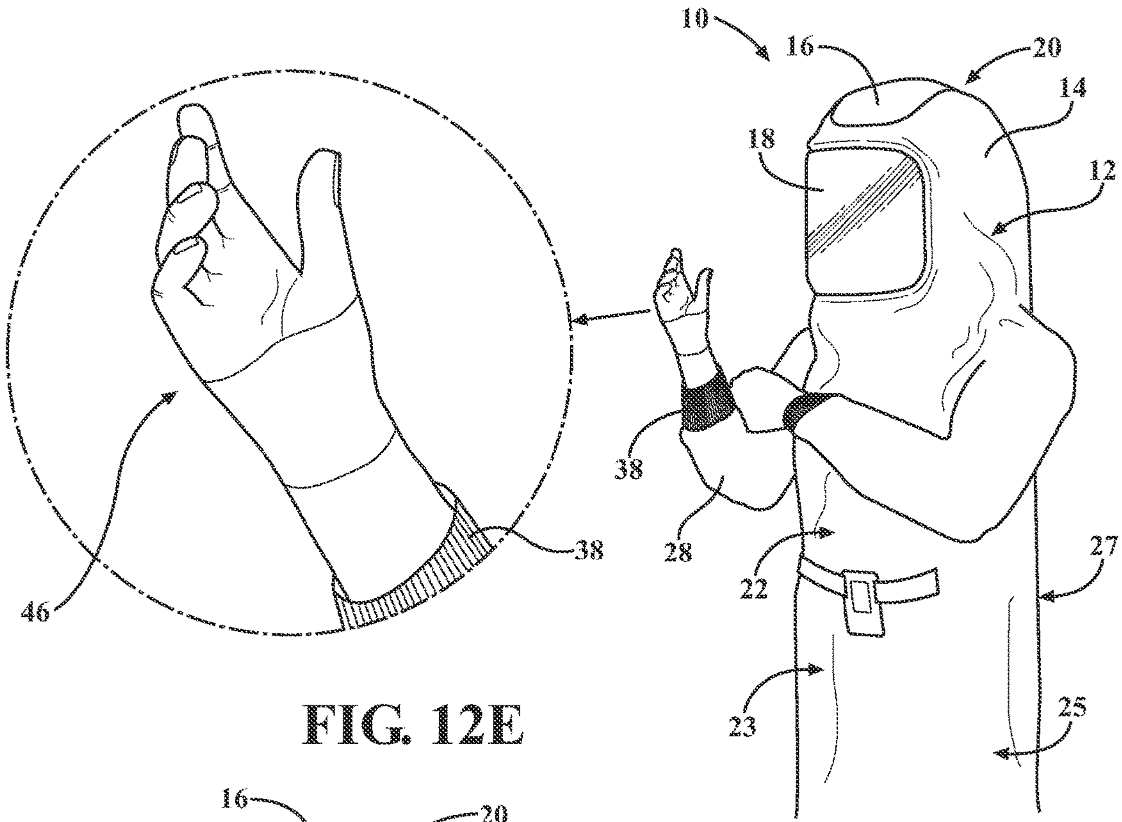
FIG. 12E is a perspective view of a step of donning a surgical garment, the step including inserting a hand of the wearer through a sleeve of the surgical garment and into a glove.

Referring to FIG. 12E, the method of donning a surgical garment 20 may further comprise a step of donning a glove. This step may be performed in the same manner described above with regard to the description of the barrier member 50. For example, while barrier member is still intact, a glove may be place over the opening 34, 44 defined by the sleeve 28 and/or cuff portion 38. After donning of the glove 46 over the opening 34, 44 defined by the sleeve 28 and/or cuff portion 38, the individual may tear or separate the barrier member 50 along the perforated line(s) 70 to transition the barrier member 50 from the closed configuration to the open configuration and allowing the individuals hand to extend past and/or through the barrier member 50.

Figure 12F:
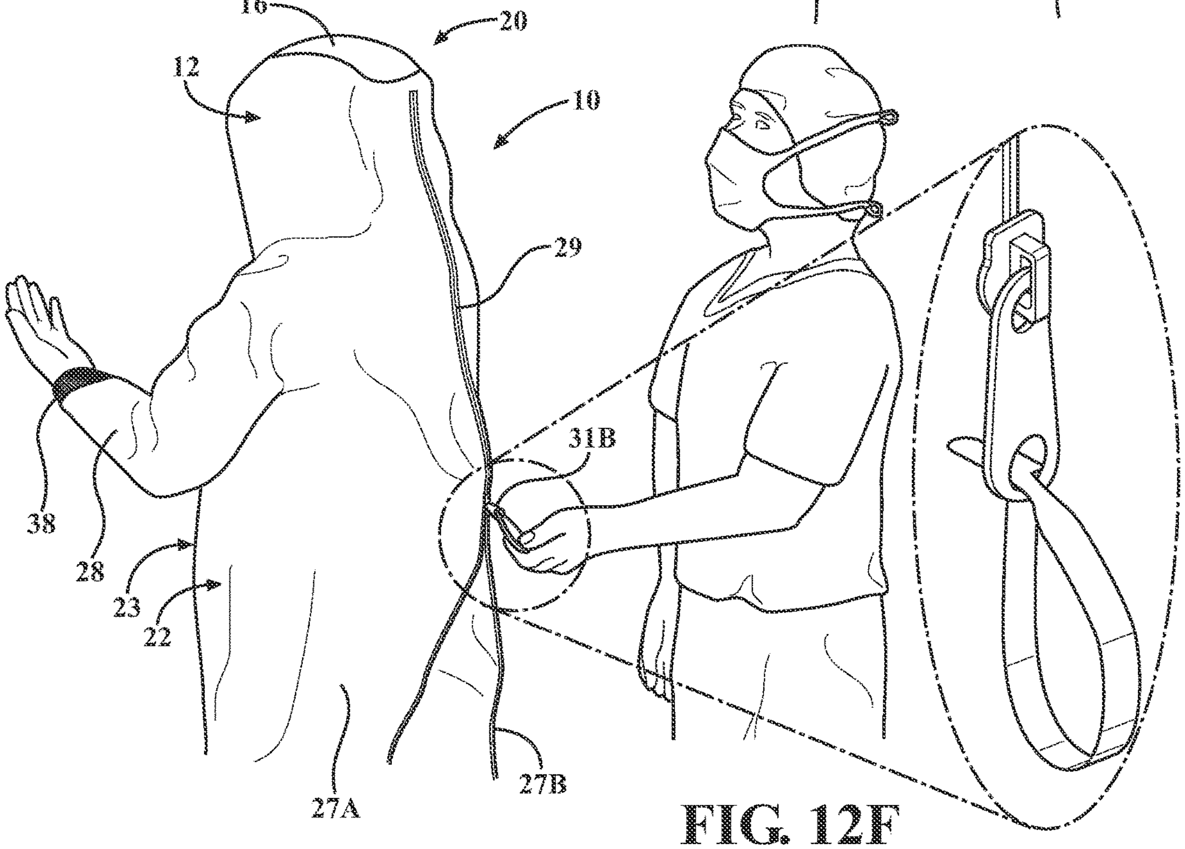
FIG. 12F is a perspective view of a step of donning a surgical garment, the step including closing and/or securing the surgical garment to the wearer via fastening mechanism.

Referring to FIG. 12F, the method of donning a surgical garment 20 may further comprise a step of closing and/or securing the surgical garment 20 to the wearer. For example, as illustrated in the FIG. 12F, the surgical garment 20 may comprise a zipper 31B for closing the slit 29 separating the opposing rear portions 27A, 27B of the garment body. As illustrated in FIG. 12F, the zipper 31B for closing the garment extends from the hood 12 and down through the garment body 22. However, it is also contemplated that the surgical garment 20 may be configured as illustrated in FIGS. 11A-11C, including a rear portion 13B and/or flap 15 that are detached from the garment body 22 of the surgical garment 20. In this configuration, the hood 12 would not include a slit 19 and/or a fastener 31, and the fastener 31, such as the zipper 31B, would only be disposed on the garment body for connecting the opposed rear portion 27A, 27B of the garment body 22.

Figure 12G:
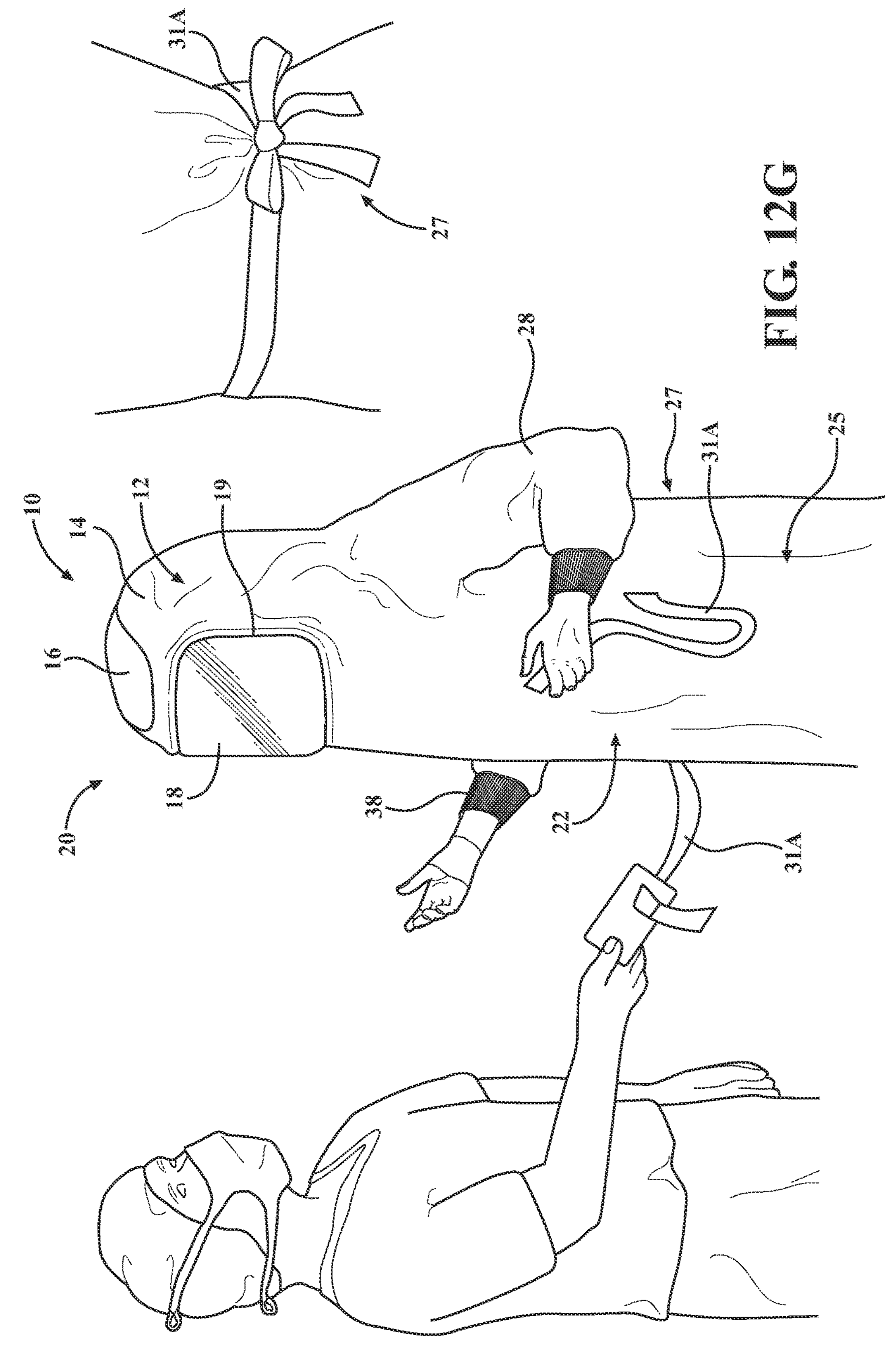
FIG. 12G is a perspective view of a step of donning a surgical garment, the step including closing and/or securing the surgical garment to the wearer via an alternative fastening mechanism to the step illustrated in FIG. 12F.

Referring to FIG. 12G, the method of donning a surgical garment 20 may further comprise a step of step of closing and/or securing the surgical garment 20 to the wearer. For example, as illustrated in the FIG. 12G, the surgical garment 20 may comprise one or more ties 31A for closing the slit 29 separating the opposing rear portions 27A, 27B of the garment body 22. The pair of ties may be coupled to the garment body 22 on opposed sides of the slit 29 separating the opposed rear portions 27A, 27B of the garment body 22 and configured to be tied together to close the gap between the opposed rear portions 27A, 27B of the garment body 22. Alternatively, it is also contemplated that there may only be a single tie 31A, the tie 31A configured to be we wrapped entirely around the wearer of the surgical garment 20, and either tied to itself or include an additional fastening mechanism for securing the tie 31A. For example, the tie 31A may include a hook and loop fastener capable of being secured to a corresponding hook and look fastener on the garment body 22.

Figure 13:
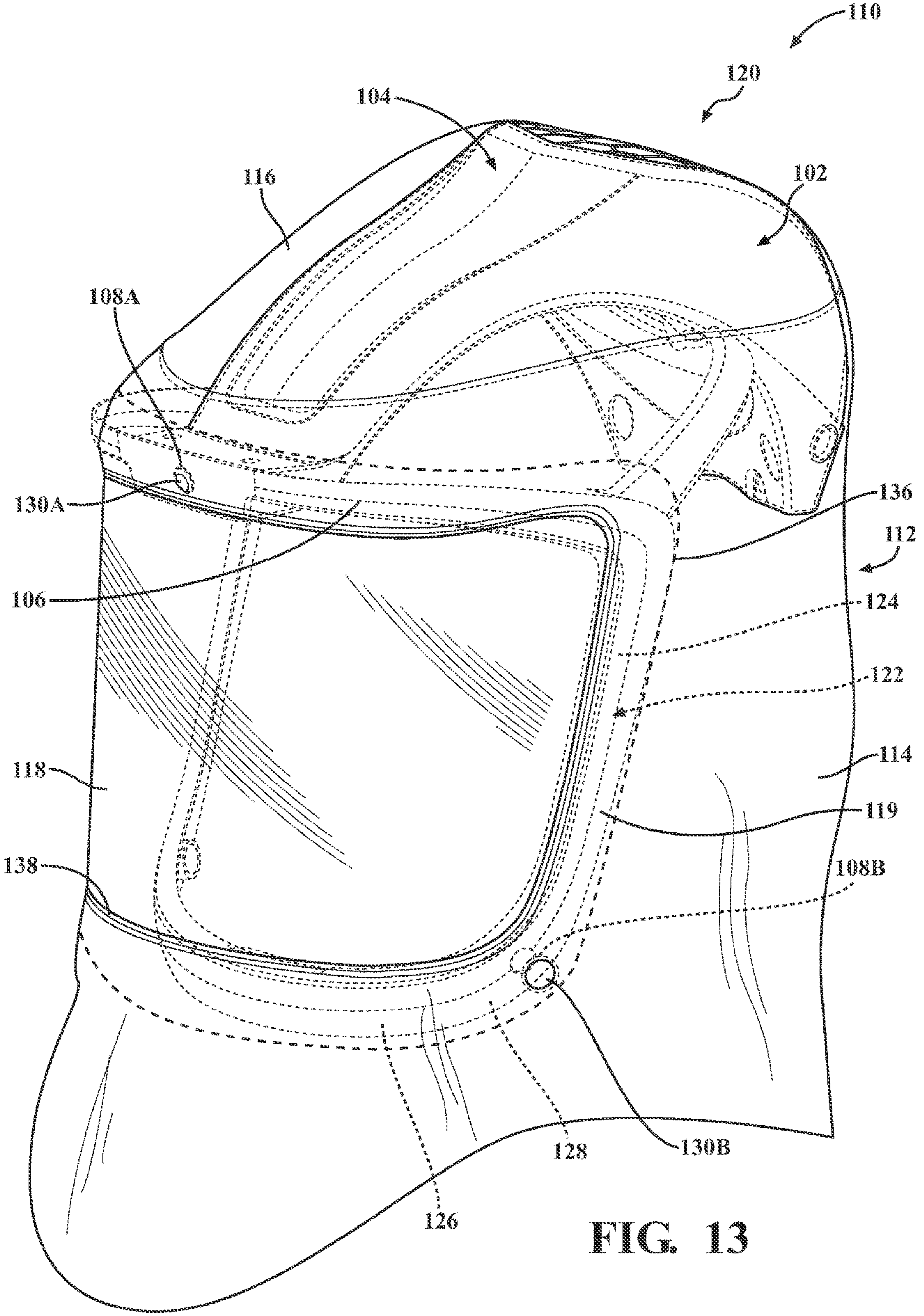
FIG. 13 is a perspective view of a first configuration of a surgical apparel system that includes a surgical garment and a surgical helmet, with the surgical helmet shown in phantom.

Referring again to FIGS. 13 and 14, an example configuration of a surgical apparel system 110 including the surgical garment 120 is illustrated. The surgical apparel system 110 may include a surgical garment 120 configured as a hood 112 and a surgical helmet 102. The surgical garment 120, which may also be referred to as a medical garment, may be configured as a hood or a toga to be placed over the surgical helmet 102. As is illustrated in FIG. 13, the hood 12 or toga may be positioned over the surgical helmet 102 and configured to encompass the surgical helmet 102 and, correspondingly, the head of the person wearing the surgical apparel system 110, thereby covering the wearer's face and back of the head. Alternatively, if the surgical garment 120 were configured as a toga, the toga may be positioned over the surgical helmet 102 and configured to encompass the surgical helmet 102 and, correspondingly, the head, arms, shoulders, and torso of the person wearing the surgical garment 120. To place the surgical garment 120 over the surgical helmet 102, the hood 12 of the surgical garment 120 will typically be turned inside out as the face shield 118 is aligned and affixed to the surgical helmet 102. Once the face shield 118 is positioned relative to the surgical helmet 102, the remainder of the hood 112 will typically be pulled over the wearer's head to cover the exposed components of the surgical helmet 102 and the wearer's head.

The surgical garment 120 and or the hood 112 is configured to provide a barrier, such as a microbial barrier, between the wearer and the surrounding environment. The barrier created by the surgical garment 120 may benefit both the wearer and the patient. The barrier provided by the surgical garment 120 may substantially eliminate the likelihood that the wearer may come into contact with fluid or solid particles of matter from the patient that may be generated during the course of a surgical procedure. The barrier may substantially prevent the transfer of any foreign particles emitted by the wearer from being transferred to the patient during the surgical procedure.

Figure 14:
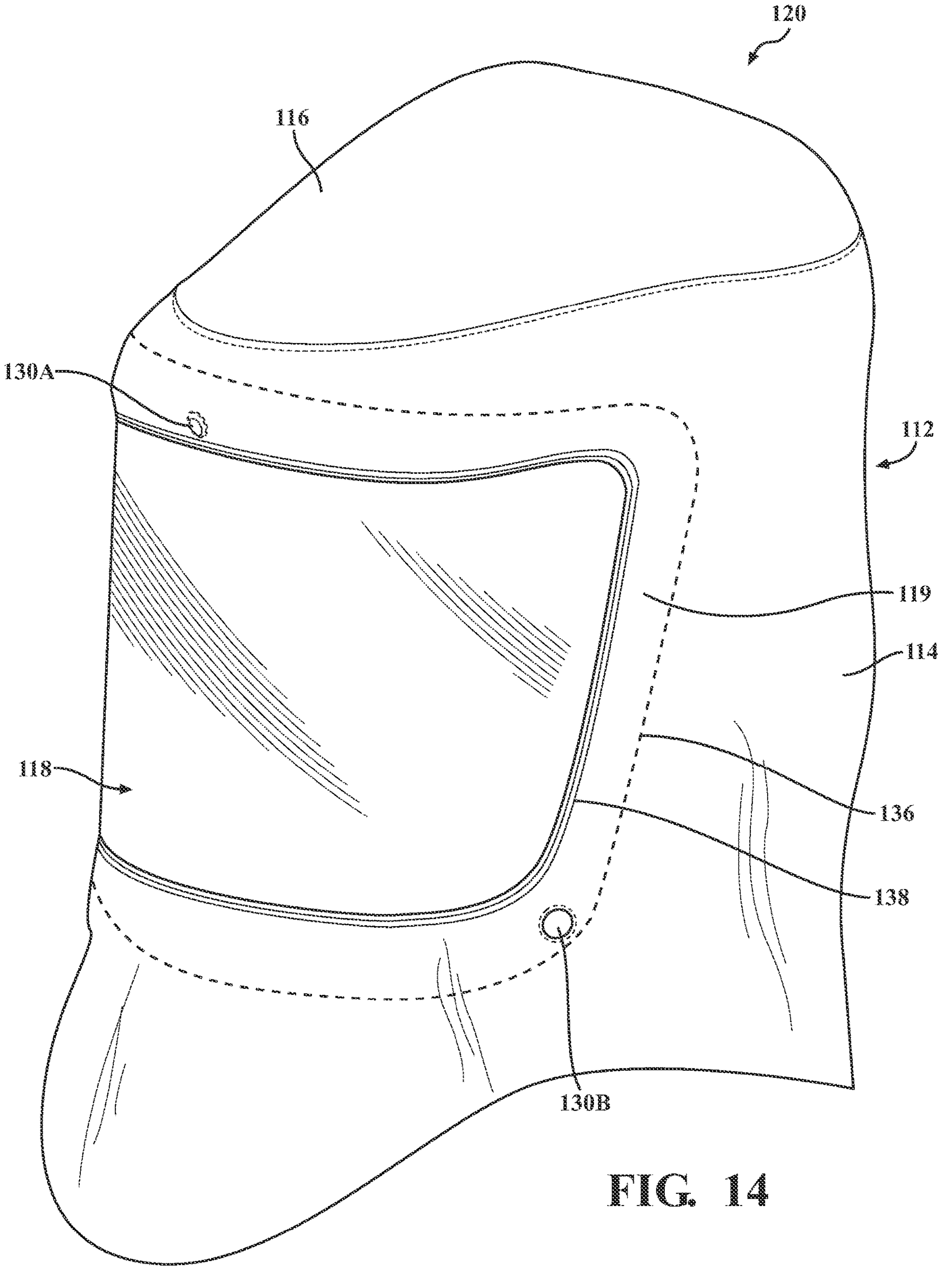
FIG. 14 is a perspective view of the surgical garment of FIG. 13, the surgical garment including a fabric and a face shield.

Referring to FIGS. 13 and 14, the surgical garment 120 may include a surgical fabric 114, which may also be referred to as a shell, configured to cover the surgical helmet 102 and at least a portion of the head of the wearer. The surgical garment 120 may be configured as a hood, as illustrated in FIGS. 13 and 14. It will be understood that a hood refers to a surgical garment 120 that covers the head and likely only extends a short distance below the neck when worn by the wearer. However, it is further contemplated that the surgical garment 120 may be configured as a toga, a shirt, or a jacket. It will be understood that a toga 120 refers to a surgical garment 120 that covers the head in the same manner as a hood and extends to at least the waist when worn by the wearer.

The surgical garment 120 may be manufactured from any suitable surgical fabric 114 or combinations of fabrics to help repel and/or absorb water, debris and other contaminants. The surgical fabric 114 may include multiple layers. One such layer may be a microporous film that allows gas to pass through the fabric while still maintaining the microbial barrier.

It is further contemplated that the surgical garment 120 may be constructed of multiple different fabrics coupled to one another to define the barrier. For example, the surgical garment 120 may be primarily constructed from a barrier surgical fabric 114 and a filter fabric 116. The filter fabric 116 may be more permeable, and hence more breathable, than the barrier surgical fabric 114 described above. The filter fabric 116 may be located in an area with a reduced risk of having a microbial particle cross the barrier, such as above the wearer's head or proximate to the crown of the wearer's head, and configured to aid in the circulation of air through the barrier. The barrier surgical fabric 114 may be attached to the filter fabric 116 using any suitable means, such as adhesive, sewing, welding, or a combination thereof.

As illustrated in FIGS. 13 and 14, the surgical garment 120 may further comprise a face shield 118. The face shield 118 portion of the surgical garment 120 allows the wearer to see through the barrier provided by the surgical garment 120. The face shield 118 is generally a sheet-like structure and may have a thickness of approximately 1 mm or less. The face shield 118 may be mounted and/or attached to an opening or cut-out formed in the surgical fabric 114 of the surgical garment 120. The edge of the opening in surgical fabric 114 may be attached to the face shield 118 by sewing, snaps, hook and loop, adhesive, welding, or combinations thereof. For example, the surgical fabric 114 may be attached to the face shield 118 some distance from the edge of the face shield 118, the location the surgical fabric 114 is attached to the face shield 118 may be referred to as the sealing perimeter 138. The face shield 118 may be constructed from a transparent material, such as a polycarbonate. One such polycarbonate is sold under the trademark LEXAN™ by Sabic. The face shield 118 of the surgical garment 120 may also be tinted to protect the wearer's eyes from heightened exposure to bright lights. Furthermore, the face shield 118 may be flexible such that the face shield 118 may be curved to accommodate different head sizes as will be described below.

The surgical garment 120 may also include one or more attachment elements 130 positioned about the surgical garment 120. The attachment elements 130 may also be referred to as a garment fastener or a second member. The attachment elements 130 are configured to releasably secure the surgical garment 120 to the surgical helmet 102. The attachment elements 130 may take any suitable form, and may comprise metal tacks, rivets, buttons, magnets, hook and loop, snaps, or similar types of fasteners, alone or in combination. As illustrated in FIG. 13, the attachment elements 130 may be mounted to the face shield 118 of the surgical garment 120 so as to extend inwardly from the wearer side of the face shield 118. More specifically, the attachment element 130 may be disposed on the face shield 118 within the perimeter portion of the face shield 118. While not illustrated in the figures, it is also contemplated that the attachment elements 130 may be positioned at any other position or location about the surgical garment 120, including being mounted to the barrier surgical fabric 114 and/or the filtration fabric 116. The attachment elements 130 may be mounted to the face shield 118 and/or fabric(s) 114, 116 via an adhesive, rivet, snap, similar mounting device, or combination thereof.

The surgical helmet 102 further includes a housing 104 positioned above the wearers head. The housing 104 may also be referred to as a shell. The housing 104 may be configured in an arcuate shape to fit over the head of the individual wearing the surgical apparel system 110. Other helmet 102 designs are contemplated. Many portions of the housing 104 may be formed to define voids, or open interior spaces. For example, the housing 104 may comprise a center void. The center void may be located toward the rear of the housing 104. There may be an intake opening or aperture in the top portion of the housing 104 to provide access to the center void. The housing 104 may also be configured to form duct-like structures or passageways within the housing 104 that may be interconnected to the center void.

The surgical helmet 102 may include a face frame 122 coupled to the shell 104 and positioned in front the of the wearers face. The face frame 122 may include a top beam 106 and a chin bar 124, 126. The top beam 106 may be coupled to the front portion of the surgical helmet 102, and the chin bar 124, 126 may extend downwardly from the top beam 106. The chin bar 124, 126 may comprise a pair of post 124 that extend away from the top beam 106. The pair of posts 124 may be coupled to the top beam 106, wherein the top beam 106 is configured to extend across the front of the surgical helmet 102. For example, as illustrated in FIG. 13, the posts 124 may be connected to opposing ends of the top beam 106. The chin bar 124, 126 may be constructed from a generally flexible or pliable material.

The chin bar 124, 126 may further comprise a bottom beam 126 that may extend between the opposed free ends of the posts 124. The chin bar 124, 126 is formed so that the bottom beam 126 is located below and slightly forward of the chin of the person wearing the surgical helmet 102. The bottom beam 126 may be bowed outwardly from the free ends of posts 124. The chin bar 124, 126 may extend outwardly from the top beam 106 such that the chin bar 124, 126 is positioned forward of and generally encircles the face of the wearer when the surgical helmet 102 is secured to the wearer's head. Collectively, the combination of the top beam 106, the posts 124, and the bottom beam 126 may be referred to as the face frame 122, as they generally define an opening positioned in front of the wearer's face when the surgical helmet is positioned on top of the wearer's head.

A plurality of coupling members 108 may be mounted to or dispose on the face frame 122. The coupling members 108 comprise magnetic material and are configured to align and/or attach the face shield 118 of the surgical garment 120 to the surgical helmet 102. Each coupling member 108 may be positioned on the face frame 122 proximate to the opposed posts 124 and/or adjacent opposing ends of the bottom beam 124. Alternatively, the coupling members 108 of the surgical helmet 102 could be arranged or otherwise configured in any suitable way to cooperate with the complementary attachment elements 30 of surgical garment 120 to releasably secure the surgical garment 120 to the surgical helmet 102. For example, as illustrated in FIG. 13, the coupling member(s) 108 may be positioned on the face frame 122 at opposing ends of the lower beam 126 proximate where each of the posts 124 connects to the lower beam 126. The coupling member(s) 108 may also be disposed on the upper beam 106 of the face frame 122. The surgical helmet 102 and/or the face frame 122 may be configured to have any number of coupling members 108. For example, he surgical helmet 102 may utilize two coupling members 108. Alternatively, it is also contemplated that the surgical helmet 102 may be configured such that the face frame 122 comprises a single coupling member 108 or, in other configurations, three or more coupling members 108 may be spaced about the chin bar 124, 126 and/or top beam 106. It is contemplated that other types of coupling members 108 may be used in place of and/or in addition to those comprising magnetic materials, such as with a hook and loop fasteners, snaps, coupling members comprising ferromagnetic material, or similar type fasteners. Other configurations are contemplated.

Referring to FIGS. 15A to 19D, various configurations of a face shield 118A, 118B, 118C, 118D, 118E of the surgical garment 120 described above are illustrated. Each configuration of the face shield 118A, 118B, 118C, 118D, 118E may generally comprise a perimeter edge 136, and define a sealing perimeter 138 spaced inward a distance from the perimeter edge 136. The sealing perimeter 138 identifying the location where the surgical fabric 114 may be coupled to the face shield 118A, 118B, 118C, 118D, 118E. Each configuration of the face shield 118A, 118B, 118C, 118D, 118E may also comprise one or more attachment elements 130 for removably securing the surgical garment 120 to a surgical helmet 102, as described above. Each configuration of the face shield 118A, 118B, 118C, 118D, 118E may comprise at least one upper attachment element 130A disposed on an upper portion 146 of the face shield and at least one lower attachment element 130B, 130C disposed on the lower portion 148 of the face shield 118A, 118B, 118C, 118D, 118E. The upper and lower portions 146, 148 of the face shield 118A, 118B, 118C, 118D, 118E may defined by an imaginary line 150 that extends longitudinally across the length of the face shield 118A, 118B, 118C, 118D, 118E. Example attachment elements 130 for coupling a surgical garment to a surgical helmet are described in more detail in U.S. Pat. No. 10,750,800 and related International Patent Publication WO 2019/147923, both of which are incorporated herein by reference in their entirety.

The face shield 118A, 118B, 118C, 118D, 118E also define a recess 140 or ident in the perimeter edge 136 of the face shield 118A, 118B, 118C, 118D, 118E. The recess 140 may be utilized to properly orient the face shield 118A, 118B, 118C, 118 118D, 118E during assembly with the surgical fabric 114. Alternatively, the face shield 118A, 118B, 118C, 118D, 118E may be utilized in manufacturing of the face shield 118A, 118B, 118C, 118D, 118E. For example, the recess 140 may be utilized to identify the top portion of the face shield 118A, 118B, 118C, 118D, 118E relative to the bottom portion of the face shield 118A, 118B, 118C, 118D, 118E and/or a right portion of the face shield 118A, 118B, 118C, 118D, 118E relative to the left portion of the face shield 118A, 118B, 118C, 118D, 118E. Properly orienting the face shield 118A, 118B, 118C, 118D, 118E during manufacturing and/or assembly of the face shield 118A, 118B, 118C, 118D, 118E can assist with correctly installing the one or more attachment elements 130 in the appropriate position and in the appropriate direction relative to the surfaces of the face shield 118A, 118B, 118C, 118D, 118E.

The face shield 118A, 118B, 118C, 118D, 118E may also further comprise a bounded cut 144 defining an opening in the face shield 118A, 118B, 118C, 118D, 118E. The bounded cut 142A, 142B, 142C, 142D, 142E may be configured as a cut that extends a distance or length across the face shield 118A between opposed terminal ends 144A, 144B, 144C, 144D, 144E. The bounded cut 142A, 142B, 142C, 142D, 142E may define an opening in the face shield 118A, 118B, 118C, 118D, 118E having a general width or thickness of D1. The width or thickness of the bounded cut 142A, 142B, 142C, 142D, 142E may be any dimension that provides stress and/or strain relief when the face shield 118A, 118B, 118C, 118D, 118E is flexed or bent, as will be described in greater detail below.

The bounded cut 142A, 142B, 142C, 142D, 142E may positioned on the face shield 118A, 118B, 118C, 118D, 118E between the perimeter edge 136 of the face shield 118A, 118B, 118C, 118D, 118E and the sealing perimeter of the face shield 118A, 118B, 118C, 118D, 118E. The bounded cut 142A, 142B, 142C, 142D, 142E may also positioned on the face shield 118A, 118B, 118C, 118D, 118E such that the between the bounded cut 142A, 142B, 142C, 142D, 142E is located between the attachment 130 and the sealing perimeter of the face shield 118A, 118B, 118C, 118D, 118E. For example, as illustrated in FIGS. 15A to 19D, the bounded cut 142A, 142B, 142C, 142D, 142E is located between the attachment 130 and the sealing perimeter of the face shield 118A, 118B, 118C, 118D, 118E such the bounded cut 142A, 142B, 142C, 142D, 142E separates an attachment element 130A disposed on an upper portion 146 of the face shield 118A, 118B, 118C, 118D, 118E from the sealing perimeter 138. It is further contemplated that the bounded cut 142A, 142B, 142C, 142D, 142E may be positioned on the face shield 118A, 118B, 118C, 118D, 118E such the bounded cut 142A, 142B, 142C, 142D, 142E separates the upper attachment element 130A from one or more lower attachment element(s) 130B, 130C on the lower portion 148 of the face shield 118A, 118B, 118C, 118D, 118E. The upper and lower portions 146, 148 of the face shield 118A, 118B, 118C, 118D, 118E defined by an imaginary line 150. For example, as illustrated in FIGS. 15A to 19D, the bounded cut 142A, 142B, 142C, 142D, 142E is located between the upper attachment 130 and the pair of lower attachment elements 130 of the face shield 118A, 118B, 118C, 118D, 118E. In operation, placing the bounded cut 142A, 142B, 142C, 142D, 142E between the attachment 130 and the sealing perimeter 138 and/or the upper attachment 130 and the pair of lower attachment elements 130 of the face shield 118A, 118B, 118C, 118D, 118E can provide stress and/or strain relief across the surface of the face shield 118A, 118B, 118C, 118D, 118E when the face shield 118A, 118B, 118C, 118D, 118E is flexed or bent to be attached to the surgical helmet 102.

While only a single bounded cut 142A, 142B, 142C, 142D, 142E is shown in the configurations of the face shield 118A, 118B, 118C, 118D, 118E illustrated in FIGS. 15A-19D, it is contemplated that the face shield 118 may include more than one bounded cut 142. Any additional bounded cut(s) 142 should be located on the face shield 118 between the perimeter edge 136 of the face shield 118 and the sealing perimeter 138 to maintain sterility of the surgical garment 12 and not create and exposed opening in the face shield 118 that is not covered by the surgical fabric 114 that could potentially allow debris or other items to bass through the surgical garment 120. Furthermore, any additional bounded cut(s) 142 may positioned on the face shield 118 relative to the upper and lower attachment elements 130, and or relative to the left and right attachment elements 130 such that the bounded cut(s) 142 provide stress and/or strain relief when the face shield 118 is flexed or bent.

Figure 15A:
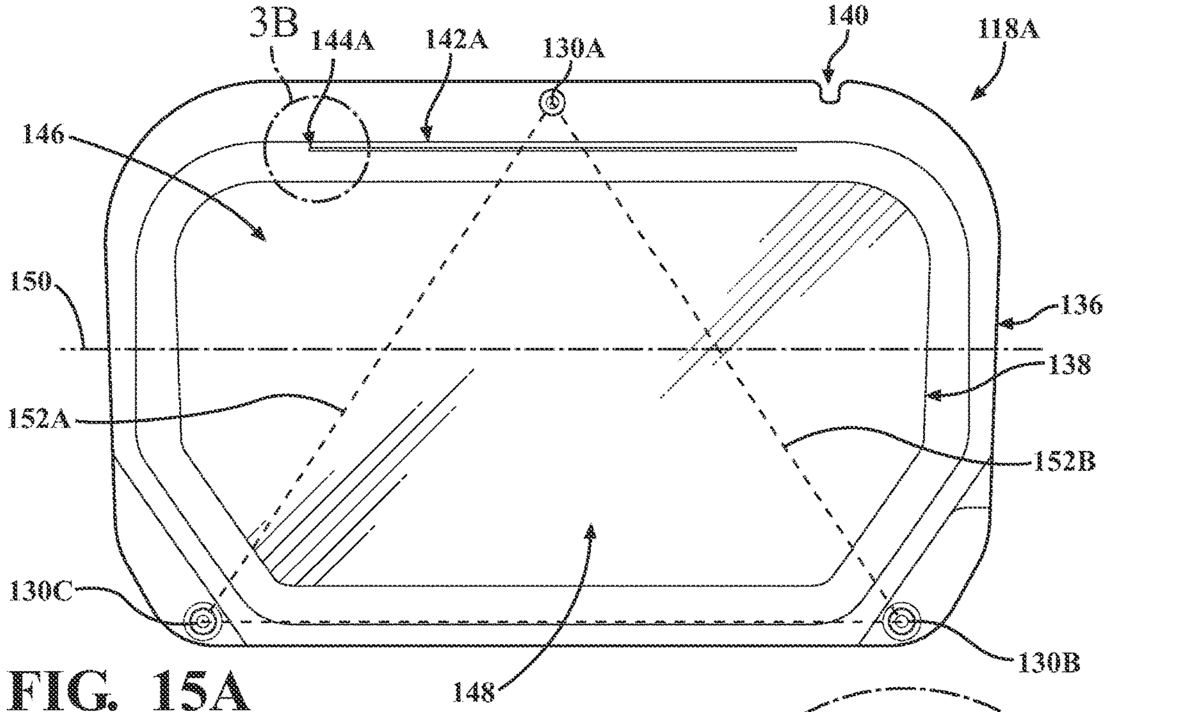
FIG. 15A is a front view of a first configuration of a transparent face shield of the surgical garment of FIG. 14, the face shield including a bounded cut.
Figure 15B:
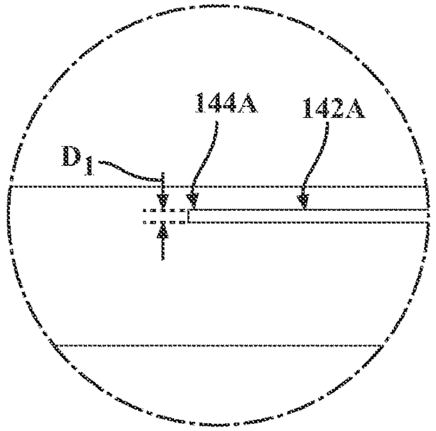
FIG. 15B is a zoomed view of a portion of the bounded cut of the face shield of FIG. 3A.
Figure 15C:
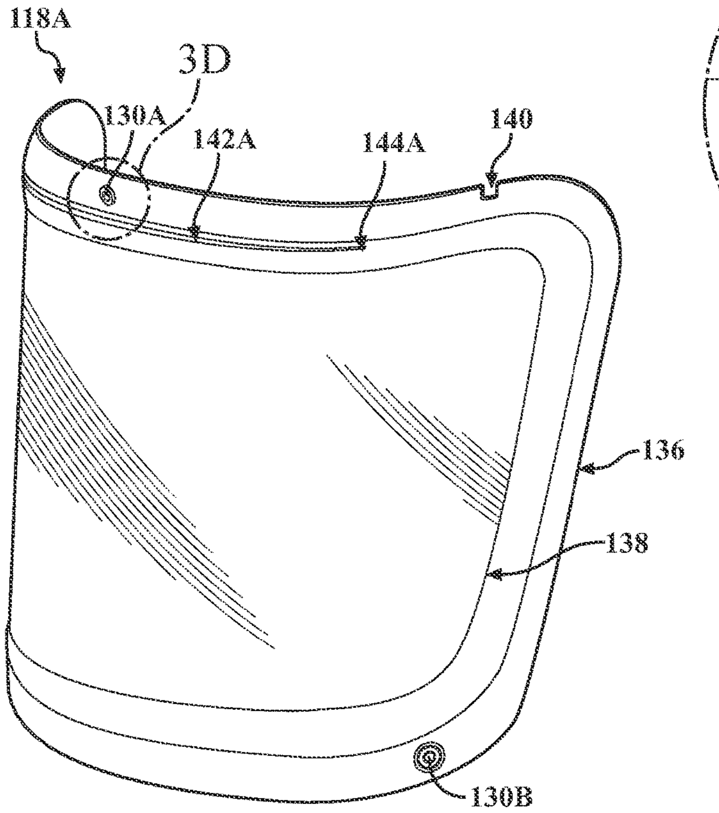
FIG. 15C is a perspective view of the transparent shield of FIG. 15A, the face shield arranged in a bent configuration as if attached to a surgical helmet as illustrated in FIG. 13.
Figure 15D:
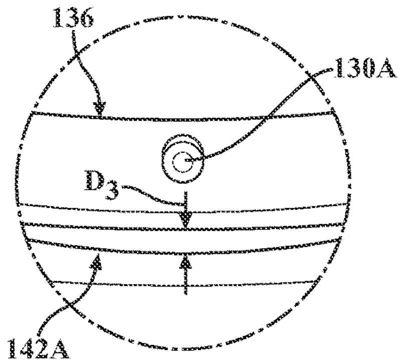
FIG. 15D is a zoomed view of a portion of the bounded cut of the face shield of FIG. 15C.

Referring to FIGS. 15A to 19D a first configuration of a bounded cut 142A in the face shield 118A. In this configuration of the bounded cut 142A, the bounded cut 142A has a generally consistent width D1 across the length of the bounded cut 142A between terminal ends 144A of the bounded cut 142A when the face shield 118A is oriented in a flat state or configuration, as illustrated in FIGS. 15A and 15B. Referring to FIG. 15B, the bounded cut 142A comprises a generally square and unform terminal ends 144A. As described above, the face shield 118A is flexed or bent state providing a face shield 118A with a curved profile when the face shield 118A is coupled to the surgical helmet 102. FIGS. 15C and 15D illustrate how the bounded cut 142A may be manipulated when the face shield 118A is flexed and/or coupled to the surgical helmet 102. As the face shield is manipulated from the flat state to the flexed state, the arrangement of the bonded cut 142A and the attachment elements 130 are likely to alter or deform the bonded cut 142A from its original shape. For example, as the face shield is manipulated to a be in the flexed state, this may cause the shape, width, and/or thickness of the bonded cut 142A to change. As illustrated in FIG. 15D, if can be seen that the bonded cut 142A has a width and/or thickness defined by a third dimension D3. The third dimension is greater than the first dimension D1 representing the width and/or thickness of the bonded cut 142A in the flat state. Referring to FIGS. 15B and 15D, it can be seen that as the face shield 118A is manipulated into the flexed state of FIG. 15C, the size and/or shape of the bounded cut 142A changes because of the bounded cut 142A being located between the upper attachment element 130A and the pair of lower attachment elements 130B, 130C of the face shield 118A as the face shield 118A goes from the flat state to the flexed state. This arrangement of bounded cut 142A being located between the upper attachment 130A allows the portion of the face shield 118A including the upper attachment element 130A to move more independently as it is less constrained by the shape of the face shield 118A and the arrangement of the attachment elements 130 because of the positioning and the shape of the bounded cut 142A. Such an arrangement of the arrangement of bounded cut 142A and the attachment elements 130 can mitigate the strain on face shield 118A proximate the upper attachment element when the face shield 118A is in the flexed state.

As illustrated in FIG. 15A, a first imaginary line 152A may extend between the upper attachment element 130A and a first lower attachment element 130C of the pair of lower attachment elements and a second imaginary line 152B may extend between the upper attachment element a second lower attachment element 130B of the pair of lower attachment elements 130B, 130C. At least one of the first imaginary line 152A and/or the second imaginary line 152B may intersect the bounded cut 142A when the face shield 118A is in a flat state of FIG. 15A. A third imaginary line 152C may extend between the pair of lower attachment elements 130B, 130C, such that the combination of the first, second, and third imaginary lines 152A, 152B, 152C intersect one another to define a triangle.

Figure 16A:
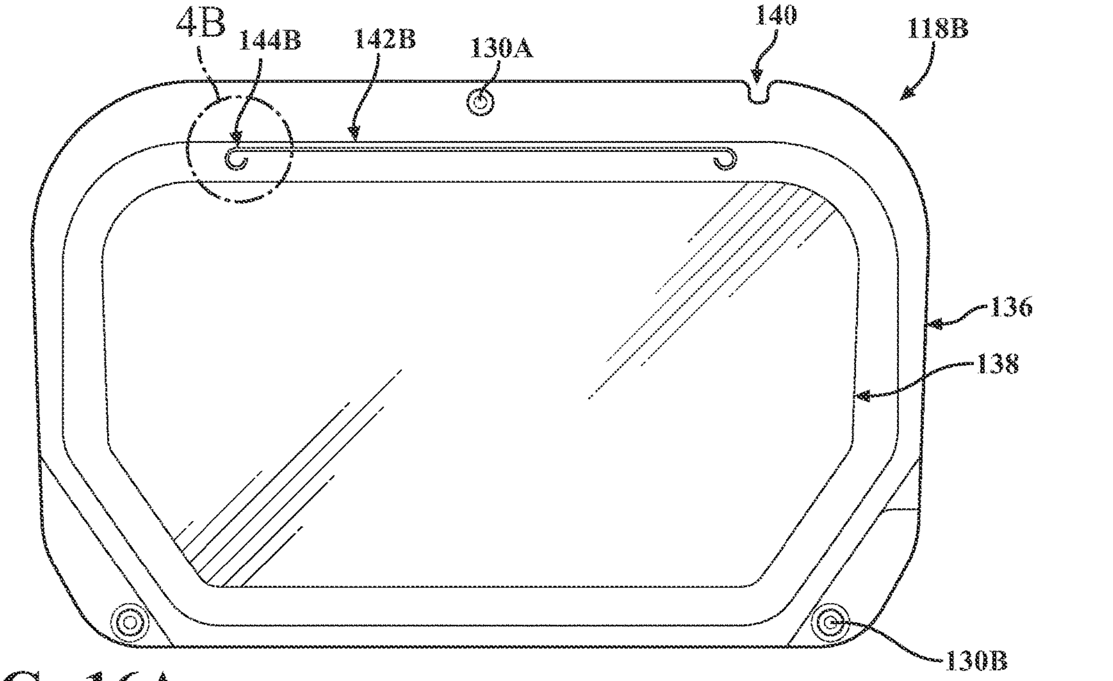
FIG. 16A is a front view of a second configuration of a transparent face shield of the surgical garment of FIG. 14, the face shield including a bounded cut.
Figure 16B:
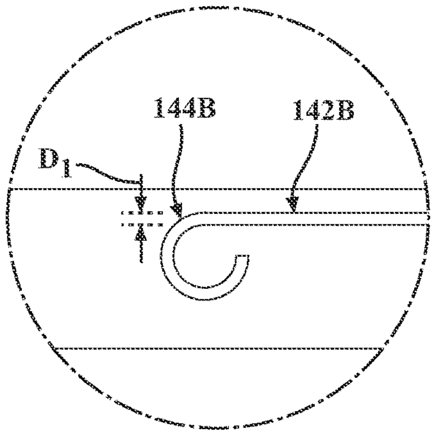
FIG. 16B is a zoomed view of a portion of the bounded cut of the face shield of FIG. 16A.
Figure 16C:
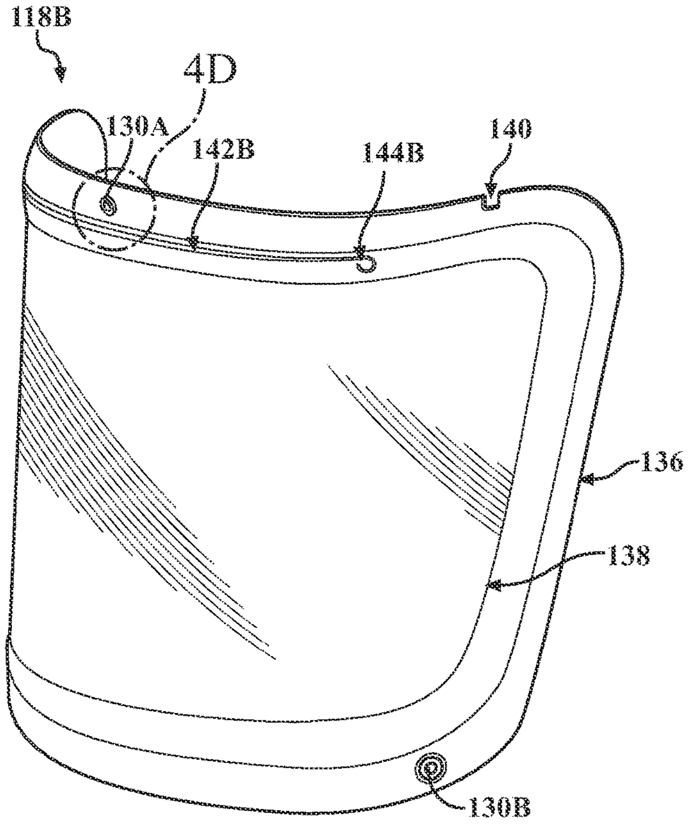
FIG. 16C is a perspective view of the transparent shield of FIG. 16A, the face shield arranged in a bent configuration as if attached to a surgical helmet as illustrated in FIG. 13.
Figure 16D:
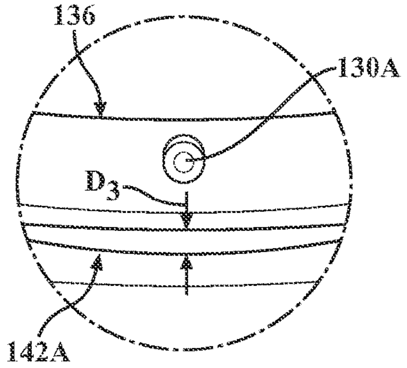
FIG. 16D is a zoomed view of a portion of the bounded cut of the face shield of FIG. 16C.
Figure 17A:
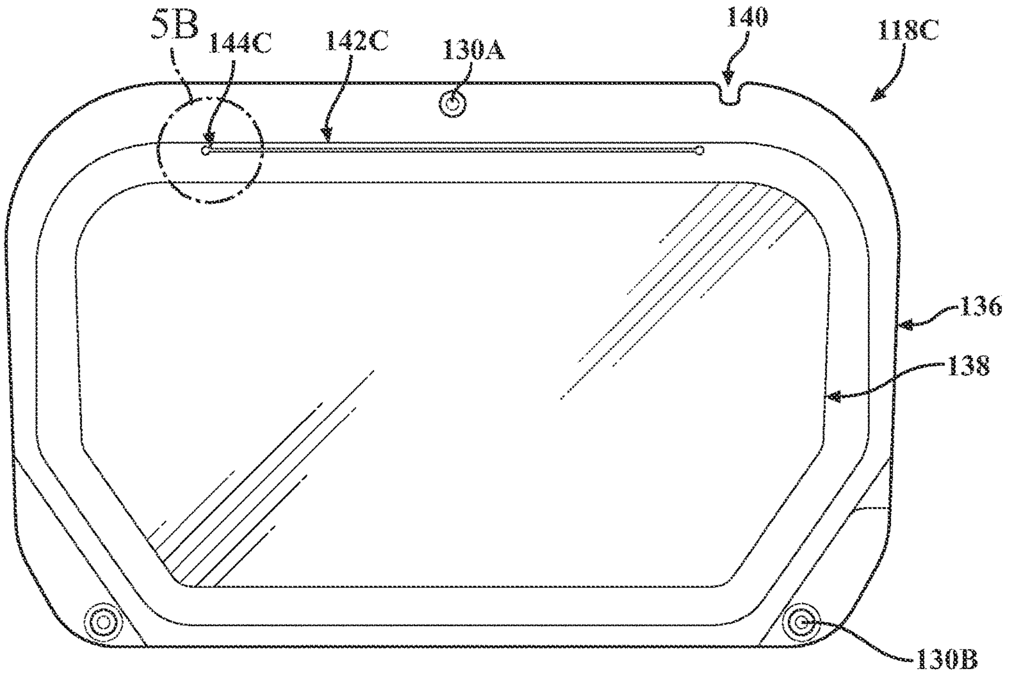
FIG. 17A is a front view of a third configuration of a transparent face shield of the surgical garment of FIG. 14, the face shield including a bounded cut.
Figure 17C:
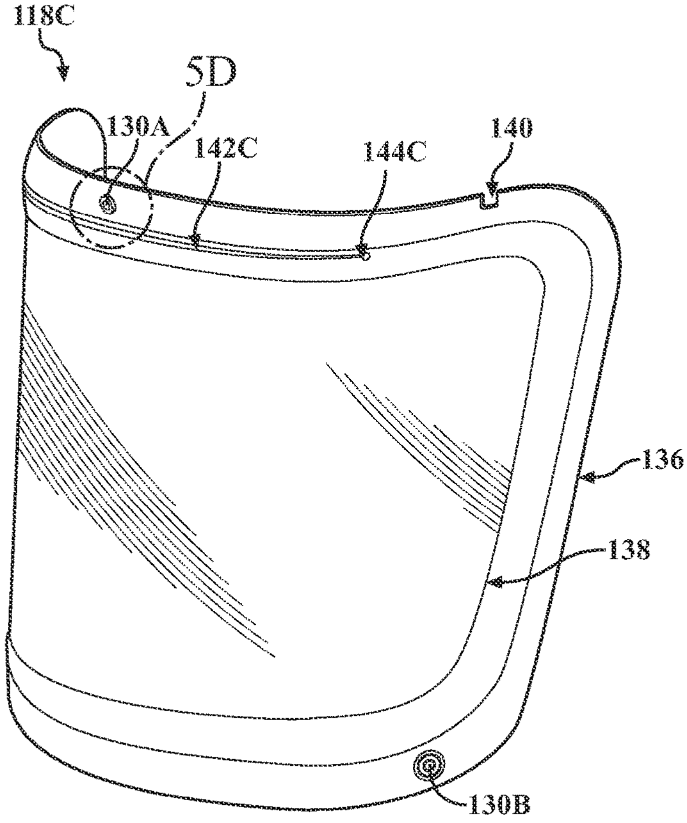
FIG. 17C is a perspective view of the transparent shield of FIG. 17A, the face shield arranged in a bent configuration as if attached to a surgical helmet as illustrated in FIG. 13.
Figure 17B:
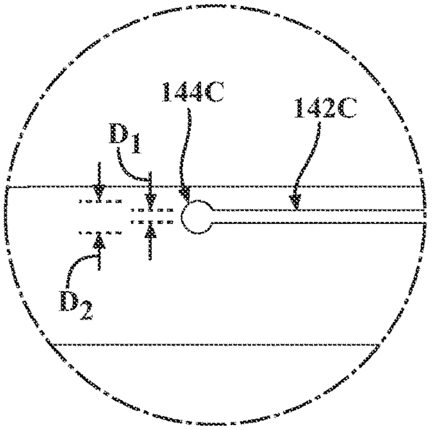
FIG. 17B is a zoomed view of a portion of the bounded cut of the face shield of FIG. 17A.
Figure 17D:
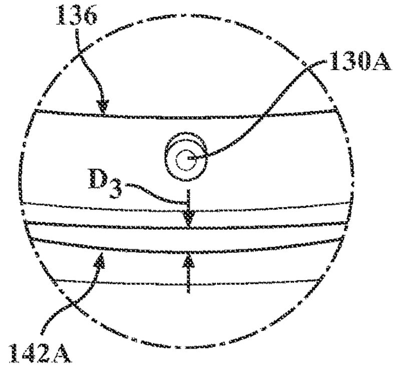
FIG. 17D is a zoomed view of a portion of the bounded cut of the face shield of FIG. 17C.
Figure 18A:
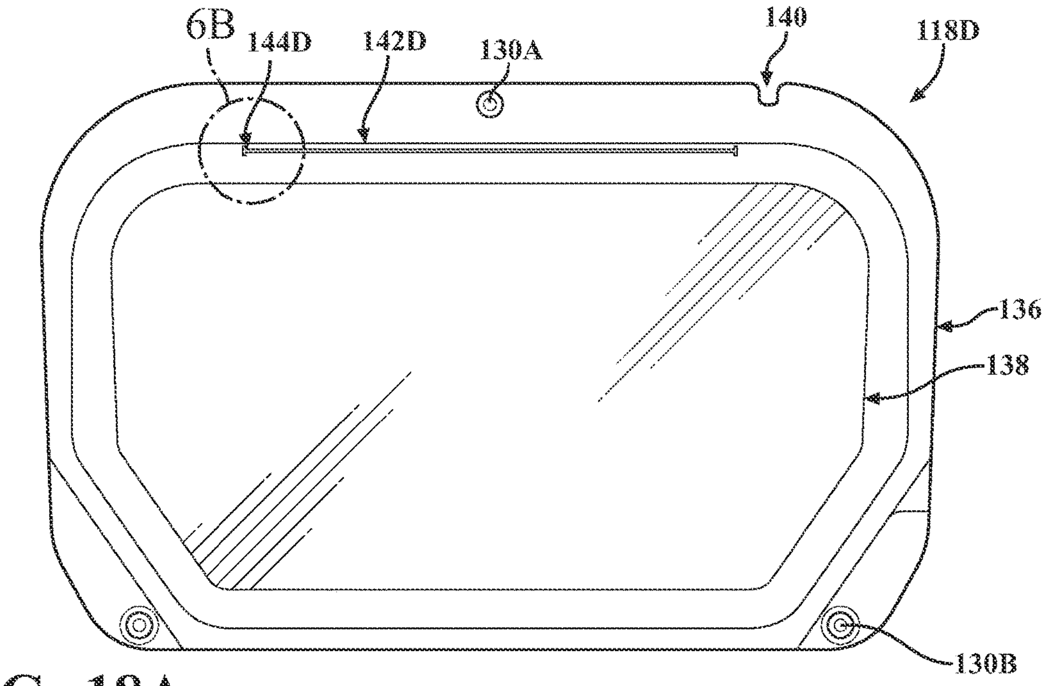
FIG. 18A is a front view of a fourth configuration of a transparent face shield of the surgical garment of FIG. 14, the face shield including a bounded cut.
Figure 18B:
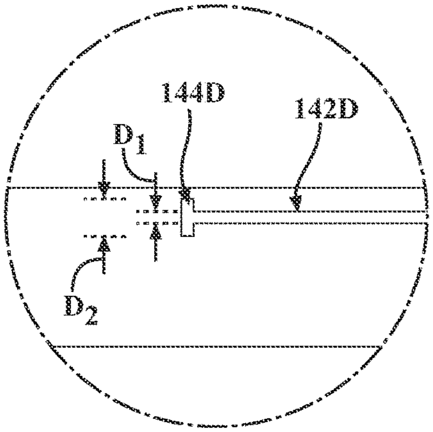
FIG. 18B is a zoomed view of a portion of the bounded cut of the face shield of FIG. 18A.
Figure 18C:
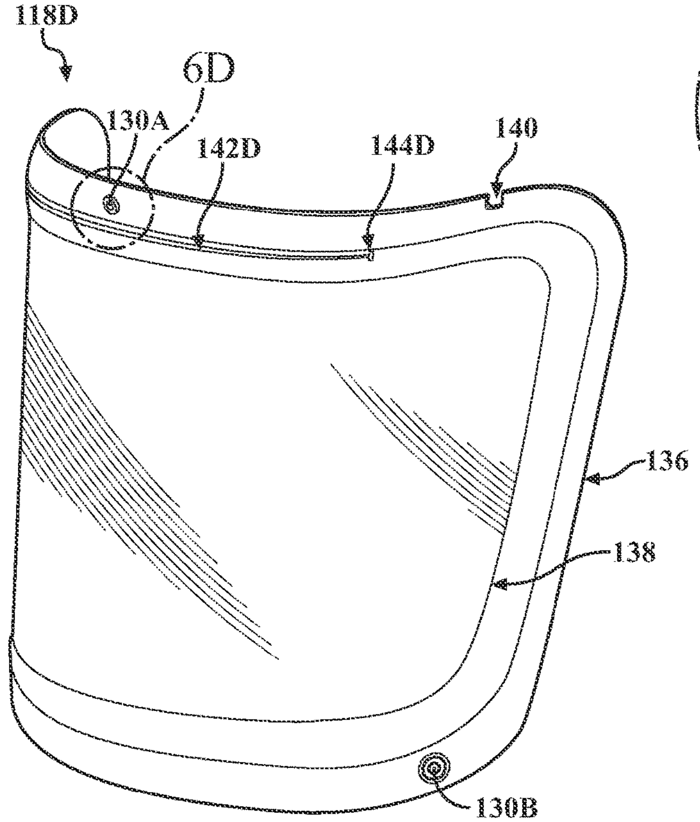
FIG. 18C is a perspective view of the transparent shield of FIG. 18A, the face shield arranged in a bent configuration as if attached to a surgical helmet as illustrated in FIG. 13.
Figure 18D:
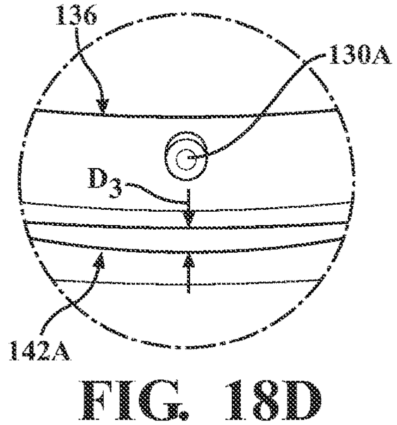
FIG. 18D is a zoomed view of a portion of the bounded cut of the face shield of FIG. 18C.
Figure 19A:
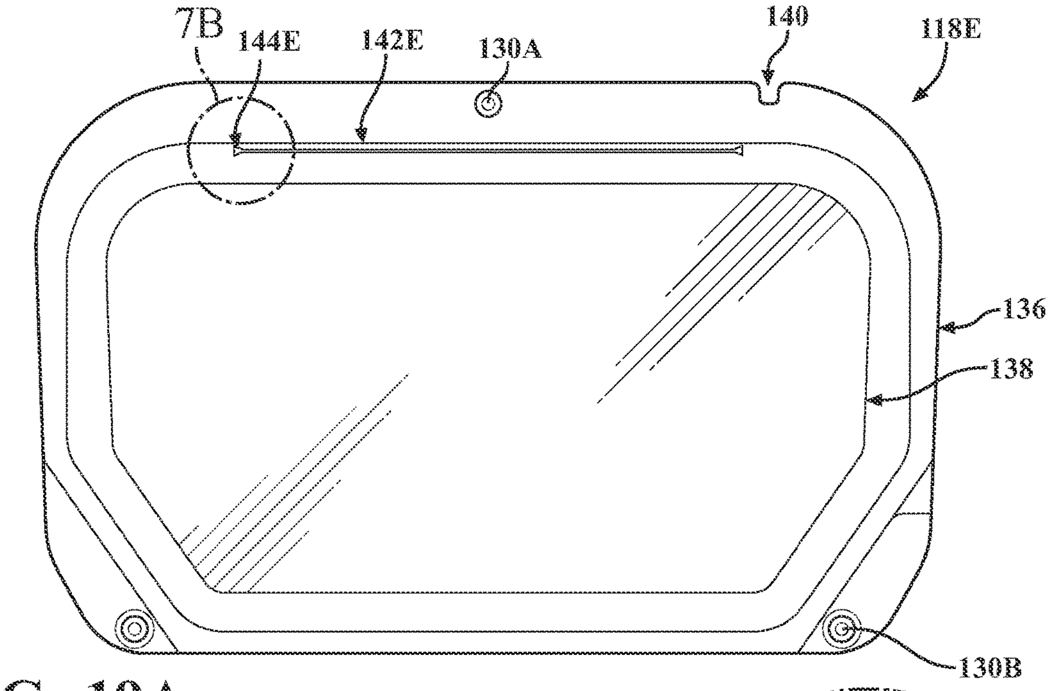
FIG. 19A is a front view of a fifth configuration of a transparent face shield of the surgical garment of FIG. 14, the face shield including a bounded cut.
Figure 19B:
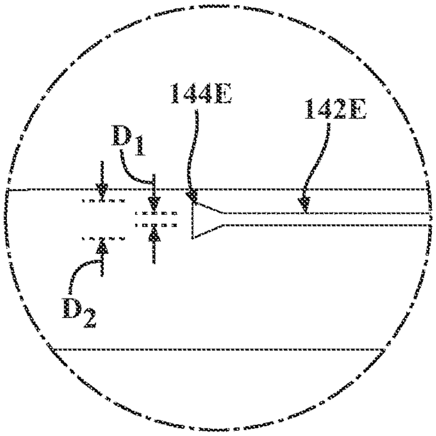
FIG. 19B is a zoomed view of a portion of the bounded cut of the face shield of FIG. 19A.
Figure 19C:
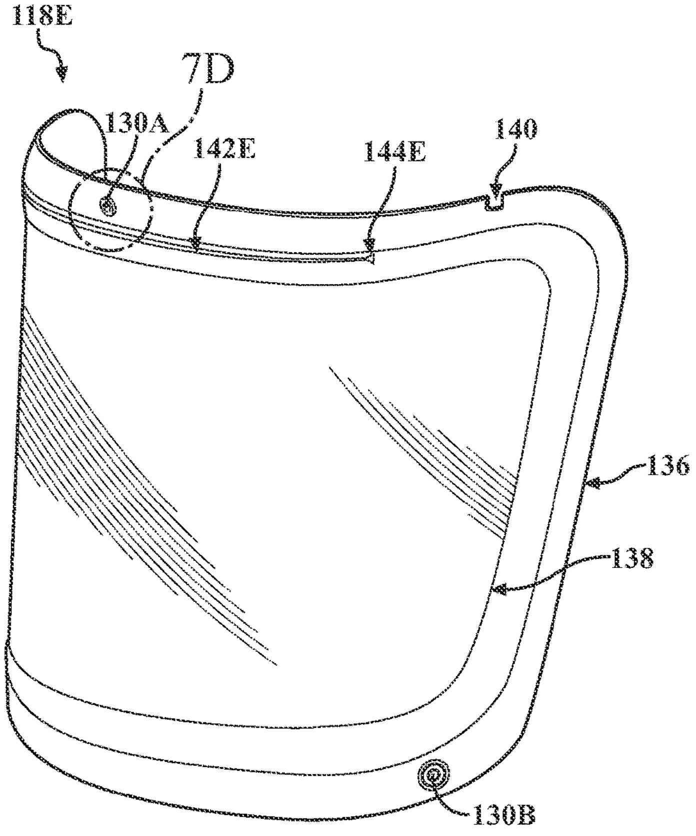
FIG. 19C is a perspective view of the transparent shield of FIG. 19A, the face shield arranged in a bent configuration as if attached to a surgical helmet as illustrated in FIG. 13.
Figure 19D:
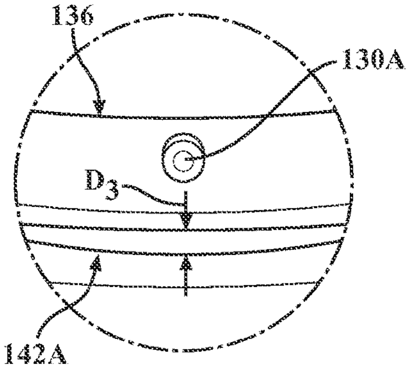
FIG. 19D is a zoomed view of a portion of the bounded cut of the face shield of FIG. 19C.

Referring to FIGS. 16A to 16D, an alternative configuration of a bounded cut 142B is illustrated. The bounded cut 142B illustrated in FIGS. 16A to 16D generally includes all the same features and/or characteristics of the bounded cut 142A described above. However, the bounded cut 142B of FIGS. 16A to 16D comprises an alternative configuration of the terminal ends 144B. As illustrated in FIGS. 16A to 16B, the bounded cut 142B generally consistent width D1 across the length of the bounded cut 142B between terminal ends 144B of the bounded cut 142B when the face shield 118B is oriented in a flat state. The terminal ends 144B of the bounded cut 142B may comprise a second bounded cut configured in a spiral or semi-circular shape. This configuration of the terminal end 144B of the bounded cut 142B may further mitigate the stress and/or strain on the face shield 118B proximate the terminal ends 144B. For example, the shape or configuration of the terminal end 144B may prevent cracking, fracturing, breaking, or similar damage to the face shield 118B at the terminal ends 144B as the face shield 118B is manipulated from the flat state to the flexed state and vice versa. The shape and/or configuration of the terminal ends 144B may allow for additional bending or flexing of the face shield to create different curvatures of the face shield 118B when attached to the surgical helmet 102 and in the flexed state. For example, the bonded cut 142B and/or the configuration of the terminal ends 144B may be utilized to create different curvature profiles of the face shield 118B when coupled to the surgical helmet 102, such as creating a uniform curvature profile of the shield across both the upper and lower portions 146, 148 of the face shield 118B. this can be true of each of the various configurations of the bounded cut 142A, 142B, 142C, 142D, 142E and/or terminal ends 144A, 144B, 144C, 144D, 144E of the face shield 118A, 118B, 118C, 118D, 118E illustrated in FIGS. 15A-19D.

Referring to FIGS. 17A to 17D, an alternative configuration of a bounded cut 142C is illustrated. The bounded cut 142C may comprise a terminal end 144C having a generally circular shaped profile. The terminal end 144C may define an opening having a second dimension D2, the second dimension D2 being greater than the first dimension D1 of the general width or thickness of the bounded cut 142C.

Referring to FIGS. 118A to 118D, an alternative configuration of a bounded cut 142D is illustrated. The bounded cut 142D may comprise a terminal end 144D having a generally rectangular shaped profile. The terminal end 144D may also be referred to as being T-shaped, based on the orientation of the rectangular shaped terminal end being arranged perpendicular to the longitudinal axis of the bounded cut 142D. The terminal end 144D may define an opening having a second dimension D2, the second dimension D2 being greater than the first dimension D1 of the general width or thickness of the bounded cut 142D.

Referring to FIGS. 19A to 19D, an alternative configuration of a bounded cut 142E is illustrated. The bounded cut 142E may comprise a terminal end 144E having a generally triangular shaped profile. Alternatively, the terminal end 144E may also be referred to as having a V-shaped profile. The terminal end 144E being oriented such that a point of the triangle or V is positioned at the end bounded cut 142E and one of the sides of the triangle is generally perpendicular to the longitudinal axis of the bounded cut 142E. The side of the triangle that is generally perpendicular to the longitudinal axis of the bounded cut 142E may comprise a length defined as a second dimension D2, the second dimension D2 being greater than the first dimension D1 of the general width or thickness of the bounded cut 142D.

Figure 20:
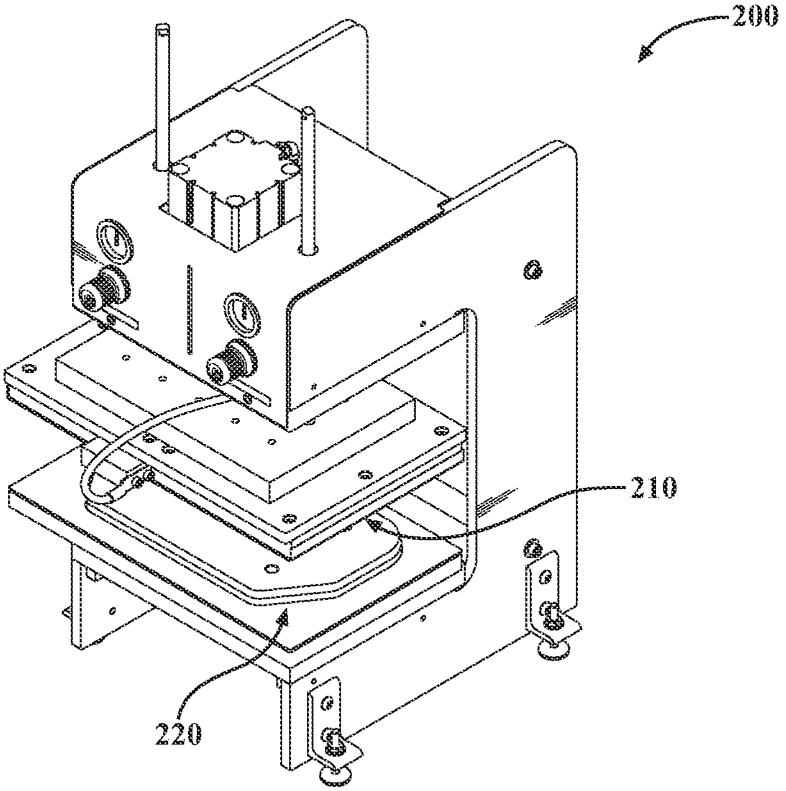
FIG. 20 is a perspective view of press for manufacturing a surgical garment, the press including a top plate and a bottom plate, at least one of which comprises a heated surface.
Figure 21:
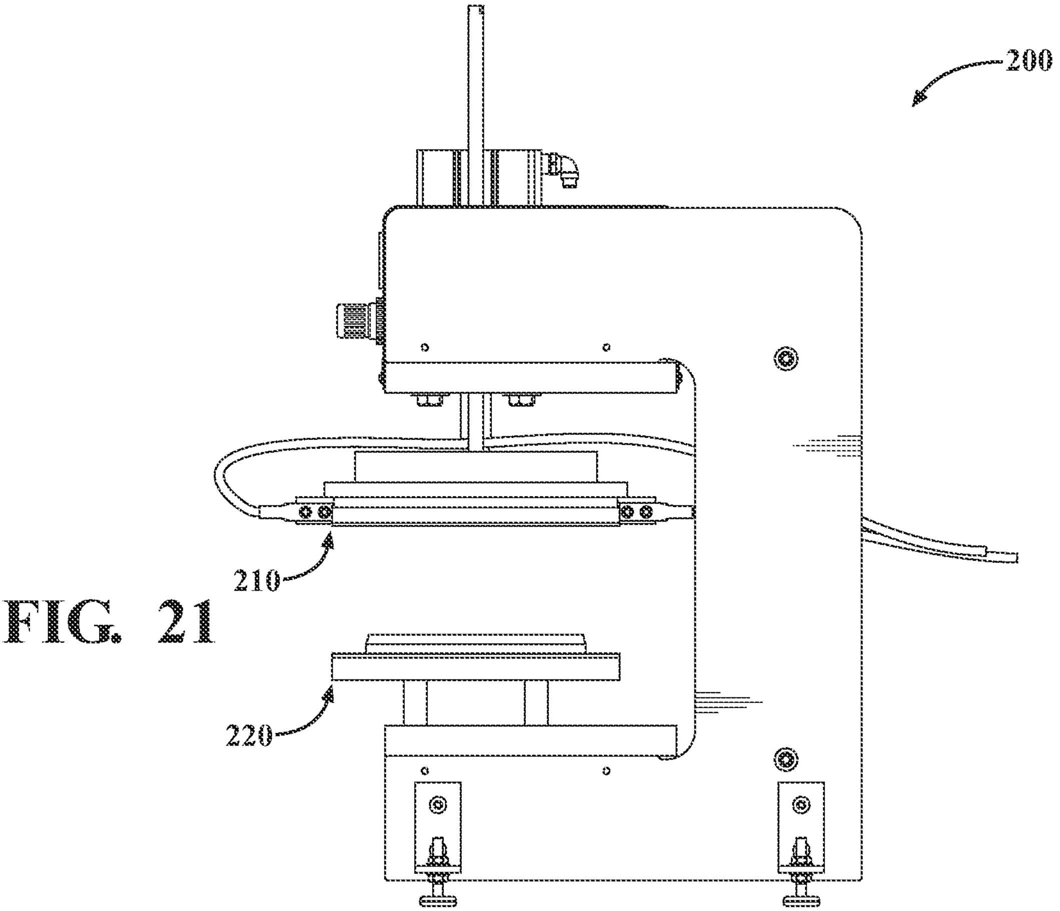
FIG. 21 is a side view of the press of FIG. 20 for manufacturing a surgical garment.
Figure 22:
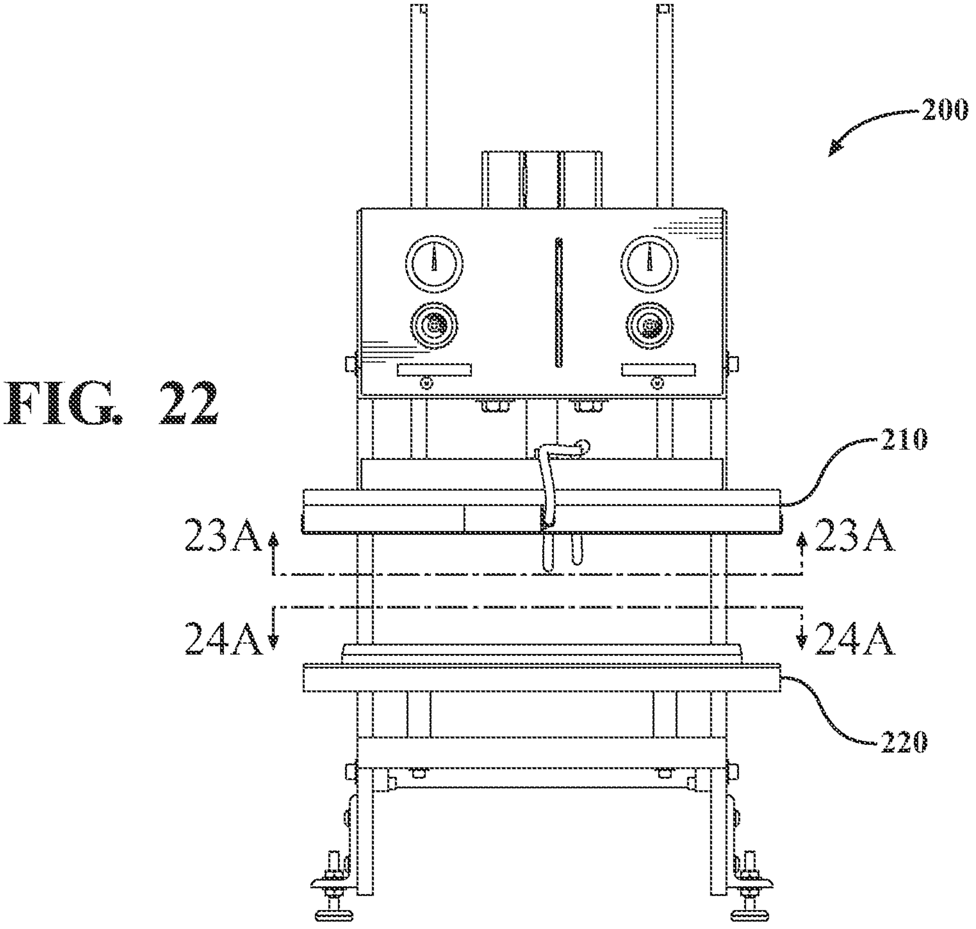
FIG. 22 is a front view of the press of FIG. 20 for manufacturing a surgical garment.

Referring to FIGS. 20 to 25D, an apparatus 200 for manufacturing a surgical garment 20, 120 is illustrated. Referring to FIGS. 20 to 22, a sample configured of a press 200 is illustrated. The press 200 may include an upper platen 210 and a lower platen 220 configured to be pressed together during the manufacturing of a surgical garment 20, 120 described above. During the manufacturing of the surgical garment, one or both of the upper platen 210 and/or the lower platen 220 may be heated to heat treat the surgical garment 20 when pressed between the upper platen 210 and the lower platen 220.

Figure 23A:
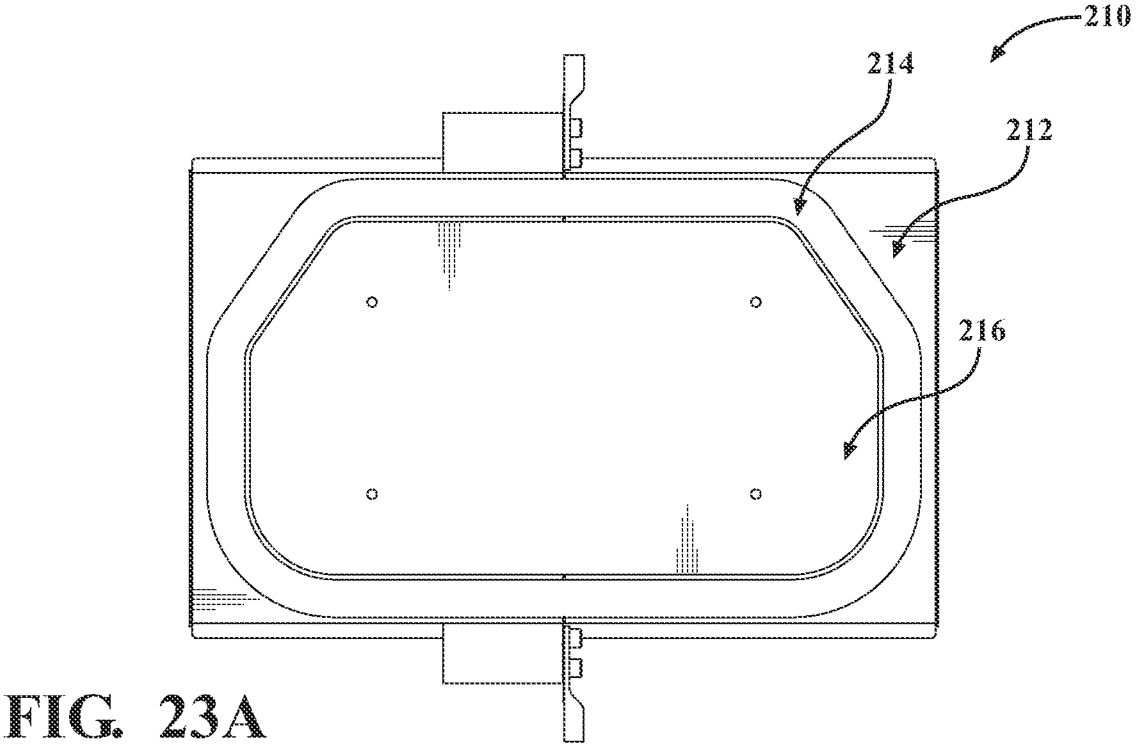
FIG. 23A is a top view of an example configuration of a top plate of the press of FIG. 20 for manufacturing a surgical garment.
Figure 23B:
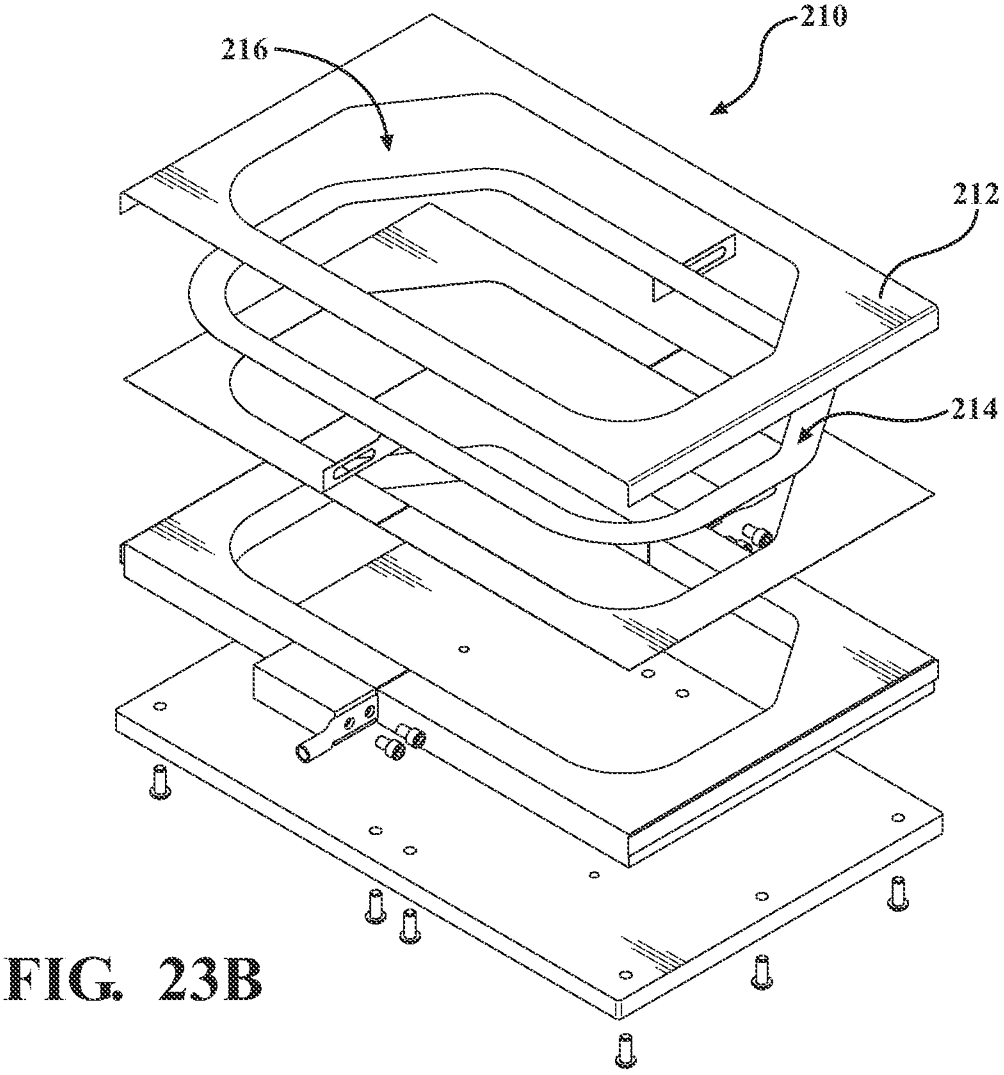
FIG. 23B is an exploded view of the top plate of FIG. 23A.
Figure 23C:
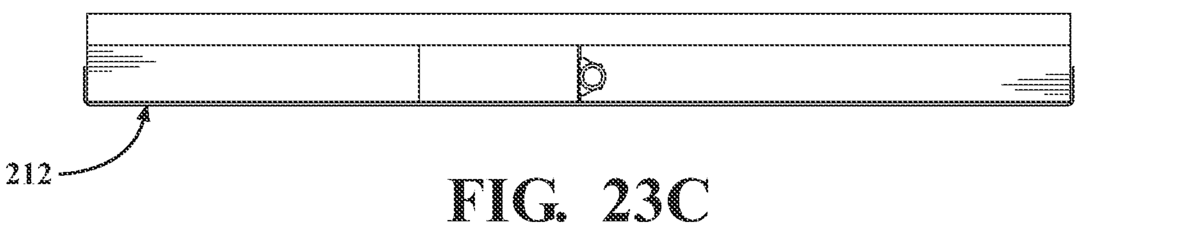
FIG. 23C is a side view of the top plate of FIG. 23A.
Figure 24A:
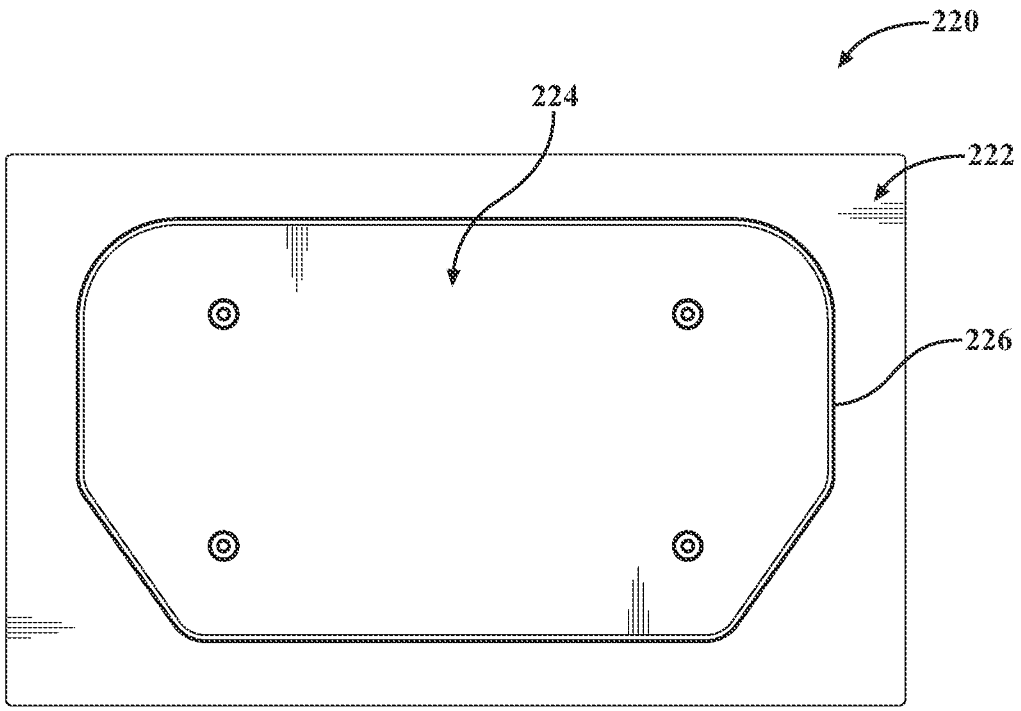
FIG. 24A is a top view of an example configuration of a bottom plate of the press of FIG. 20 for manufacturing a surgical garment.
Figure 24B:
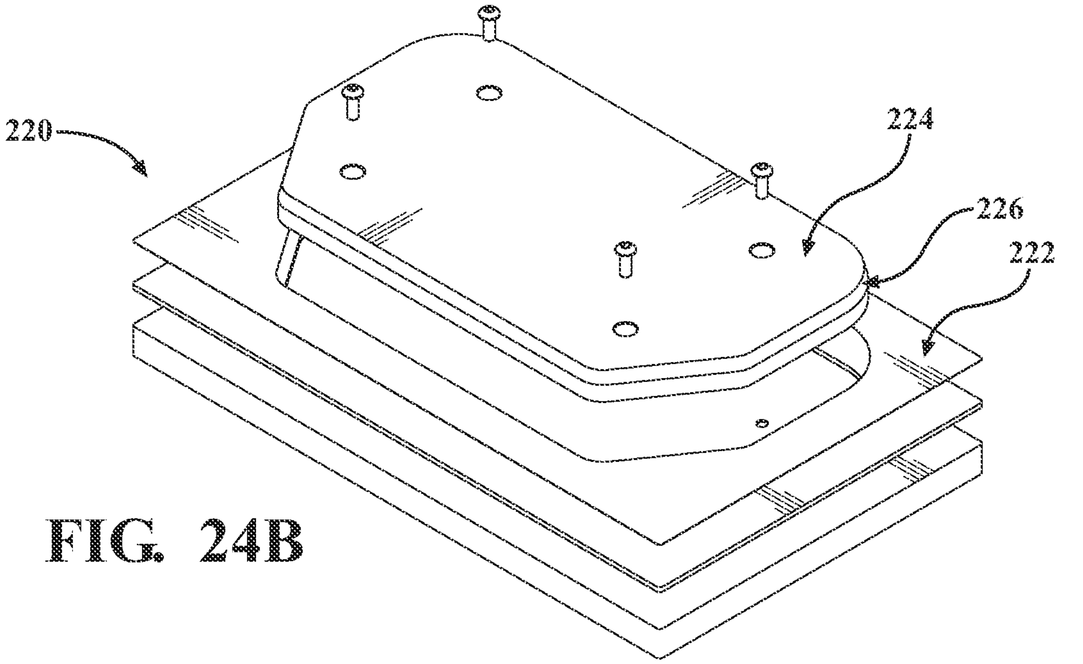
FIG. 24B is an exploded view of the bottom plate of FIG. 24A.
Figure 24C:
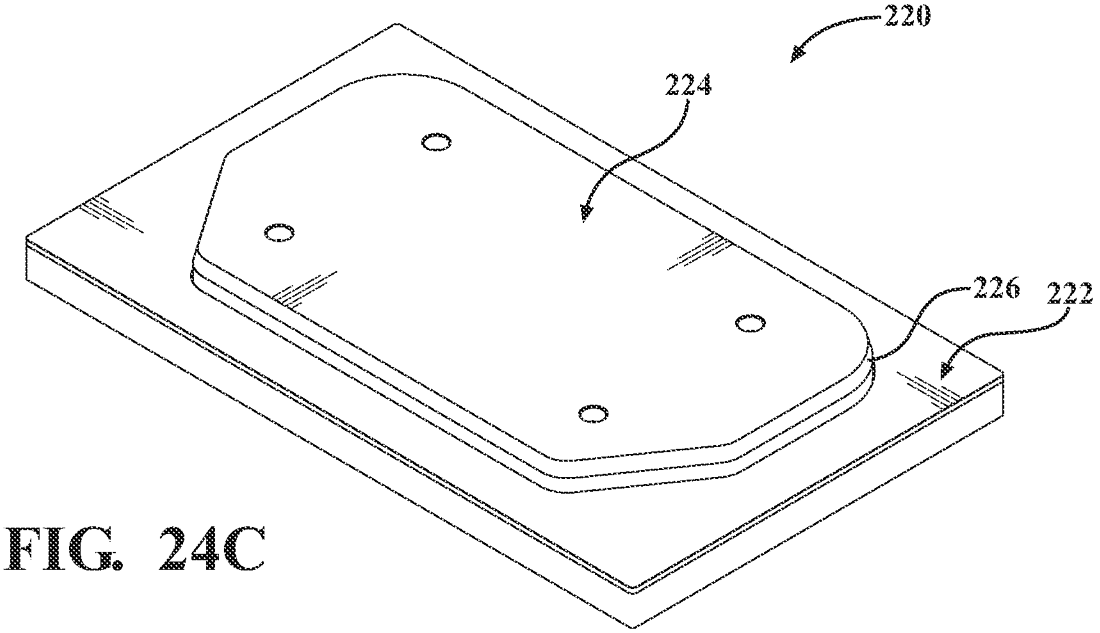
FIG. 24C is a perspective view of the bottom plate of FIG. 24A.
Figure 24D:
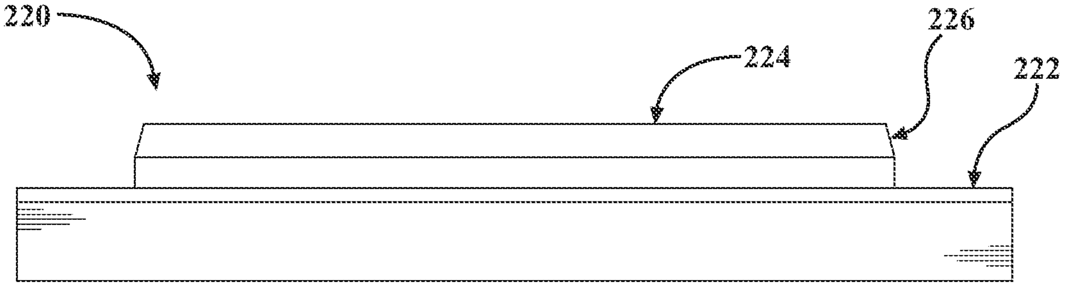
FIG. 24D is a side view of the bottom plate of FIG. 24A.

Referring to FIGS. 23A to 23C, an example configuration of the upper platen 210 for use in manufacturing of the surgical garment 20, 120 is illustrated. The upper platen 210 may comprise an upper contact surface 212. The upper contact surface 212 may comprise a generally flat profile and be configured to contact the surgical fabric 14, 114 of the surgical garment 20, 120. The upper platen 210 may further defined a recess 216 within the upper contact surface 212.

The upper platen 210 may also comprise a heating element 214. The heating element 214 may be position adjacent the contact surface and configured to heat the upper contact surface 212. The heating element 214 may be configured to heat the upper contact surface 212 to a temperature of at least 150 degrees Celsius and potentially as high as 250 degrees Celsius (i.e. approximately 300 and 482 degrees Fahrenheit).

Referring to FIGS. 24A to 24D, an example configuration of the lower platen 220 for use in manufacturing of the surgical garment 20, 120 is illustrated. The lower platen 220 may comprise a lower contact surface 222. The lower contact surface 222 may comprise a generally flat profile and be configured to contact the surgical fabric 14, 114 of the surgical garment 20, 120. While not illustrated, in the Figures, the lower contact surface 222 may also be heated via a heating element, similar to as is described with regard to the upper platen 210. It is contemplated that either one of or both of the upper platen 210 and/or the lower platen 220 may be heated.

The lower platen 220 may further comprise a protrusion 224 extending from the lower contact surface 222. The protrusion 224 may generally be shaped to fit within the recess 216 defined within upper contact surface 212. In operation, as the upper platen 210 and lower platen 220 are pressed together during the manufacturing process, the protrusion 224 is configured to fit within the recess 216. Furthermore, the protrusion 224 may be shaped to correspond to and/or fit within the opening 17, 117 defined with the surgical fabric 14, 114 of the surgical garment 20, 120, such that the opening 17, 117 defined in the surgical garment 20, 120 will allow the surgical garment to be placed over the protrusion 224 and have the surgical fabric 14, 114 of the surgical garment 20, 120 abutting the lower contact surface 222.

The protrusion 224 further comprise a chamfer 226 about the top edge of the protrusion. The chamfer 226 may be configured to align and/or guide the opening 17, 117 defined in the surgical fabric 14, 114 over the protrusion 224 and seat the surgical fabric 14, 114 against the lower contact surface 222.

Figure 25A:
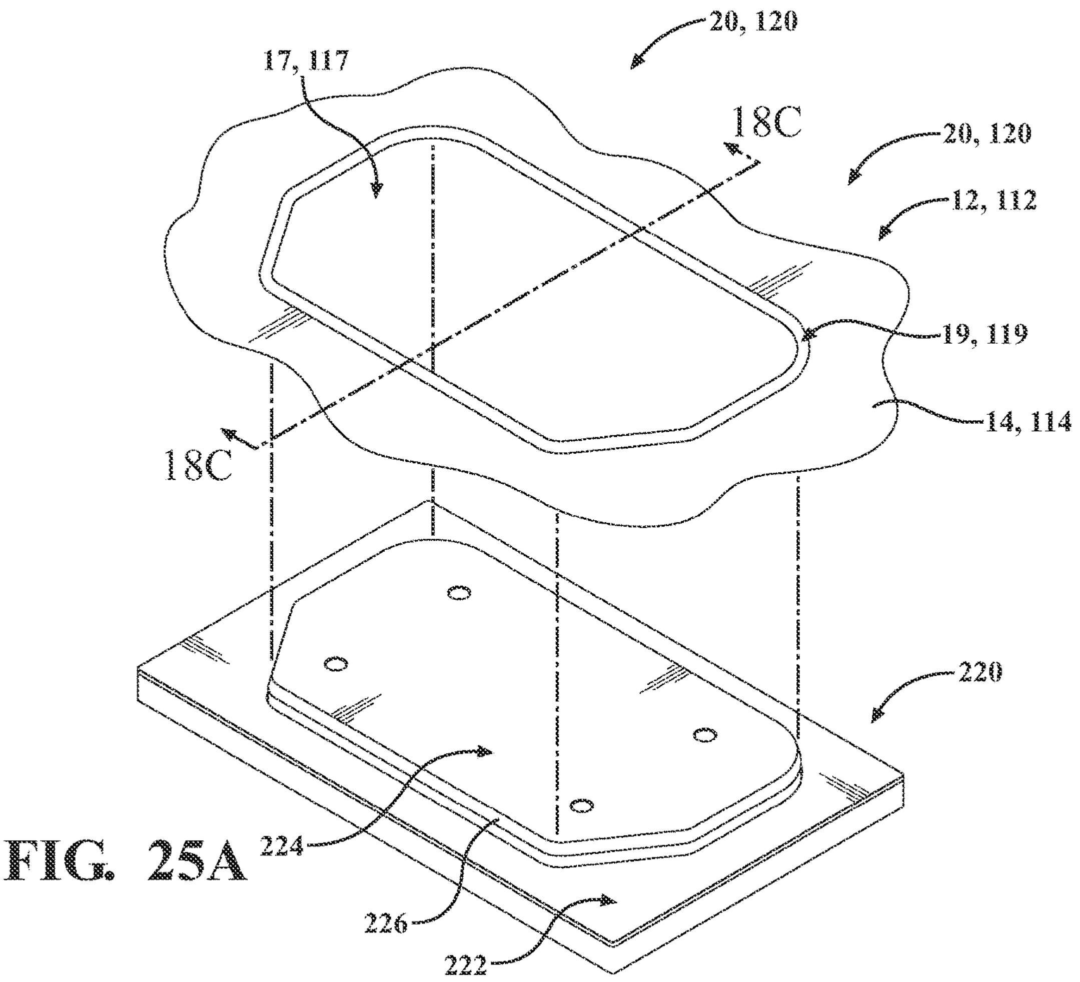
FIG. 25A is a perspective view of a surgical fabric of a surgical garment suspended over the bottom plate of the press of FIG. 20, the surgical garment to be placed over the bottom plate during manufacturing of the surgical garment using the press.

Referring to FIGS. 25A to 25D, various steps in the method of manufacturing a surgical garment 20, 120 are illustrated. FIG. 25A illustrates the step of placing the opening 17, 117 defined in the surgical garment 20, 120 over the protrusion 224 of the lower platen 220. In operation, the surgical garment 20, 120 may be suspended over the lower platen 220, and positioned so that the protrusion 224 of the lower platen 220 will fit within the opening 17, 117. The surgical garment 20, 120 may then be lowered onto the protrusion 224 such that the protrusion 224 is disposed within the opening 17, 117 and the surgical fabric 14, 114 abuts the lower contact surface 222 of the lower platen 220. As the surgical fabric 14, 114 is lowered onto the protrusion of the lower platen, the chamfered edge 226 of the protrusion 224 may assist in aligning and/or orienting the opening 17, 117 about the protrusion 224.

Figure 25B:
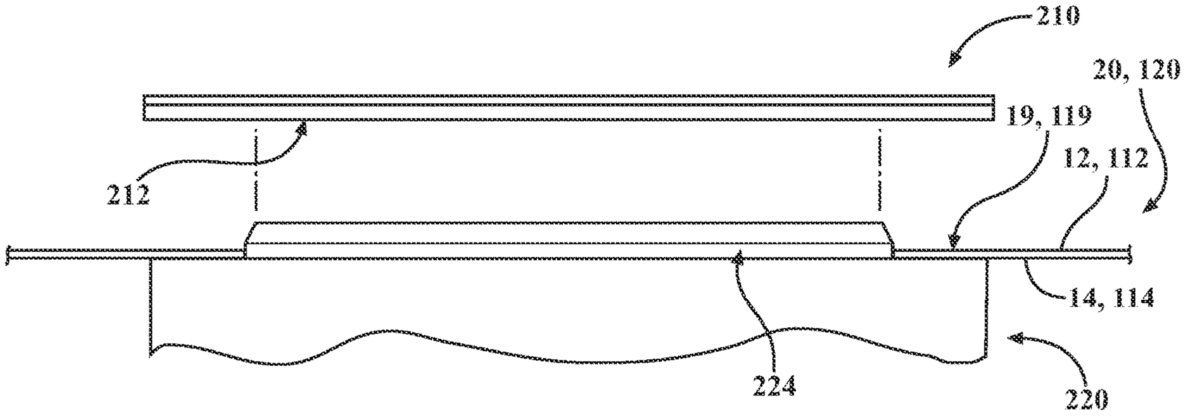
FIG. 25B is a side view of the top and bottom plates, including the surgical fabric of the surgical garment disposed over the bottom plate.

Referring to the FIG. 25B, once the surgical fabric 14, 114 of the surgical garment 20, 120 is seated against the lower contact surface 220, the upper contact surface 212 of the upper platen 210 may be heated via the heating element 214. The upper platen 210 may then be lowered via the press 200 such that the protrusion 224 of the lower platen 220 is seated within the recess 216 of the upper platen 210, and a portion of the surgical fabric 14, 114 is compressed between the upper contact surface 212 and the lower contact surface 222. A force of approximately XX pounds per square inch is applied to the surgical fabric 14, 114 but the upper contact surface 212 and the lower contact surface 222. The surgical fabric 14, 114 is also heated to a temperature of at least 150 degrees Celsius (i.e. approximately degrees Fahrenheit) by at least the upper contact surface 212.

Figure 25C:
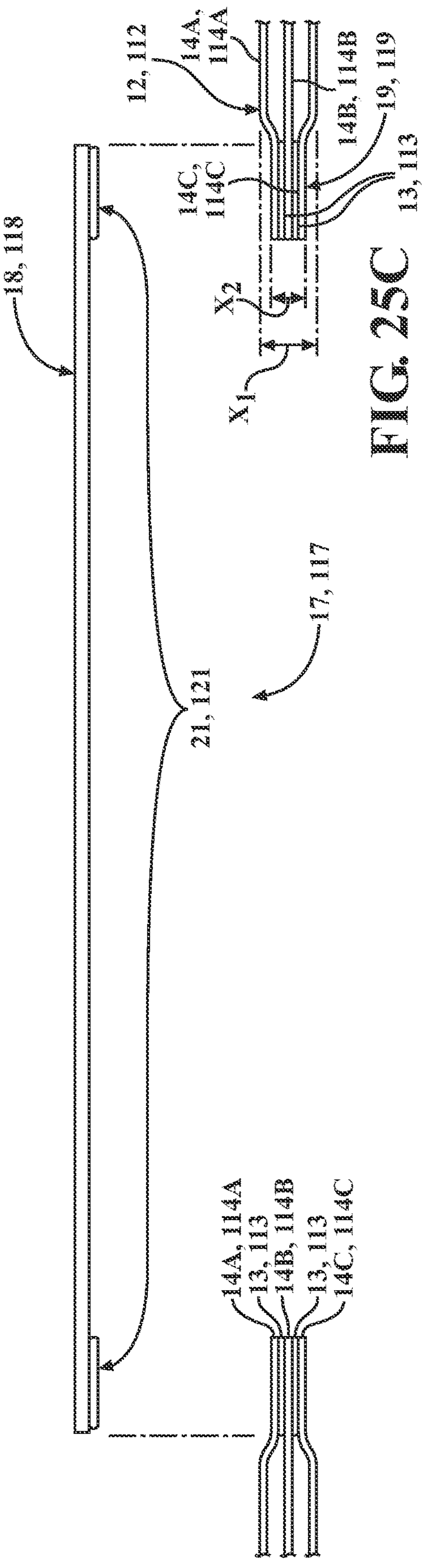
FIG. 25C is a sectional view of a transparent face shield being placed over an opening defined in the surgical fabric of a surgical garment, the surgical fabric previously subject to a heat treatment with the press of FIG. 20.
Figure 25D:
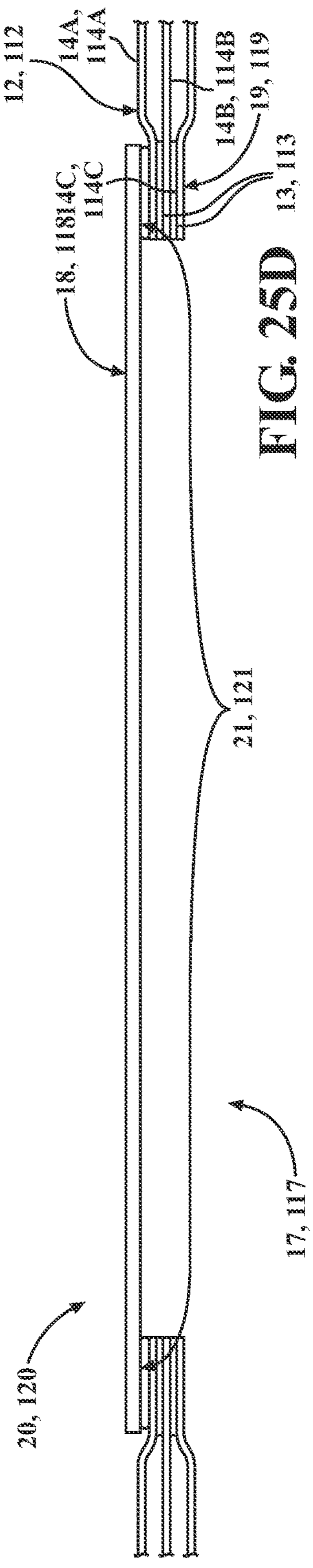
FIG. 25D is a sectional view of a transparent face shield coupled to the surgical fabric of a surgical garment, the surgical fabric previously subject to a heat treatment with the press of FIG. 20.

As described above, the surgical fabric 14, 114 may comprise one or more layers and be formed from woven material. The woven material may be a polyester, cotton, or a polyester-cotton blend. Additionally, it is contemplated that the material may be non-woven material such as fibers or filaments of paper, cotton, polyester, and the like. Referring to FIGS. 25C and 25D, the surgical fabric may be formed from a material including a plurality of layers 14A, 114A, 14B, 114B, 14C, 114C coupled together by an adhesive 13, 113. Compressing and heating the surgical fabric 14A, 114A, 14B, 114B, 14C, 114C results in the portion of the layers of the surgical fabric 14A, 114A, 14B, 114B, 14C, 114C that are compressed between the upper platen 210 and lower platen 220 defining a sealing perimeter 19, 119. The sealing perimeter 19, 119 including layers of the surgical fabric 14A, 114A, 14B, 114B, 14C, 114C that are more tightly bound and/or woven together. For example, the layers of the surgical fabric 14A, 114A, 14B, 114B, 14C, 114C defining the sealing perimeter 19, 119 may comprise a thickness of X2, with the layers of the surgical fabric 14A, 114A, 14B, 114B, 14C, 114C outside the sealing perimeter 19, 119 having a thickness of X1, such that the dimension of X1 is greater than the dimension of X2. Furthermore, the width of the surgical fabric 14A, 114A, 14B, 114B, 14C, 114C defining the sealing perimeter 19, 119 may be at least ten millimeters wide (10 mm). More specifically, the width of the sealing perimeter may be at least fifteen-millimeters wide (15 mm). Even more specifically, the width of the sealing perimeter may be at least twenty-millimeters wide (20 mm).

After the layers of the surgical fabric 14A, 114A, 14B, 114B, 14C, 114C have been compressed and heated between the upper platen 210 and lower platen 220 to define the sealing perimeter 19, 119 encircling the opening 17, 117, the transparent face shield 18, 118 may be disposed over the opening 17, 117 and coupled to the sealing perimeter 19, 119 of the surgical fabric 14A, 114A, 14B, 114B, 14C, 114C. In operation, an adhesive 21, 121 may be applied to one of the transparent face shield 18, 118 or the sealing perimeter 19, 119 of the surgical fabric 14A, 114A, 14B, 114B, 14C, 114C. The adhesive may comprise a pressure sensitive adhesive. Furthermore, the adhesive 13, 113 may be applied to cover at least a one-millimeter thick (1 mm) portion of a surface of one of the transparent face shield 18, 118 or the sealing perimeter 19, 119 of the surgical fabric 14A, 114A, 14B, 114B, 14C, 114C. More specifically, the adhesive 13, 113 may be applied to cover at least a one-millimeter thick (1 mm) portion of a surface of one of the transparent face shield 18, 118 or the sealing perimeter 19, 119 of the surgical fabric 14A, 114A, 14B, 114B, 14C, 114C. The adhesive 13, 113 being applied with a thickness of at least a one-millimeters in combination with the sealing perimeter 19, 119 having at least a five-millimeter width being pressed together can provide the advantage of creating a sufficient seal between the transparent face shield 18, 118 and the surgical fabric 14A, 114A, 14B, 114B, 14C, 114C to pass current sterility standards.

The transparent face shield 18, 118 and the sealing perimeter 19, 119 of the surgical fabric 14A, 114A, 14B, 114B, 14C, 114C may be compressed together to activate the pressure sensitive adhesive and coupling the transparent face shield 18, 118 to the surgical fabric 14A, 114A, 14B, 114B, 14C, 114C. The transparent face shield 18, 118 and the surgical fabric 14A, 114A, 14B, 114B, 14C, 114C may compressed using two flat plates on opposed sized of the transparent face shield 18, 118 to the surgical fabric 14A, 114A, 14B, 114B, 14C, 114C. Alternatively, the transparent face shield 18, 118 to the surgical fabric 14A, 114A, 14B, 114B, 14C, 114C may compressed by a roller on opposed sides of the transparent face shield 18, 118 to the surgical fabric 14A, 114A, 14B, 114B, 14C, 114C tracing the sealing perimeter and compressing the transparent face shield 18, 118 to the surgical fabric 14A, 114A, 14B, 114B, 14C, 114C. The transparent face shield 18, 118 and the surgical fabric 14A, 114A, 14B, 114B, 14C, 114C may compressed by a force ranging from approximately five pounds per square inch (5 psi) to approximately one-hundred pounds per square inch (100 psi). More specifically, the transparent face shield 18, 118 and the surgical fabric 14A, 114A, 14B, 114B, 14C, 114C may compressed by a force of at least thirty pounds per square inch seventy (30 psi). Even more specifically, the transparent face shield 18, 118 and the surgical fabric 14A, 114A, 14B, 114B, 14C, 114C may compressed by a force of at least fifty pounds per square inch seventy (50 psi). Even more specifically, the transparent face shield 18, 118 and the surgical fabric 14A, 114A, 14B, 114B, 14C, 114C may compressed by a force of at least seventy pounds per square inch seventy (70 psi).

Also, while the surgical garment 20 is generally intended to provide a barrier between a medical practitioner and a patient during a medical or surgical procedure, its use is not so limited. It is within the scope of this disclosure that the garment may be used in other endeavors in which it is desirable to provide a barrier between an individual and the surrounding environment. One alternative endeavor in which it may be so desirable to use the garment is one in which it is desirable to provide a barrier between the individual and hazardous material in the environment in which the individual is working.

Clauses Directed to Additional Configurations

I. A surgical garment worn by an individual, the surgical garment comprising:
a sleeve having a distal end defining a lumen for receiving an arm of the individual;
a cuff portion disposed at the distal end of the sleeve, the cuff portion extending the lumen defined by the sleeve and further defining an opening; and
a barrier member disposed within the lumen proximal to the opening and configured to selectively prevent a hand of the individual's arm from extending through the opening defined by the cuff portion.

I-a. The surgical garment of claim I, wherein the barrier member is positioned within the lumen at an intersection of the distal end of the sleeve and a proximal end of the cuff portion.

I-b. The surgical garment of claim I, wherein the barrier member is positioned within the opening defined by the cuff portion to at least partially enclose the lumen defined by the cuff portion and the sleeve from the external environment.

I-c. The surgical garment of any one of claims I to I-b, wherein the barrier member is configured to transition from a closed configuration to an open configuration.

I-d. The surgical garment of claim I-c, wherein when the barrier member is in the closed configuration, the barrier member defines a barrier between the lumen defined by the sleeve and the external environment through the opening defined by the cuff portion.

I-e. The surgical garment of claim I-c, wherein the barrier member comprises a sealing member configured to transition the barrier member from the closed configuration to the open configuration.

I-f. The surgical garment of claim I-e, wherein the sealing member includes at least one of adhesives or stitching.

I-g. The surgical garment of claim I-e, wherein the barrier member transitions from the closed configuration to the open configuration as the sealing member is manipulated by the individual to allow a portion of the arm of the individual to extend past the barrier member and out of the opening defined by the cuff portion.

I-h. The surgical garment of claim I-c, wherein the barrier member comprises a first portion and a second portion joined by a fastener configured to transition the barrier member from the closed configuration to the open configuration.

I-i. The surgical garment of claim I-h, wherein the fastener includes at least one of a zipper, snaps, hook and loop, stitching, and adhesive configured to selectively join the first and second portions of the barrier member.

I-j. The surgical garment of claim I, wherein the barrier member is a film spanning the opening defined by the cuff portion to seal the lumen defined by the sleeve from the external environment, the film is configured to be breachable by the hand of the individual.

I-k. The surgical garment of any of the preceding claims, further comprising a glove including a glove opening configured to overlap a portion of the cuff portion to provide a continuous sterile barrier between the glove and sleeve.

I-l. The surgical garment of any of the preceding claims, wherein the barrier member comprises at least a first portion and a second portion defined by one or more perforations in the barrier member, the perforations creating a frangible connection between the portions of the barrier member that is breakable by the hand of the individual to transition the barrier member from a closed configuration to an open configuration.

I-m. The surgical garment of any of the preceding claims, wherein the barrier member is coupled to the sleeve and the barrier member at least partially covers an opening defined at the distal end of the sleeve.

I-n. The surgical garment of claim I-m, wherein the barrier member is coupled to the sleeve via stitching.

I-o. The surgical garment of claim I-m or I-n, wherein the cuff is partially disposed over the barrier member and is coupled to the distal end of the sleeve via stitching.

I-p. The surgical garment of any of the preceding claims, further comprising:

a body portion, the sleeve extending from the body portion;

a hood coupled to the body portion, the hood defining an opening configured to be in front of the individual's face when disposed over individual and/or a surgical helmet;

a transparent face shield disposed over the opening defined in the hood; and at least one attachment element disposed on the transparent face shield, the attachment element for removably coupling the surgical garment to the surgical helmet.

I-q. The surgical garment of claim I-p, wherein the transparent face shield is formed of a flexible and transparent material and including a top portion, a bottom portion, and a sealing perimeter, the transparent face shield further comprising:

a pair of lower attachment elements disposed on the bottom portion of the face shield; and an upper attachment element disposed on the top portion of the face shield, the upper and lower attachment elements defining three mounting locations at which the face shield is removably mounted to the surgical helmet;

wherein the face shield defines a bounded cut, the bounded cut being disposed between the sealing perimeter and an outer edge of the face shield; and wherein the bounded cut being at least partially disposed between the upper attachment element and at least one of the pair of lower attachment elements II. A personal protection system to be worn by an individual, the personal protection system comprising:

a surgical garment comprising:

a garment body including a material configured to provide a sterile barrier between the individual and an external environment;

a sleeve extending from the garment body and defining a lumen for receiving an arm of the individual, the sleeve defining an opening at a distal end of the sleeve; and the sleeve is transitionable between a closed configuration and an open configuration, when in the closed configuration, the sleeve includes a barrier member to define a barrier for selectively limiting the hand of the individual from extending through the opening.

II-a. The personal protection system of claim II, wherein the barrier member is configured to couple a first portion of the sleeve to a second portion of the sleeve to define the barrier preventing the hand of the individual from extending through the opening.

II-b. The personal protection system of claim II, wherein at least a portion of the barrier member is configured to be manipulated when the barrier member transitions from the closed configuration to the open configuration.

II-c. The personal protection system of claim II-b, wherein the barrier member includes a fastener configured to transition the barrier member from the closed configuration to the open configuration, the fastener including at least one of a zipper, snap, hook and loop, stitching, and adhesive configured to selectively join a first portion and a second portion of the barrier member.

II-d. The personal protection system of claim II, wherein the barrier member is coupled to either an interior surface or an exterior surface of the sleeve.

II-e. The personal protection system of claim II, wherein the surgical garment further includes a cuff portion disposed at the distal end of the sleeve, the cuff portion extending the lumen defined by the sleeve and further defining a cuff opening.

II-f. The personal protection system of claim II-e, wherein when the barrier member is in the closed configuration, the barrier member encloses the lumen defined by the sleeve from the external environment.

II-g. The personal protection system of claim II-e, wherein barrier member is a film spanning the cuff opening defined by the cuff portion, the film configured to be breachable by the individual's hand.

II-h. The personal protection system of claim II, wherein the barrier member comprises a first portion and a second portion joined by a fastener configured to transition the barrier member from the closed configuration to the open configuration.

II-i. The personal protection system of claim II-h, wherein the fastener includes at least one of a zipper, snaps, hook and loop, stitching, and adhesive configured to selectively join the first and second portions of the barrier member.

II-j. The personal protection system of claim II, wherein a proximal end of the sleeve is coupled to the garment body.

II-k. The personal protection system of claim II, wherein the sleeve comprises the same material as the material of the garment body.

II-l. The personal protection system of any of claims II to II-h, further comprising a glove including a glove opening configured to overlap a portion of the sleeve to provide a continuous sterile barrier between the glove and sleeve.

II-m. The personal protection system of claim II-l, wherein the barrier member is configured to transition from the closed configuration to the open configuration after the glove has been positioned to overlap a portion of the sleeve, maintaining the sterile barrier between the individual and the external environment.

II-n. The surgical garment of claim I, wherein the barrier member comprises at least a first portion and a second portion defined by one or more perforations in the barrier member, the perforations creating a frangible connection between the portions of the barrier member that is breakable by the hand of the individual to transition the sleeve from the closed configuration to the open configuration.

II-o. The surgical garment of claim II-n, wherein the barrier member is coupled to the sleeve and the barrier member selectively covers the opening defined by the sleeve.

II-p. The surgical garment of claim II-o, wherein the barrier member is coupled to the sleeve via stitching.

II-q. The surgical garment of claim II-o or II-p, wherein the surgical garment further comprises a cuff portion disposed at the distal end of the sleeve, the cuff portion at least partially disposed over the barrier member and is coupled to the distal end of the sleeve via stitching.

III. A protective garment worn by an individual, the protective garment comprising:

a garment body including a material configured to provide a sterile barrier between the individual and an external environment;

a sleeve extending from the garment body, the sleeve having a distal end and a proximal end and defining a lumen for receiving an arm of the individual;

a cuff portion disposed at the distal end of the sleeve, the cuff portion extending the lumen defined by the sleeve and further defining an opening; and a barrier member disposed within the lumen defined by the sleeve and configured to selectively prevent the hand of the individual from extending through the opening defined by the cuff portion.

III-a. The surgical garment of claim III, wherein the barrier member comprises at least a first portion and a second portion defined by one or more perforations in the barrier member, the perforations creating a frangible connection between the portions of the barrier member that is breakable by the hand of the individual to transition from the closed configuration to the open configuration.

III-b. The surgical garment of III or III-a, wherein the barrier member is coupled to the sleeve and the barrier member selectively encloses the lumen defined by the sleeve.

III-c. The surgical garment of claim III-b, wherein the barrier member is coupled to the sleeve via stitching.

III-d. The surgical garment of claim III-b or III-c, wherein the cuff is partially disposed over the barrier member and is coupled to the distal end of the sleeve via stitching.

IV. A method of donning a personal protection system, the method comprising:

providing a protective garment including a sleeve defining a lumen and an opening at a distal end of the sleeve, the lumen configured to receive an arm of an individual wearing the protective garment, and a barrier member disposed within the lumen and configured to define a barrier for selectively limiting access to the lumen from an external environment via the opening;

inserting the arm of the individual into the lumen through a proximal opening of the sleeve;

contacting the barrier member with the hand of the individual, the barrier member limiting the hand from exiting the sleeve through the opening before a glove is placed over the opening; and extending a hand of the arm through the opening at the distal end of the sleeve after the glove is placed over the opening.

IV-a. The method of claim IV, further comprising the step of manipulating the barrier member to allow the hand to bypass the barrier member after contacting the barrier member.

IV-b. The method of claim IV-a, wherein the barrier member comprises a piece of material including a perforation and the step of manipulating the barrier member further comprises separating/tearing/detaching at least a portion of the barrier member from an interior surface of the sleeve within the lumen to allow the hand to bypass the barrier member.

IV-c. The method of claim IV-a, wherein the barrier member comprises a zipper defining a seam and the step of manipulating the barrier member further comprises unzipping the zipper of the barrier member to open the seam and allow the hand to bypass the barrier member.

IV-d. The method of claim IV-a, wherein the step of manipulating the barrier member further comprises releasing a portion of the barrier member.

IV-e. The method of claim IV-a, wherein the barrier member comprises a plurality of layers folded over one another and the step of manipulating the barrier member further comprises unfolding the barrier member to allow the hand to bypass the barrier member.

IV-f. The method of claim IV, further comprising transitioning the barrier member from a closed configuration to an open configuration as the barrier member is manipulated by the individual to allow a portion of the individual's hand to extend past the barrier member and out of the opening.

IV-g. The method of any one of claims IV to IV-f, wherein covering the opening includes overlapping an exterior surface of the sleeve with a portion of the glove to provide a continuous sterile barrier between the glove and sleeve.

V. A method of donning a personal protection system, the method comprising:

providing a protective garment including a sleeve defining a lumen and an opening at a distal end of the sleeve, the lumen configured to receive an arm of an individual wearing the protective garment, and a barrier member transitionable from a closed configuration to an open configuration;

inserting a hand of the arm into the lumen through a proximal opening of the sleeve while the barrier member is in the closed configuration before a glove is placed over the opening;

placing a glove over the opening;

transitioning the barrier member from the closed configuration to the open configuration; and extending the hand through the opening at the distal end of the sleeve and into the glove while maintaining a sterile barrier between the individual and the external environment.

VI. A method of donning a personal protection system, the method comprising:

providing a protective garment including a sleeve defining a lumen and an opening at a distal end of the sleeve, the lumen configured to receive an arm of an individual wearing the protective garment, and a barrier member disposed within the lumen and configured to define an impermeable barrier preventing access to the lumen from an external environment via the opening;

inserting a hand of the arm of the individual into the lumen through a proximal opening of the sleeve;

contacting the barrier member with the hand of the individual, the barrier member limiting the hand from exiting the sleeve through the opening;

manipulating the barrier member to allow the hand to bypass the barrier member; and extending the hand through the opening at the distal end of the sleeve.

VI-a. The method of claim VI, further comprising the step of covering the opening at the distal end of the sleeve with a glove, the glove at least partially disposed on an exterior surface of the sleeve to form a sterile barrier with the sleeve between the lumen and the external environment.

VI-b. The method of claim VI-a, wherein the step of extending the hand through the opening further comprises extending the hand into the glove disposed over the opening while maintaining the sterile barrier.

VII. A surgical garment for use with a surgical helmet including a ventilation assembly, the surgical garment comprising:

a front panel, a rear panel, and a hood formed from a surgical fabric;

the rear panel including a first portion and a second portion, each of the first and second portions coupled to an opposing side of the front panel;

the hood comprising:

a front portion and a rear portion, the front portion coupled to the front panel;

a first opening defined in the surgical fabric of the hood;

a transparent face shield disposed over the first opening; and wherein the rear portion of the hood has a length sufficient to extend below a top edge of the rear panel such that a portion of the hood is positionable between the wearer and the rear panel.

VII-a. The surgical garment of claim VII, further comprising a second opening defined in the surgical fabric of the hood, a filter fabric disposed within the second opening, the second opening positioned to place the filter fabric adjacent the ventilation assembly of the surgical helmet.

VII-b. The surgical garment of claim VII, wherein the transparent face shield includes an upper portion and a lower portion; and wherein each of the upper portion and the lower portion of the transparent face shield further comprises at least one attachment element for removably coupling the surgical garment to the surgical helmet.

VII-c. The surgical garment of claim VII-b, wherein the at least one attachment element is formed from one of a magnetic or ferromagnetic material and is configured to magnetically couple to a coupling member of the surgical helmet.

VII-d. The surgical garment of claim VII, wherein the transparent face shield includes an upper portion and a lower portion;

a first attachment element secured to the upper portion of the transparent face shield;

a second attachment element secured to the lower portion of the transparent face shield; and each of the first and second attachment elements configured to removably couple to a coupling member of the surgical helmet.

VII-e. The surgical garment of claim VII, wherein the first and second portions of the rear panel are separated by a slit extending the length of the panel.

VII-f. The surgical garment of claim VII-e, further comprising a fastener for securing the first and second portions of the rear panel to one another.

VII-g. The surgical garment of claim VII-f, wherein the fastener comprises a zipper disposed along the length of the slit separating the first and second portions of the rear panel, the zipper configured to secure the first and second portions of the rear panel to another when in a closed position.

VII-h. The surgical garment of claim VII-f, wherein the fastener comprises at least two tie members, each of the two tie members coupled to one of the front or rear panel on opposing sides of the slit separating the first and second portions of the rear panel.

VII-i. The surgical garment of claim VII-h, wherein each of the at least two tie members comprises a proximal end and a distal end, the proximal end coupled to the front or rear panel; and a hook and loop fastener disposed on the distal end of one or more of the at least two tie members, the hook and loop fastener configured to removable secure the distal end of the at least two tie members to at least one of the front panel, the rear panel, or another of the at least two tie members.

VIII. A surgical system comprising:

a surgical helmet configured to be worn on a wearer's head, the surgical helmet comprising:

a ventilation system to circulate air about the wearer;

at least one coupling member;

a surgical garment configured to be at least partially disposed over the wearer and the surgical helmet, the surgical garment comprising:

a surgical fabric, the surgical fabric defining a hood and a body portion;

the hood having a front portion and a rear portion, the front portion coupled to the body portion and defining an opening configured to be in front of the wearer's face when disposed over wearer and the surgical helmet, and the rear portion defining a flap extending below a top edge of the body portion and configured to be at least partially disposed between the wearer and the body portion;

a transparent face shield disposed over the opening defined in the hood; and at least one attachment element disposed on the hood or transparent face shield, the attachment element for removably coupling the hood to the surgical helmet.

VIII-a. The surgical system of claim VIII, wherein the body portion further comprises a sleeve having a distal end defining a lumen for receiving an arm of the individual;

a cuff portion disposed at the distal end of the sleeve, the cuff portion extending the lumen defined by the sleeve and further defining an opening; and a barrier member disposed within the lumen proximal to the opening and configured to selectively prevent the hand of the individual from extending through the opening defined by the cuff portion.

VIII-b. The surgical system of claim VIII-a, wherein the barrier member is positioned within the lumen at an intersection of the distal end of the sleeve and a proximal end of the cuff portion.

VIII-c. The surgical system of claim VIII-a, wherein the barrier member is positioned within the opening defined by the cuff portion to seal the lumen defined by the cuff portion and the sleeve from the external environment.

VIII-d. The surgical system of any one of claims VIII-a to VIII-c, wherein the barrier member is configured to transition from a closed configuration to an open configuration.

VIII-e. The surgical system of claim VIII-c, wherein when the barrier member is in a closed configuration, the barrier member defines a barrier between the lumen defined by the sleeve and the external environment through the opening defined by the cuff portion.

VIII-f. The surgical system of claim VIII-c, wherein the barrier member comprises a sealing member configured to transition the barrier member from the closed configuration to the open configuration.

VIII-g. The surgical system of claim VIII-f, wherein the sealing member includes at least one of perforations, adhesives, stitching, and frangible connections.

VIII-h. The surgical system of any one of claims VIII to VIII-g, wherein the at least one attachment element comprises:

a pair of lower attachment elements disposed on a bottom portion of the transparent face shield; and an upper attachment element disposed on a top portion of the transparent face shield, the upper and lower attachment elements defining three mounting locations at which the face shield is removably mounted to the surgical helmet;

wherein the transparent face shield defines a bounded cut, the bounded cut being disposed between a sealing perimeter of the transparent face shield and an outer edge of the face shield; and wherein the bounded cut being at least partially disposed between the upper attachment element and the pair of lower attachment elements.

IX. A method of donning a surgical garment over a surgical helmet including a ventilation assembly, the method comprising:

attaching a transparent face shield of a hood portion of the surgical garment to the surgical helmet by coupling an attachment element on the transparent face shield to a coupling member on the surgical helmet;

manipulating a surgical fabric of the hood portion of the surgical garment to be disposed over the surgical helmet and head of the wearer;

manipulating a body portion of the surgical garment to cover a body of the wearer;

positioning a lower flap that extends from a rear of the hood portion of the surgical garment such that the flap is underneath the body portion of the surgical garment; and closing the surgical garment by pulling opposed sides of a rear portion of the body portion of the surgical garment toward one another; and securing the surgical garment to the wearer by fastening the opposed sides of a rear portion of the body portion to one another.

IX-a. The method of claim IX, wherein the step of securing the surgical garment to the wearer comprises zipping the opposed sides of a rear portion of the body portion to one another.

IX-b. The method of claim IX, wherein the step of securing the surgical garment to the wearer comprises wrapping a cord about an exterior of the surgical garment to hold the opposed sides of a rear portion of the body portion closed.

IX-c. The method of any one of claims IX to IX-b, further comprising:

inserting an arm of the wearer into a lumen defined by a sleeve of the body portion;

contacting a barrier member with a hand of the wearer, the barrier member preventing the hand from exiting through an opening at a distal end of the sleeve before a glove is placed over the opening; and extending a hand of the arm passed the barrier member and through the opening at the distal end of the sleeve after the glove is placed over the opening.

X. A surgical garment for use with a surgical helmet including a plurality of coupling members, the surgical garment comprising:

a shell formed from a fabric;

a face shield formed of a flexible and transparent material and including a top portion, a bottom portion, and a sealing perimeter, the shell sealed to the face shield along the sealing perimeter;

a pair of lower attachment elements disposed on the bottom portion of the face shield; and an upper attachment element disposed on the top portion of the face shield, the upper and lower attachment elements defining three mounting locations at which the face shield is removably mounted to the surgical helmet;

wherein the face shield defines a bounded cut, the bounded cut being disposed between the sealing perimeter and an outer edge of the face shield; and wherein the bounded cut being at least partially disposed between the upper attachment element and the pair of lower attachment elements.

X-a. The surgical garment of claim X, wherein a first imaginary line connects the upper attachment element to a first lower attachment element of the pair of lower attachment elements and a second imaginary line connects the upper attachment element to a second lower attachment element of the pair of lower attachment elements;

wherein at least one of the first imaginary line and the second imaginary line intersects the bounded cut when the face shield is in a flat state.

X-b. The surgical garment of claim X-a, wherein the first and second imaginary lines intersect the bounded cut when the face shield is in a flat configuration X-c. The surgical garment of claim X-a, a third imaginary line connects the pair of lower attachment elements, the first, second, and third imaginary lines intersect one another to define a triangle.

X-d. The surgical garment of claim X, wherein the pair of lower attachment elements are spaced laterally from one other such that each of the pair of lower attachment elements are disposed on opposing lateral sides of the face shield.

X-e. The surgical garment of claim X, wherein each of the upper and lower attachment elements are disposed on the face shield at locations corresponding to one of the plurality coupling members of the surgical helmet;

wherein each of the upper and lower attachment elements are formed from one of a ferromagnetic or magnetic material and each of the plurality of coupling members is formed from the other of the ferromagnetic or magnetic material.

X-f. The surgical garment of claim X, wherein the face shield further comprises a second bounded cut, the second bounded cut intersecting the other bounded cut.

X-g. The surgical garment of claim X, wherein a portion of the bounded cut is in a spiral configuration.

X-h. The surgical garment of claim X, wherein at least one of the attachment elements are disposed on the face shield between the sealing perimeter and an outer edge of the face shield.

X-i. The surgical garment of claim X, wherein at least one of the attachment elements comprises a head including a distal surface and an opposed proximal surface, the proximal surface defining a recess in the head.

X-j. The surgical garment of claim X, wherein the at least one of the attachment elements comprises one of a snap, pin, hook and loop, magnetic, or button fastener corresponding to the plurality of coupling features of the surgical helmet.

X-k. The surgical garment of claim X, furthering comprising a vertical axis defining a first lateral portion and a second lateral portion of the face shield;

wherein the bounded cut intersects that vertical axis such that the bounded cut is at least partially defined by each of the first portion and the second portion.

X-l. The surgical garment of claim X-k, wherein the vertical axis intersects the upper attachment element; and wherein each of the pair of lower attachment elements are disposed on the face shield on opposing sides of the vertical axis.

X-m. The surgical garment of claim X, wherein the pair of lower attachment elements are positioned on the face shield such that the face shield is in a flexed state when each of the pair of lower attachment elements are coupled to one of the plurality of coupling member of the surgical helmet; and wherein the bounded cut is configured to mitigates the strain on the face shield when in the flexed state.

XI. A surgical garment for use with a surgical helmet including a plurality of coupling members, the surgical garment comprising:

face shield formed of a flexible and transparent material and including an upper portion and a lower portion;

an upper attachment element disposed on the upper portion;

a pair of lower attachment elements disposed on the lower portion;

wherein each of the attachment elements are positioned to removably couple with one of the plurality of coupling members of the surgical helmet;

a bounded cut defined in the face shield, the bounded cut being at least partially disposed between the upper attachment element and at least one of the pair of lower attachment elements; and wherein the bounded cut being at least partially disposed between the upper attachment element and at least one of the pair of lower attachment elements to mitigate the stress on the face shield when in a flexed state created when each of the attachment element are coupled to one of the plurality of coupling member of the surgical helmet.

XI-a. The surgical garment of claim XI, further comprising a shell formed from a fabric, the shell defining an opening;

wherein the face shield includes a sealing perimeter, the shell sealed to the face shield along the sealing perimeter such that the face shield is disposed in the opening defined by the shell;

wherein at least one of the attachment elements is disposed on the face shield between the sealing perimeter and a perimeter edge of the face shield.

XI-b. The surgical garment of claim XI, wherein the bounded cut in the face shield extends a distance between opposing ends of the bounded cut, the bounded cut having a first dimension measured perpendicular to the longitudinal axis of the bounded cut; and an aperture defined in the face shield at each of the opposing ends of the bounded cut, each of the apertures having a second dimension;

wherein the second dimension is greater than the first dimension to reduce a stress concentration and/or prevent cracking at the opposing ends of the bounded cut.

XI-c. The surgical garment of claim XI, wherein the bounded cut defined by the face shield extends a distance between opposing ends of the bounded cut; and a second bounded cut in the face shield, the second bounded cut positioned on the face shield to intersect at least one of the opposing ends of the bounded cut to reduce a stress concentration and/or prevent cracking at the opposing ends of the bounded cut.

XI-d. The surgical garment of claim XI-c, wherein the second bounded cut is V-shaped with an apex of the second bounded cut in communication with one of the opposing ends of the bounded cut.

XII. A personal protection system comprising:

a surgical helmet including a plurality of coupling members;

surgical garment comprising:

a shell formed from a fabric;

a face shield formed of a flexible and transparent material and including a top portion, a bottom portion, and a sealing perimeter, the shell sealed to the face shield along the sealing perimeter;

a pair of lower attachment elements disposed on the bottom portion of the face shield in said bottom portion of the face shield; and an upper attachment element disposed on the top portion of the face shield in the top portion of the face shield, the upper and lower attachment elements defining three mounting locations at which the face shield is removably mounted to the surgical helmet;

wherein the face shield defining a bounded cut, the bounded cut being disposed between the sealing perimeter and an outer edge of the face shield; and wherein the cut being at least partially disposed between the upper attachment element and at least one of the pair of lower attachment elements.

XIII. A surgical garment for use with a surgical helmet, the surgical garment comprising:

a shell formed from a fabric;

a face shield formed of a flexible and transparent material and including a top portion, a bottom portion, and a sealing perimeter, the shell sealed to the face shield along the sealing perimeter;

a lower attachment element disposed on the bottom portion of the face shield; and a pair of upper attachment elements disposed on the top portion of the face shield, the upper and lower attachment elements defining three mounting locations at which the face shield is removably mounted to the surgical helmet;

wherein the face shield defining a bounded cut, the bounded cut being disposed between the sealing perimeter and an outer edge of the face shield; and wherein the bounded cut being at least partially disposed between at least one of the pair of upper attachment elements and the lower attachment element.

XIV. A method of forming a virus-impenetrable seal on a surgical garment between a flaccid shell and a transparent face shield, the method comprising:

providing a flaccid shell that defines a viral barrier, the flaccid shell defining an opening having a first shape for attachment of a transparent face shield, the shell including a first layer and a second layer;

positioning the flaccid shell such that the opening of the flaccid shell is at least partially disposed over and contacts a support surface, the support having a second shape, wherein the second shape is matched to the first shape;

contacting the flaccid shell with a heated platen while the opening of the flaccid shell is disposed over the support surface to irreversibly bond the first layer to the second layer to define a sealed perimeter region surrounding the opening of the flaccid shell;

applying an adhesive composition to at least one of a portion of the transparent face shield configured to contact the sealed perimeter region of the flaccid shell or a portion of the sealed perimeter region of the flaccid shell such that the applied adhesive composition defines an outline that surrounds the opening of the flaccid shell;

positioning the face shield relative to the flaccid shell such that the adhesive applied to the transparent face shield contacts the sealed perimeter region of the flaccid shell or the adhesive applied the sealed perimeter region of the flaccid shell contacts the face shield; and applying force to one of the face shield and the flaccid shell after the step of positioning the face shield relative to the flaccid shell before the adhesive has completed a curing step.

XIV-a. The method of claim XIV, wherein the sealed perimeter region has a thickness of at least 10 mm.

XIV-b. The method of claim XIV-a, wherein the sealed perimeter region has a thickness of at 10 mm to 25 mm.

XIV-c. The method of claim XIV-a, wherein the sealed perimeter region has a thickness of at least 15 mm.

XIV-d. The method of claim XIV-a, wherein the sealed perimeter region has a thickness of at least 20 mm.

XIV-e. The method of any one of claims XIV to XIV-d, further comprising the step of positioning the flaccid shell such that the opening of the flaccid shell is at least partially disposed about a contoured protrusion extending above the support surface such that the opening in flaccid shell at least partially encircles the contoured protrusion and contacts the support surface, the contoured protrusion having a second shape, wherein the second shape is matched to the first shape of the opening defined in the flaccid shell and the platen defines a platen opening that receives the contoured protrusion during the step of contacting the flaccid shell with the heated platen.

XIV-f. The method of claim XIV-e, wherein the contoured protrusion comprises a top surface and perimeter surface, the perimeter surface extending between the support surface and the top surface, the contoured protrusion defining one of a chamfer, rounded edge, or bevel where the perimeter surface intersects the top surface;

the method further comprising the step using the chamfer, rounded edge, or bevel where the perimeter surface intersects the top surface to align the opening of the flaccid shell with the contoured protrusion when positioning the flaccid shell about the contoured protrusion and onto the support surface.

XIV-g. The method of any one of claims XIV to XIV-f, wherein the flaccid shell comprises a material that provides a breathable viral barrier.

XIV-h. The method of any one of claims XIV to XIV-g, further comprising the step of cooling one of the support surface and platen after contacting the flaccid shell with the heated platen.

XIV-i. The method of any one of claims XIV to XIV-h, wherein the heated platen includes a heating element, wherein the heating element has a shape similar to the second shape.

XIV-j. The method of any one of claims XIV to XIV-h, wherein the support includes a heating element, wherein the heating element has a shape similar to the second shape.

XIV-k. The method of any one of claims XIV to XIV-h, wherein both the heated platen and the support include heating elements, wherein the heating elements have a shape similar to the second shape.

XIV-l. The method of any one of claims XIV-i to XIV-k, wherein the heating element is formed in a closed shape corresponding to the opening of the shell.

XIV-m. The method of any one of claims XIV-i to XIV-k, wherein the heating element is a resistive heating element.

XIV-n. The method of any one of claims XIV to XIV-m, wherein the flaccid shell further comprises a third layer, the first, second and third layers bonded to the adjacent layer by an adhesive.

XIV-o. The method of claim XIV-n, wherein at least one of the first layer, second layer, and third layer is a non-woven flaccid material.

XIV-p. The method of claim XIV, wherein the transparent face shield is formed from at least one of a polyester or a polycarbonate material.

XIV-q. The method of any one of claims XIV to XIV-p, wherein the adhesive is applied such that a portion of the sealed perimeter region is not covered by adhesive.

XIV-r. The method of any one of claims XIV to XIV-q, wherein the step of applying an adhesive composition comprises applying the adhesive to the adhesive region of the transparent face shield; and the step of positioning the face shield comprises positioning the flaccid shell such that the adhesive applied to the transparent face shield contacts the sealed perimeter region of the flaccid shell or the adhesive applied the sealed perimeter region of the flaccid shell contacts the face shield.

XIV-s. The method of any one of claims XIV to XIV-q, wherein the step of applying an adhesive composition comprises applying the adhesive to the sealed perimeter region of the flaccid shell; and the step of the step of positioning the face shield comprises positioning the flaccid shell such that the adhesive applied the sealed perimeter region of the flaccid shell contacts the face shield.

XIV-t. The method of any one of claims XIV to XIV-s, wherein the step of applying force to one of the transparent face shield and the flaccid shell after the step of positioning the face shield relative to the flaccid shell further comprises rolling a roller over a surface of one of the transparent face shield and the flaccid shell opposite a surface of the flaccid shell or transparent face shield where the adhesive is applied.

XIV-u. The method of claim XIV-t, further comprising a step of tracing the adhesive with the roller.

XV. A surgical garment comprising:

a flaccid shell defining an opening, the shell comprising:

a first layer;

a second layer coupled to the first layer;

wherein the first and second layers define a sealing perimeter about the opening, the first and second layers coupled such that the first and second layers are more tightly bound together within the sealing perimeter than the first and second layers outside the sealing perimeter;

a transparent face shield shaped to be disposed over the opening; and a pressure sensitive adhesive disposed between the transparent face shield and the sealing perimeter of the flaccid shell to couple the transparent face shield to the flaccid shell.

XV-a. The surgical garment of claims XV, wherein the pressure sensitive adhesive comprises a rubber-based adhesive.

XV-b. The surgical garment of claims XV, wherein the pressure sensitive adhesive comprises a silicone-based adhesive.

XVI. A surgical garment comprising:

a flaccid shell defining an opening, the shell comprising:

a first layer;

a second layer coupled to the first layer;

wherein the first and second layers define a sealing perimeter about the opening;

the first and second layers coupled such that the first and second layers define a first thickness within the sealing perimeter and define a second thickness outside the sealing perimeter, the first thickness being less than the second thickness;

a transparent face shield shaped to be disposed over the opening; and a pressure sensitive adhesive disposed between the transparent face shield and the sealing perimeter of the flaccid shell to couple the transparent face shield to the flaccid shell.

XVII. A protective surgical garment worn by an individual, the protective surgical garment comprising:

a garment body including a material configured to provide a sterile barrier between the individual and an external environment; and a sleeve extending from the garment body, the sleeve having a distal end and a proximal end and defining a lumen for receiving an arm of the individual, the sleeve defining a barrier to limit a hand of the arm of the individual from inadvertently exiting through the sleeve.

XVIII. A protective surgical garment worn by an individual, the protective surgical garment comprising:

a garment body including a material configured to provide a sterile barrier between the individual and an external environment;

a sleeve extending from the garment body, the sleeve having a distal end and a proximal end and defining a lumen for receiving an arm of the individual; and a sleeve insert coupled to the sleeve to partially occlude the lumen, the sleeve insert including perforations.

XVIII-a. The protective surgical garment of claim XVIII, wherein the sleeve inert is formed from a fabric extending across and at least partially enclosing the lumen.

XVIII-b. The protective surgical garment of claim XVIII or XVIII-a, wherein sleeve insert comprises at least a first portion and a second portion defined by the perforations, the perforations creating a frangible connection between the first and second portions of the sleeve insert that is breakable by the hand of the individual to transition the sleeve insert from a closed configuration to an open configuration.

XVIII-c. The protective surgical garment of any one of claims XVIII to XVIII-b, wherein the perforations of the sleeve insert are defined along a first line and along a second line, the first line intersecting the second line.

XVIII-d. The protective surgical garment of any one of claims XVIII to XVIII-c, wherein the sleeve insert is stitched to the sleeve.

XVIII-e. The protective surgical garment of any one of claims XVIII to XVIII-d, furthering comprising a cuff disposed at the distal end of the sleeve, the cuff stitched to at least one of the sleeve or the sleeve insert.

XIX. A method of manufacturing a protective surgical garment, the method comprising:

providing garment with a sleeve defining a lumen; and attaching a sleeve insert to the sleeves such that a portion of the sleeve insert partially occludes the lumen, the sleeve insert including a perforation.

XIX-a. The method of claim XIX, further comprising the step of stitching a cuff to a distal end of the sleeve, the cuff extending the lumen defined by the sleeve.

XIX-b. The method of claim XIX or XIX-a, further comprising the step of die-cutting a fabric the sleeve insert is formed from to form the perforations.

XIX-c. The method of any one of claims XIX to XIX-b, further comprising the step of cutting the sleeve insert to be circular shaped.

XX. A surgical garment for use with a surgical helmet including a ventilation assembly, the surgical garment comprising:

a front panel, a rear panel, and a hood formed from a surgical fabric;

the rear panel including a first back flap and a second back flap, each of the first and second back flaps extending from opposing sides of the front panel;

the hood defining a front portion and a rear portion, the front portion coupled to the front panel, the rear portion including a hood flap; and wherein the hood flap and the first and second back flaps are dimensioned such that the hood flap is positionable at least partially underneath the first and second back flaps.

XX-a. The surgical garment of claim XX, wherein the first and second portions of the rear panel are separated by a slit extending the length of the panel.

XX-b. The surgical garment of claim XX-a, further comprising a fastener for securing the first and second portions of the rear panel to one another.

XX-c. The surgical garment of claim XX-b, wherein the fastener comprises a zipper disposed along the length of the slit separating the first and second portions of the rear panel, the zipper configured to secure the first and second portions of the rear panel to another when in a closed position.

XX-d. The surgical garment of claim XX-b, wherein the fastener comprises at least two tie members, each of the two tie members coupled to one of the front or rear panel on opposing sides of the slit separating the first and second portions of the rear panel.

XX-e. The surgical garment of claim XX-d, wherein each of the at least two tie members comprises a proximal end and a distal end, the proximal end coupled to the front or rear panel; and a hook and loop fastener disposed on the distal end of one or more of the at least two tie members, the hook and loop fastener configured to removable secure the distal end of the at least two tie members to at least one of the front panel, the rear panel, or another of the at least two tie members.

XX-f. The surgical garment of any one of claims XX to XX-e, wherein the hood flap further comprises a hood fastener; and each of the first back flap and the second back flap comprise a rear flap fastener;

wherein the hood fastener and the rear flap fastener are arranged to removably couple the hood flap to each of the first back flap and the second back flap.

XX-g. The surgical garment of claim XX-f, wherein the hood fastener is disposed on an outer surface of the hood flap; and the rear flap fastener(s) are disposed on an inner surface of each of the first back flap and the second back flap.

XX-h. The surgical garment of claim XX-f or XX-g, wherein the hood fastener and the rear flap fastener(s) comprise one of snaps, hook and loop, buttons and openings, magnets, or a similar fastening mechanism.

XXI. A surgical apparel system worn by an individual, the system comprising:

a sleeve having a distal end defining a lumen for receiving an arm of the individual;

a cuff portion disposed at the distal end of the sleeve, the cuff portion extending the lumen defined by the sleeve and further defining an opening; and a barrier member disposed within the lumen proximal to the opening and configured to selectively prevent a hand of the individual's arm from extending through the opening defined by the cuff portion.

XXI-a. The system of claim XXI, further comprising a glove including a glove opening, the glove configured to overlap a portion of at least one of the cuff portion and the sleeve and covering the opening of the cuff portion to maintain sterility within the lumen.

XXI-b. The system of claim XXI or XXI-a, further comprising:

a body portion, the sleeve extending from the body portion;

a hood coupled to the body portion, the hood defining an opening configured to be in front of the individual's face when disposed over individual and/or a surgical helmet;

a transparent face shield disposed over the opening defined in the hood; and at least one attachment element disposed on the hood and/or transparent face shield, the attachment element for removably coupling the surgical garment to the surgical helmet.

XXI-c. The system of claim XXI-b, wherein the body portion comprises:

a front panel;

a rear panel including a first back flap and a second back flap, each of the first and second back flaps extending from opposing sides of the front panel;

the hood defining a front portion and a rear portion, the front portion coupled to the front panel, the rear portion including a hood flap; and wherein the hood flap and the first and second back flaps are dimensioned such that the hood flap is positionable at least partially underneath the first and second back flaps.

It will be further appreciated that the terms "include," "includes," and "including" have the same meaning as the terms "comprise," "comprises," and "comprising."

Several examples have been described in the foregoing description. However, the examples discussed herein are not intended to be exhaustive or limit the invention to any particular form. The terminology, which has been used, is intended to be in the nature of words of description rather than of limitation. Many modifications and variations are possible in light of the above teachings and the invention may be practiced otherwise than as specifically described.

The many features and advantages of the invention are apparent from the detailed specification, and thus, it is intended by the appended claims to cover all such features and advantages of the invention which fall within the true spirit and scope of the invention. Further, since numerous modifications and variations will readily occur to those skilled in the art, it is not desired to limit the invention to the exact construction and operation illustrated and described, and accordingly, all suitable modifications and equivalents may be resorted to, falling within the scope of the invention.

What is claimed is:

1. A surgical garment worn by an individual, the surgical garment comprising: a sleeve having a distal end defining a lumen for receiving an arm of the individual; a cuff portion disposed at the distal end of the sleeve, the cuff portion extending the lumen defined by the sleeve and further defining a cuff opening; a barrier member disposed within the lumen defined by the sleeve and cuff portion, the barrier member positioned at the distal end of the sleeve and proximal to the cuff opening; and wherein the barrier member comprises a first portion and a second portion that are selectively coupled to one another, the first and second portions being separable from one another by the individual and configured to transition from a closed configuration that prevents a hand of the individual's arm from extending through the cuff opening defined by the cuff portion, to an open configuration.

2. The surgical garment of claim 1, wherein the barrier member is positioned within the lumen at an intersection of the distal end of the sleeve and a proximal end of the cuff portion.

3. The surgical garment of claim 1, wherein the barrier member is positioned within a sleeve opening defined at the distal end of the sleeve and proximal to the cuff portion to at least partially enclose the lumen defined by the sleeve from the cuff portion and the external environment.

4. The surgical garment of claim 1, wherein when the barrier member is in the closed configuration, the barrier member defines a barrier between the lumen defined by the sleeve of the surgical garment and the external environment of the surgical garment.

5. The surgical garment of claim 1, wherein the first portion and the second portion of the barrier member are joined by a fastener configured to transition the barrier member from the closed configuration to the open configuration; and wherein the fastener includes at least one of a zipper, snaps, hook and loop, stitching, and/or adhesive configured to selectively join the first and second portions of the barrier member.

6. The surgical garment of claim 1, wherein the barrier member is a film spanning the cuff opening defined by the cuff portion to seal an internal environment of the sleeve from the external environment, the film is configured to be breachable by the hand of the individual.

7. The surgical garment of claim 1, wherein the first portion and the second portion of the barrier member are selectively coupled to one another by one or more perforations, the perforations creating a frangible connection between the first and second portions of the barrier member that is breakable by the hand of the individual to transition the barrier member from the closed configuration to the open configuration.

8. The surgical garment of claim 1, wherein the barrier member is coupled to the distal end of the sleeve and the barrier member at least partially covers a sleeve opening defined at the distal end of the sleeve; and wherein the barrier member is coupled to the sleeve via stitching.

9. The surgical garment of claim 8, wherein the cuff portion is partially disposed over the barrier member and is coupled to the distal end of the sleeve via stitching, the cuff opening defined by the cuff portion being distal to the barrier member.

10. A protective surgical garment worn by an individual, the protective surgical garment comprising:

a garment body including a material configured to provide a sterile barrier between the individual and an external environment;

a sleeve extending from the garment body, the sleeve having a distal end and a proximal end and defining a lumen that extends between the distal and proximal ends for receiving an arm of the individual; and a sleeve insert disposed entirely within the lumen defined by the sleeve proximate to the distal end of the sleeve, the sleeve insert including a first portion and a second portion coupled to one another by perforations, the perforations defining a frangible connection between the first and second portions of the sleeve insert that is breakable by the hand of the individual to transition the sleeve insert from a closed configuration to an open configuration.

11. The protective surgical garment of claim 10, wherein the sleeve insert is formed from a fabric extending across and at least partially enclosing the lumen.

12. The protective surgical garment of claim 10, wherein the perforations of the sleeve insert are defined along a first line and along a second line, the first line intersecting the second line.

13. The protective surgical garment of claim 10, wherein the sleeve insert is stitched to the sleeve; and further comprises a cuff disposed at the distal end of the sleeve, the cuff including a proximal end being stitched to at least one of the sleeve and/or the sleeve insert and a cuff opening at a distal end of the cuff;

wherein the sleeve insert is positioned proximally to the cuff opening.

14. A method of donning a personal protection system, the method comprising:

providing a protective garment including a sleeve defining a lumen having a distal opening at a distal end of the sleeve and a proximal opening at the proximal end of the sleeve, the lumen configured to receive an arm of an individual wearing the protective garment, and a barrier member disposed within the lumen and configured to define a barrier for selectively limiting access to the lumen from an external environment via the distal opening;

inserting the arm of the individual into the lumen through the proximal opening of the sleeve;

contacting the barrier member that is disposed within the lumen proximal to the distal opening of the sleeve with a hand of the individual, the barrier member comprising a first portion and a second portion coupled together to form a seal between the lumen and the external environment outside the distal opening and configured to selectively prevent the hand from exiting the sleeve through the distal opening of the sleeve before a glove is placed over the distal opening;

decoupling the first and second portions of the barrier member from one another; and extending the hand of the arm between the first and second portions and through the distal opening at the distal end of the sleeve after the glove is placed over the distal opening.

15. The method of claim 14, wherein the barrier member comprises a frangible piece of material including a perforation and the step of decoupling the first and second portions of the barrier member from one another comprises at least one of separating, tearing, and/or detaching the first portion from the second portion of the barrier member to allow the hand to bypass the barrier member.

16. The method of claim 14, further comprising transitioning the barrier member from a closed configuration to an open configuration as the barrier member is manipulated by the individual to allow a portion of the hand of the individual to extend between the first and second portions of the barrier member and out of the opening.

17. The method of claim 14, further comprising the step of covering the distal opening with the glove, wherein covering the distal opening with the glove includes overlapping an exterior surface of the sleeve with a portion of the glove to provide a continuous sterile barrier between the glove and sleeve.

* * * * *